(12) United States Patent
Ito et al.

(10) Patent No.: US 11,643,474 B2
(45) Date of Patent: May 9, 2023

(54) PEPTIDE FUSION PROTEIN

(71) Applicants: KAGOSHIMA UNIVERSITY, Kagoshima (JP); DAICEL CORPORATION, Osaka (JP)

(72) Inventors: Yuji Ito, Kagoshima (JP); Seiichi Uchimura, Tokyo (JP); Hiromichi Okura, Tokyo (JP)

(73) Assignees: KAGOSHIMA UNIVERSITY, Kagoshima (JP); DAICEL CORPORATION, Osaka (JP)

( * ) Notice: Subject to any disclaimer, the term of this patent is extended or adjusted under 35 U.S.C. 154(b) by 0 days.

(21) Appl. No.: 17/264,577

(22) PCT Filed: Aug. 1, 2019

(86) PCT No.: PCT/JP2019/030115
§ 371 (c)(1),
(2) Date: Jan. 29, 2021

(87) PCT Pub. No.: WO2020/027237
PCT Pub. Date: Feb. 6, 2020

(65) Prior Publication Data
US 2021/0332152 A1   Oct. 28, 2021

(30) Foreign Application Priority Data
Aug. 1, 2018 (JP) .............................. JP2018-145323

(51) Int. Cl.
| | |
|---|---|
| *C07K 1/22* | (2006.01) |
| *C07K 14/435* | (2006.01) |
| *C07K 17/00* | (2006.01) |
| *C07K 19/00* | (2006.01) |
| *C07K 7/08* | (2006.01) |

(52) U.S. Cl.
CPC ................ *C07K 19/00* (2013.01); *C07K 1/22* (2013.01); *C07K 7/08* (2013.01); *C07K 14/43595* (2013.01); *C07K 17/00* (2013.01)

(58) Field of Classification Search
CPC ...... C07K 1/22; C07K 7/08; C07K 14/43595; C07K 17/00; C07K 19/00
See application file for complete search history.

(56) References Cited

U.S. PATENT DOCUMENTS

| | | | | |
|---|---|---|---|---|
| 9,714,274 B2 * | 7/2017 | Liu | ...................... | C07K 14/585 |
| 2003/0203355 A1 * | 10/2003 | Bradbury | ............. | G01N 33/582 |
| | | | | 435/7.1 |
| 2005/0142623 A1 | 6/2005 | Yanagawa et al. | | |
| 2010/0105882 A1 | 4/2010 | Katayama | | |
| 2010/0167348 A1 | 7/2010 | Ochi et al. | | |
| 2010/0279306 A1 * | 11/2010 | Bosques | ............. | G01N 33/6842 |
| | | | | 435/7.1 |
| 2014/0274790 A1 | 9/2014 | Ito | | |
| 2015/0044701 A1 | 2/2015 | Ito et al. | | |
| 2015/0353608 A1 | 12/2015 | Watanabe et al. | | |
| 2016/0223441 A1 * | 8/2016 | Gjerde | ................. | C12N 5/0647 |
| 2017/0210777 A1 | 7/2017 | Minami | | |
| 2019/0194249 A1 | 6/2019 | Watanabe et al. | | |
| 2019/0367560 A1 | 12/2019 | Ito et al. | | |
| 2020/0032275 A1 | 1/2020 | Nakano et al. | | |

FOREIGN PATENT DOCUMENTS

| | | | | |
|---|---|---|---|---|
| CN | 103890174 A | 6/2014 | | |
| EP | 3 811 978 A1 | 4/2021 | | |
| EP | 3 865 515 A1 | 8/2021 | | |
| JP | 2002-526108 A | 8/2002 | | |
| JP | 2007-244285 A | 9/2007 | | |
| JP | 2011-521653 A | 7/2011 | | |
| JP | 2014-503790 A | 2/2014 | | |
| JP | 2015-501299 A | 1/2015 | | |
| JP | 2016-202044 A | 12/2016 | | |
| WO | WO 00/20574 A2 | 4/2000 | | |
| WO | WO 00/27872 A1 | 5/2000 | | |
| WO | WO 2008/069232 A1 | 6/2008 | | |
| WO | WO 2009/025300 A1 | 2/2009 | | |
| WO | WO 2009/146755 A1 | 12/2009 | | |
| WO | WO 2012/054648 A2 | 4/2012 | | |
| WO | WO-2012104791 A1 * | 8/2012 | ....... | C07K 14/43595 |
| WO | WO 2013/027796 A1 | 2/2013 | | |
| WO | WO 2013/055404 A1 | 4/2013 | | |
| WO | WO 2013/081037 A1 | 6/2013 | | |
| WO | WO 2014/115229 A1 | 7/2014 | | |
| WO | WO 2015/053353 A1 | 4/2015 | | |
| WO | WO 2016/052073 A1 | 4/2016 | | |
| WO | WO 2016/204198 A1 | 12/2016 | | |
| WO | WO 2017/200461 A1 | 11/2017 | | |
| WO | WO 2018/043629 A1 | 3/2018 | | |
| WO | WO 2018/092867 A1 | 5/2018 | | |

OTHER PUBLICATIONS

Pille et al. General Strategy for Ordered Noncovalent Protein Assembly on Well-Defined Nanoscaffolds. Biomacromolecules. Nov. 1, 2013, vol. 14, pp. 4351-4359. (Year: 2013).*

Sockolosky et al. Fusion of a Short Peptide that Binds Immunoglobulin G to a Recombinant Protein Substantially Increases Its Plasma Half-Life in Mice. Plos One. Jul. 2014, vol. 9, Issue 7, e102566. (Year: 2014).*

Yang et al. Construction of the fusion protein between EGFP and IgG-binding peptide. Chinese journal of marine drugs/Zhongguo Haiyang Yaowu. Mar. 2007, vol. 26, No. 5, pp. 29-33. (Year: 2007).*

(Continued)

*Primary Examiner* — Jeffrey E. Russel
(74) *Attorney, Agent, or Firm* — Birch, Stewart, Kolasch & Birch, LLP

(57) ABSTRACT

An object of the present invention is to provide a method by which a peptide having a specific binding capability that can be used for purification of a target molecule can be produced at a low cost, and specifically relates to a peptide fusion protein including one or more peptides having specific binding capability and a scaffold protein, the peptide being inserted into the amino acid sequence of the scaffold protein directly or via a peptide linker, and/or being linked to the N-terminal and/or C-terminal of the scaffold protein.

12 Claims, 15 Drawing Sheets

Specification includes a Sequence Listing.

(56) References Cited

OTHER PUBLICATIONS

Yu et al. Synthetic fusion protein design and applications. Biotechnology Advances. 2015, vol. 33, pp. 155-164. Available online Nov. 18, 2014. (Year: 2014).*
Pedelacq et al. Engineering and characterization of a superfolder green fluorescent protein. Nature Biotechnology. Jan. 2006, vol. 24, No. 1, pp. 79-88. (Year: 2006).*
International Search Report issued in PCT/JP2019/030115 (PCT/ISA/210), dated Oct. 29, 2019.
Written Opinion of the International Searching Authority issued in PCT/JP2019/030115 (PCT/ISA/237), dated Oct. 29, 2019.
Extended European Search Report for European Patent Application No. 19845061.1, dated Sep. 30, 2021.
Japanese Office Action for Japanese Application No. 2020-534727, dated May 10, 2022.
Chinese Office Action and Search Report for Chinese Application No. 201980049450.0 dated Nov. 1, 2022.

* cited by examiner

UNDERLINED: LINKER SEQUENCE
BOLD: IgG-BINDING PEPTIDE SEQUENCE
ITALIC: His tag FOR PURIFICATION

[COMPARATIVE EXAMPLE 1: sfGFP]
DNA SEQUENCE (SEQ ID NO: 40)
ATGCGTAAGGGCGAGGAACTGTTCACCGGCGTGGTTCCGATCCTGGTGGAGCTGGACGGTGA
TGTTAACGGCCACAAATTTAGCGTGCGTGGCGAGGGTGAAGGTGATGCGACCAACGGCAAGC
TGACCCTGAAATTCATTTGCACCACCGGCAAGCTGCCGGTGCCGTGGCCGACCCTGGTTACC
ACCCTGACCTACGGTGTGCAGTGCTTTGCGCGTTATCCGGACCACATGAAGCAACACGATTT
CTTTAAAAGCGCGATGCCGGAGGGTTACGTTCAAGAACGTACCATCAGCTTCAAGGACGATG
GCACCTATAAACCCGTGCGGAAGTGAAGTTTGAAGGTGACACCCTGGTTAACCGTATCGAG
CTGAAGGGCATTGACTTCAAAGAAGATGGTAACATCCTGGGCCACAAACTGGAGTACAACTT
TAACAGCCACAACGTTTATATTACCGCGGATAAGCAGAAAAACGGTATCAAGGCGAACTTTA
AAATTCGTCACAACGTGGAAGACGGCAGCGTTCAACTGGCGGATCACTACCAGCAAAACACC
CCGATTGGTGATGGTCCGGTGCTGCTGCCGGATAACCACTATCTGAGCACCCAGAGCGTTCT
GAGCAAGGACCCGAACGAGAAACGTGATCACATGGTGCTGCTGGAATTCGTTACCGCGGCGG
GTATTACCCACGGCATGGATGAACTGTATAAGGGTGGCGGTCATCACCACCACCACCACTAA

AMINO ACID SEQUENCE (SEQ ID NO: 41)
MRKGEELFTGVVPILVELDGDVNGHKFSVRGEGEGDATNGKLTLKFICTTGKLPVPWPTLVT
TLTYGVQCFARYPDHMKQHDFFKSAMPEGYVQERTISFKDDGTYKTRAEVKFEGDTLVNRIE
LKGIDFKEDGNILGHKLEYNFNSHNVYITADKQKNGIKANFKIRHNVEDGSVQLADHYQQNT
PIGDGPVLLPDNHYLSTQSVLSKDPNEKRDHMVLLEFVTAAGITHGMDELYK<u>GGG</u>*HHHHHH*\*

FIG. 1-1

UNDERLINED: LINKER SEQUENCE
BOLD: IgG-BINDING PEPTIDE SEQUENCE
ITALIC: His tag FOR PURIFICATION

[EXAMPLE 1: sfGFP-C-1Opt1]
DNA SEQUENCE (SEQ ID NO: 42)
ATGCGTAAAGGCGAGGAACTGTTTACCGGTGTGGTTCCGATCCTGGTGGAACTGGACGGCGA
TGTTAACGGTCACAAGTTCAGCGTTCGTGGTGAGGGCGAAGGTGACGCGACCAACGGCAAGC
TGACCCTGAAATTTATTTGCACCACCGGTAAACTGCCGGTGCCGTGGCCGACCCTGGTTACC
ACCCTGACCTACGGTGTGCAGTGCTTCGCGCGTTATCCGGACCACATGAAGCAACACGATTT
CTTTAAAAGCGCGATGCCGGAGGGCTACGTTCAGGAACGTACCATCAGCTTCAAGGACGATG
GTACCTATAAACCCGTGCGGAAGTGAAGTTTGAAGGCGACACCCTGGTTAACCGTATCGAG
CTGAAGGGTATTGACTTCAAAGAAGATGGCAACATCCTGGGTCACAAGCTGGAGTACAACTT
TAACAGCCACAACGTGTATATTACCGCGGATAAGCAGAAAAACGGCATCAAGGCGAACTTCA
AAATTCGTCACAACGTGGAAGACGGTAGCGTTCAACTGGCGGATCACTACCAGCAAAACACC
CCGATTGGTGATGGTCCGGTGCTGCTGCCGGATAACCACTATCTGAGCACCCAAAGCGTTCT
GAGCAAGGACCCGAACGAGAAACGTGATCACATGGTGCTGCTGGAATTTGTTACCGCGGCGG
GCATTACCCACGGTATGGACGAGCTGTACAAAGGTGGCGGTGGCAGCGGTGGCGGTGGCAGC
GGCCCGGATTGCGCGTATCACCGCGGCGAACTGGTTTGGTGCACCTTCCACGGCGGCGGTCA
TCATCATCATCATCACTAA

AMINO ACID SEQUENCE (SEQ ID NO: 43)
MRKGEELFTGVVPILVELDGDVNGHKFSVRGEGEGDATNGKLTLKFICTTGKLPVPWPTLVT
TLTYGVQCFARYPDHMKQHDFFKSAMPEGYVQERTISFKDDGTYKTRAEVKFEGDTLVNRIE
LKGIDFKEDGNILGHKLEYNFNSHNVYITADKQKNGIKANFKIRHNVEDGSVQLADHYQQNT
PIGDGPVLLPDNHYLSTQSVLSKDPNEKRDHMVLLEFVTAAGITHGMDELYK<u>GGGGSGGGGS</u>
GPDCAYHRGELVWCTFH<u>GGG</u>*HHHHHH*\*

FIG. 1-2

UNDERLINED: LINKER SEQUENCE
BOLD: IgG-BINDING PEPTIDE SEQUENCE
ITALIC: His tag FOR PURIFICATION

[EXAMPLE 2: sfGFP-N C-2Opt1GSl2]
DNA SEQUENCE (SEQ ID NO: 44)
ATGGGTCCGGACTGCGCGTATCACCGTGGCGAGCTGGTGTGGTGCACCTTTCATGGTGGCGG
TGGCAGCGGTGGCGGTGGCAGCCGTAAAGGCGAGGAACTGTTTACCGGTGTGGTTCCGATCC
TGGTGGAACTGGACGGCGATGTTAACGGTCACAAGTTCAGCGTTCGTGGTGAGGGCGAAGGT
GACGCGACCAACGGCAAGCTGACCCTGAAATTTATTTGCACCACCGGTAAACTGCCGGTGCC
GTGGCCGACCCTGGTTACCACCCTGACCTACGGTGTGCAGTGCTTCGCGCGTTATCCGGACC
ACATGAAGCAACACGATTTCTTTAAAAGCGCGATGCCGGAGGGCTACGTTCAGGAACGTACC
ATCAGCTTCAAGGACGATGGTACCTATAAACCCGTGCGGAAGTGAAGTTTGAAGGCGACAC
CCTGGTTAACCGTATCGAGCTGAAGGGTATTGACTTCAAAGAAGATGGCAACATCCTGGGTC
ACAAGCTGGAGTACAACTTTAACAGCCACAACGTGTATATTACCGCGGATAAGCAGAAAAAC
GGCATCAAGGCGAACTTCAAAATTCGTCACAACGTGGAAGACGGTAGCGTTCAACTGGCGGA
TCACTACCAGCAAAACACCCCGATTGGTGATGGTCCGGTGCTGCTGCCGGATAACCACTATC
TGAGCACCCAAAGCGTTCTGAGCAAGGACCCGAACGAGAAACGTGATCACATGGTGCTGCTG
GAATTTGTTACCGCGGCGGGCATTACCCACGGTATGGACGAGCTGTACAAAGGTGGCGGTGG
CAGCGGTGGCGGTGGCAGCGGCCCGGATTGCGCGTATCACCGCGGCGAACTGGTTTGGTGCA
CCTTCCACGGCGGCGGTCATCATCATCATCATCACTAA

AMINO ACID SEQUENCE (SEQ ID NO: 45)
MGPDCAYHRGELVWCTFH<u>GGGGSGGGGS</u>RKGEELFTGVVPILVELDGDVNGHKFSVRGEGEG
DATNGKLTLKFICTTGKLPVPWPTLVTTLTYGVQCFARYPDHMKQHDFFKSAMPEGYVQERT
ISFKDDGTYKTRAEVKFEGDTLVNRIELKGIDFKEDGNILGHKLEYNFNSHNVYITADKQKN
GIKANFKIRHNVEDGSVQLADHYQQNTPIGDPVLLPDNHYLSTQSVLSKDPNEKRDHMVLL
EFVTAAGITHGMDELYK<u>GGGGSGGGGS</u>GPDCAYHRGELVWCTFH<u>GGG</u>*HHHHHH**

FIG. 1-3

UNDERLINED: LINKER SEQUENCE
BOLD: IgG-BINDING PEPTIDE SEQUENCE
ITALIC: His tag FOR PURIFICATION

[EXAMPLE 2: sfGFP-173 C-2Opt1GSl2]
DNA SEQUENCE (SEQ ID NO: 46)
ATGCGTAAAGGCGAGGAACTGTTCACCGGTGTGGTTCCGATCCTGGTGGAGCTGGACGGCGA
TGTTAACGGTCACAAGTTTAGCGTGCGTGGTGAGGGCGAAGGTGACGCGACCAACGGCAAGC
TGACCCTGAAATTCATTTGCACCACCGGTAAACTGCCGGTGCCGTGGCCGACCCTGGTTACC
ACCCTGACCTACGGTGTGCAGTGCTTTGCGCGTTATCCGGACCACATGAAGCAACACGATTT
CTTTAAAAGCGCGATGCCGGAGGGCTACGTTCAGGAACGTACCATCAGCTTCAAGGACGATG
GTACCTATAAACCCGTGCGGAAGTGAAGTTTGAAGGCGATACCCTGGTTAACCGTATCGAG
CTGAAGGGTATTGACTTCAAAGAAGATGGCAACATCCTGGGTCACAAGCTGGAATACAACTT
TAACAGCCACAACGTGTATATTACCGCGGACAAGCAGAAGAACGGTATCAAGGCGAACTTTA
AAATTCGTCACAACGTTGAGGGTGGCGGTGGCAGCGGCGGTGGCGGTAGCGGTCCGGATTGC
GCGTACCACCGTGGTGAACTGGTGTGGTGCACCTTTCATGGCGGTGGCGGTAGCGGCGGTGG
CGGTAGCGATGGTAGCGTTCAGCTGGCGGATCACTACCAGCAAAACACCCCGATTGGTGATG
GTCCGGTGCTGCTGCCGGATAACCACTATCTGAGCACCCAAAGCGTTCTGAGCAAGGACCCG
AACGAGAAACGTGATCACATGGTGCTGCTGGAATTTGTTACCGCGGCGGGCATTACCCACGG
TATGGACGAGCTGTACAAAGGCGGTGGCGGTAGCGGCGGTGGCGGTAGCGGGCCGGATTGCG
CGTATCACCGTGGTGAACTGGTTTGGTGTACTTTTCATGGCGGTGGCCACCACCACCACCAC
CACTAA

AMINO ACID SEQUENCE (SEQ ID NO: 47)
MRKGEELFTGVVPILVELDGDVNGHKFSVRGEGEGDATNGKLTLKFICTTGKLPVPWPTLVT
TLTYGVQCFARYPDHMKQHDFFKSAMPEGYVQERTISFKDDGTYKTRAEVKFEGDTLVNRIE
LKGIDFKEDGNILGHKLEYNFNSHNVYITADKQKNGIKANFKIRHNVE<u>GGGGSGGGGS</u>**GPDC
AYHRGELVWCTFH**<u>GGGGSGGGGS</u>DGSVQLADHYQQNTPIGDPVLLPDNHYLSTQSVLSKDP
NEKRDHMVLLEFVTAAGITHGMDELYK<u>GGGGSGGGGS</u>GPDCAYHRGELVWCTFH<u>GGG</u>*HHHHH
H*\*

FIG. 1-4

UNDERLINED: LINKER SEQUENCE
BOLD: IgG-BINDING PEPTIDE SEQUENCE
ITALIC: His tag FOR PURIFICATION

[EXAMPLE 2: sfGFP-173 C-2Opt1GSI3]
DNA SEQUENCE (SEQ ID NO: 48)
ATGCGTAAAGGCGAGGAACTGTTCACCGGCGTGGTTCCGATCCTGGTGGAGCTGGACGGTGA
TGTTAACGGCCACAAGTTTAGCGTGCGTGGCGAGGGTGAAGGTGATGCGACCAACGGCAAGC
TGACCCTGAAATTCATTTGCACCACCGGTAAACTGCCGGTGCCGTGGCCGACCCTGGTTACC
ACCCTGACCTACGGTGTGCAGTGCTTTGCGCGTTATCCGGACCACATGAAGCAACACGATTT
CTTTAAAAGCGCGATGCCGGAGGGTTACGTTCAGGAACGTACCATCAGCTTCAAGGACGATG
GTACCTATAAAACCCGTGCGGAAGTGAAGTTTGAAGGTGATACCCTGGTTAACCGTATCGAG
CTGAAGGGCATTGACTTCAAAGAAGATGGTAACATCCTGGGCCACAAGCTGGAATACAACTT
TAACAGCCACAACGTGTATATTACCGCGGACAAGCAGAAGAACGGTATCAAGGCGAACTTTA
AAATTCGTCACAACGTTGAGGGTGGCGGTGGCAGCGGTGGCGGTGGCAGCGGTGGCGGTGGC
AGCGGGCCGGATTGCGCGTACCACCGTGGCGAACTGGTGTGGTGCACCTTTCATGGTGGCGG
TGGCAGCGGTGGCGGTGGCAGCGGTGGCGGTGGCAGCGATGGTAGCGTTCAGCTGGCGGATC
ACTACCAGCAAAACACCCCGATTGGTGATGGTCCGGTGCTGCTGCCGGATAACCACTATCTG
AGCACCCAAAGCGTTCTGAGCAAGGACCCGAACGAGAAACGTGATCACATGGTGCTGCTGGA
ATTTGTTACCGCGGCGGGTATTACCCACGGCATGGACGAGCTGTACAAAGGTGGCGGTGGCA
GCGGTGGCGGTGGCAGCGGTGGCGGTGGCAGCGGCCCGGATTGCGCGTATCACCGTGGCGAA
CTGGTTTGGTGCACCTTCCACGGTGGCGGTCATCACCACCACCACCACTAA

AMINO ACID SEQUENCE (SEQ ID NO: 49)
MRKGEELFTGVVPILVELDGDVNGHKFSVRGEGEGDATNGKLTLKFICTTGKLPVPWPTLVT
TLTYGVQCFARYPDHMKQHDFFKSAMPEGYVQERTISFKDDGTYKTRAEVKFEGDTLVNRIE
LKGIDFKEDGNILGHKLEYNFNSHNVYITADKQKNGIKANFKIRHNVE<u>GGGGSGGGGSGGGG</u>
<u>S</u>GPDCAYHRGELVWCTFH<u>GGGGSGGGGSGGGGS</u>DGSVQLADHYQQNTPIGDGPVLLPDNHYL
STQSVLSKDPNEKRDHMVLLEFVTAAGITHGMDELYK<u>GGGGSGGGGSGGGGS</u>GPDCAYHRGE
LVWCTFH<u>GGG</u>*HHHHHH**

FIG. 1-5

UNDERLINED: LINKER SEQUENCE
BOLD: IgG-BINDING PEPTIDE SEQUENCE
ITALIC: His tag FOR PURIFICATION

[EXAMPLE 5: sfYFP + IgG-BINDING PEPTIDE]
DNA SEQUENCE (SEQ ID NO: 54)
ATGCGTAAAGGCGAGGAACTGTTCACCGGTGTGGTTCCGATCCTGGTGGAGCTGGACGGCGA
TGTTAACGGTCACAAGTTTAGCGTGCGTGGTGAGGGCGAAGGTGACGCGACCAACGGCAAGC
TGACCCTGAAATTCATTTGCACCACCGGTAAACTGCCGGTGCCGTGGCCGACCCTGGTTACC
ACCCTGACCTACGGTGTGCAGTGCTTTGCGCGTTATCCGGACCACATGAAGCAACACGATTT
CTTTAAAAGCGCGATGCCGGAGGGCTACGTTCAGGAACGTACCATCAGCTTCAAGGACGATG
GTACCTATAAACCCGTGCGGAAGTGAAGTTTGAAGGCGATACCCTGGTTAACCGTATCGAG
CTGAAGGGTATTGACTTCAAAGAAGATGGCAACATCCTGGGTCACAAGCTGGAATACAACTT
TAACAGCCACAACGTGTATATTACCGCGGACAAGCAGAAGAACGGTATCAAGGCGAACTTTA
AAATTCGTCACAACGTTGAGGGTGGCGGTGGCAGCGGCGGTGGCGGTAGCGGTCCGGATTGC
GCGTACCACCGTGGTGAACTGGTGTGGTGCACCTTTCATGGCGGTGGCGGTAGCGGCGGTGG
CGGTAGCGATGGTAGCGTTCAGCTGGCGGATCACTACCAGCAAAACACCCCGATTGGTGATG
GTCCGGTGCTGCTGCCGGATAACCACTATCTGAGCTATCAAAGCGTTCTGAGCAAGGACCCG
AACGAGAAACGTGATCACATGGTGCTGCTGGAATTTGTTACCGCGGCGGGCATTACCCACGG
TATGGACGAGCTGTACAAAGGCGGTGGCGGTAGCGGCGGTGGCGGTAGCGGGCCGGATTGCG
CGTATCACCGTGGTGAACTGGTTTGGTGTACTTTTCATGGCGGTGGCCACCACCACCACCAC
CACTAA

AMINO ACID SEQUENCE (SEQ ID NO: 55)
MRKGEELFTGVVPILVELDGDVNGHKFSVRGEGEGDATNGKLTLKFICTTGKLPVPWPTLVT
TLTYGVQCFARYPDHMKQHDFFKSAMPEGYVQERTISFKDDGTYKTRAEVKFEGDTLVNRIE
LKGIDFKEDGNILGHKLEYNFNSHNVYITADKQKNGIKANFKIRHNVEGGGGSGGGGS**GPDC
AYHRGELVWCTFH**GGGGSGGGGSDGSVQLADHYQQNTPIGDGPVLLPDNHYLSYQSVLSKDP
NEKRDHMVLLEFVTAAGITHGMDELYKGGGGSGGGGSGPDCAYHRGELVWCTFHGGG*HHHHH
H**

FIG. 1-6

UNDERLINED: LINKER SEQUENCE
BOLD: IgA-BINDING PEPTIDE SEQUENCE
ITALIC: His tag FOR PURIFICATION

[EXAMPLE 6: sfGFP + IgA-BINDING PEPTIDE]
DNA SEQUENCE (SEQ ID NO: 56)
ATGCGTAAAGGCGAGGAACTGTTCACCGGCGTGGTTCCGATCCTGGTGGAGCTGGACGGTGA
TGTTAACGGCCACAAGTTTAGCGTGCGTGGCGAGGGTGAAGGTGATGCGACCAACGGCAAGC
TGACCCTGAAATTCATTTGCACCACCGGTAAACTGCCGGTGCCGTGGCCGACCCTGGTTACC
ACCCTGACCTACGGTGTGCAGTGCTTTGCGCGTTATCCGGACCACATGAAGCAACACGATTT
CTTTAAAAGCGCGATGCCGGAGGGTTACGTTCAGGAACGTACCATCAGCTTCAAGGACGATG
GCACCTATAAAACCCGTGCGGAAGTGAAGTTTGAAGGTGACACCCTGGTTAACCGTATCGAG
CTGAAGGGCATTGACTTCAAAGAAGATGGTAACATCCTGGGCCACAAGCTGGAGTACAACTT
TAACAGCCACAACGTGTATATTACCGCGGATAAGCAGAAAAACGGTATCAAGGCGAACTTTA
AAATTCGTCACAACGTTGAAGGTGGCGGTGGCAGCGGTGGCGGTGGCAGCCACCAAGTGTGC
CTGAGCTACCGTGGTCGTCCGGTTTGCTTTAGCACCGGTGGCGGTGGCAGCGGTGGCGGTGG
CAGCGATGGCAGCGTTCAGCTGGCGGATCACTACCAGCAAAACACCCCGATTGGTGATGGTC
CGGTGCTGCTGCCGGATAACCACTATCTGAGCACCCAAAGCGTTCTGAGCAAGGACCCGAAC
GAGAAACGTGATCACATGGTGCTGCTGGAATTTGTTACCGCGGCGGGTATTACCCACGGCAT
GGATGAACTGTACAAAGGTGGCGGTGGCAGCGGTGGCGGTGGCAGCCATCAAGTGTGCCTGA
GCTATCGCGGCCGTCCGGTTTGCTTCAGCACCGGTGGCGGTCATCACCACCACCACCACTAA

AMINO ACID SEQUENCE (SEQ ID NO: 57)
MRKGEELFTGVVPILVELDGDVNGHKFSVRGEGEGDATNGKLTLKFICTTGKLPVPWPTLVT
TLTYGVQCFARYPDHMKQHDFFKSAMPEGYVQERTISFKDDGTYKTRAEVKFEGDTLVNRIE
LKGIDFKEDGNILGHKLEYNFNSHNVYITADKQKNGIKANFKIRHNVE<u>GGGGSGGGGS</u>**HQVC
LSYRGRPVCFST**<u>GGGGSGGGGS</u>DGSVQLADHYQQNTPIGDGPVLLPDNHYLSTQSVLSKDPN
EKRDHMVLLEFVTAAGITHGMDELYK<u>GGGGSGGGGS</u>HQVCLSYRGRPVCFST<u>GGG</u>*HHHHHH**

FIG. 1-7

UNDERLINED: LINKER SEQUENCE
BOLD: IgY-BINDING PEPTIDE SEQUENCE
ITALIC: His tag FOR PURIFICATION

[EXAMPLE 6: sfGFP + IgY-BINDING PEPTIDE]
DNA SEQUENCE (SEQ ID NO: 58)
ATGCGTAAAGGCGAGGAACTGTTCACCGGCGTGGTTCCGATCCTGGTGGAGCTGGACGGTGA
TGTTAACGGCCACAAGTTTAGCGTGCGTGGCGAGGGTGAAGGTGATGCGACCAACGGCAAGC
TGACCCTGAAATTCATTTGCACCACCGGTAAACTGCCGGTGCCGTGGCCGACCCTGGTTACC
ACCCTGACCTACGGTGTGCAGTGCTTTGCGCGTTATCCGGACCACATGAAGCAACACGATTT
CTTTAAAAGCGCGATGCCGGAGGGTTACGTTCAGGAACGTACCATCAGCTTCAAGGACGATG
GCACCTATAAACCCGTGCGGAAGTGAAGTTTGAAGGTGACACCCTGGTTAACCGTATCGAG
CTGAAGGGCATTGACTTCAAAGAAGATGGTAACATCCTGGGCCACAAGCTGGAGTACAACTT
TAACAGCCACAACGTGTATATTACCGCGGATAAGCAGAAGAACGGTATCAAGGCGAACTTCA
AAATTCGTCACAACGTGGAAGGTGGCGGTGGCAGCGGTGGCGGTGGCAGCCGTAGCGTGTGC
GTTTGGACCGCGGTTACCGGTTGGGACTGCCGTAACGATGGTGGCGGTGGCAGCGGTGGCGG
TGGCAGCGATGGCAGCGTTCAGCTGGCGGATCACTACCAGCAAAACACCCCGATTGGTGATG
GTCCGGTGCTGCTGCCGGATAACCACTATCTGAGCACCCAAAGCGTTCTGAGCAAGGACCCG
AACGAGAAACGTGATCACATGGTGCTGCTGGAATTTGTTACCGCGGCGGGTATTACCCACGG
CATGGATGAACTGTACAAAGGTGGCGGTGGCAGCGGTGGCGGTGGCAGCCGTAGCGTGTGTG
TGTGGACCGCGGTGACCGGCTGGGATTGCCGCAATGATGGTGGCGGTCATCACCACCACCAC
CACTAA

AMINO ACID SEQUENCE (SEQ ID NO: 59)
MRKGEELFTGVVPILVELDGDVNGHKFSVRGEGEGDATNGKLTLKFICTTGKLPVPWPTLVT
TLTYGVQCFARYPDHMKQHDFFKSAMPEGYVQERTISFKDDGTYKTRAEVKFEGDTLVNRIE
LKGIDFKEDGNILGHKLEYNFNSHNVYITADKQKNGIKANFKIRHNVE<u>GGGGSGGGGS</u>**RSVC
VWTAVTGWDCRND**<u>GGGGSGGGGS</u>DGSVQLADHYQQNTPIGDGPVLLPDNHYLSTQSVLSKDP
NEKRDHMVLLEFVTAAGITHGMDELYK<u>GGGGSGGGGS</u>RSVCVWTAVTGWDCRND<u>GGG</u>*HHHHH
H**\*

FIG. 1-8

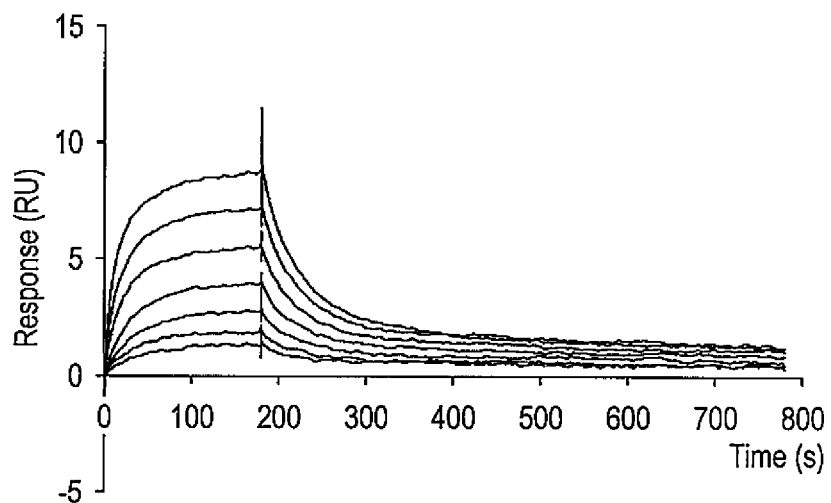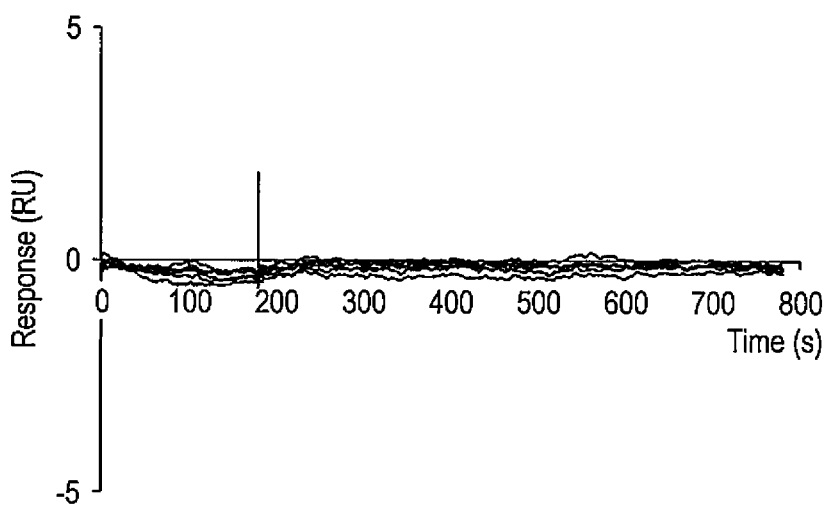
FIG. 2

EXAMPLE 5
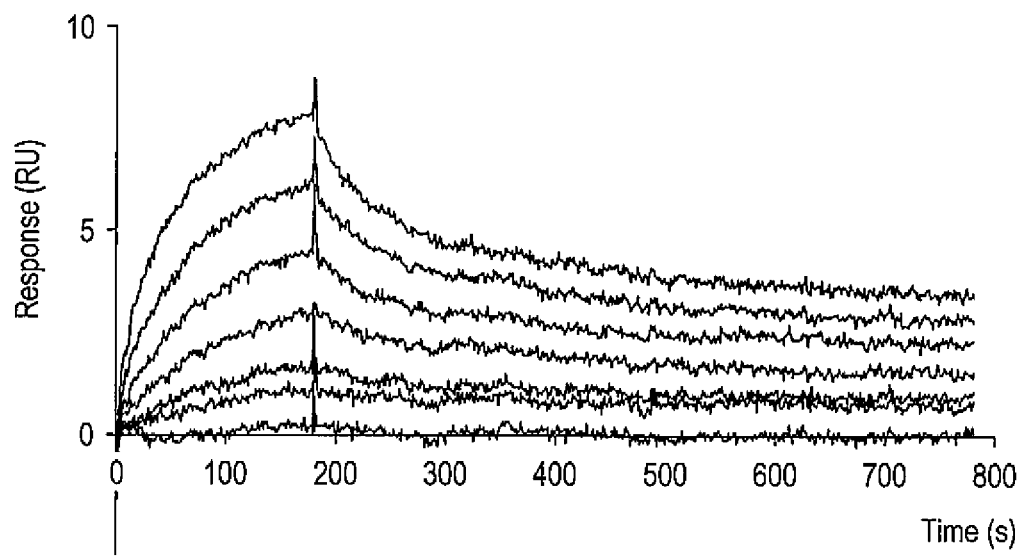
COMPARATIVE EXAMPLE 4
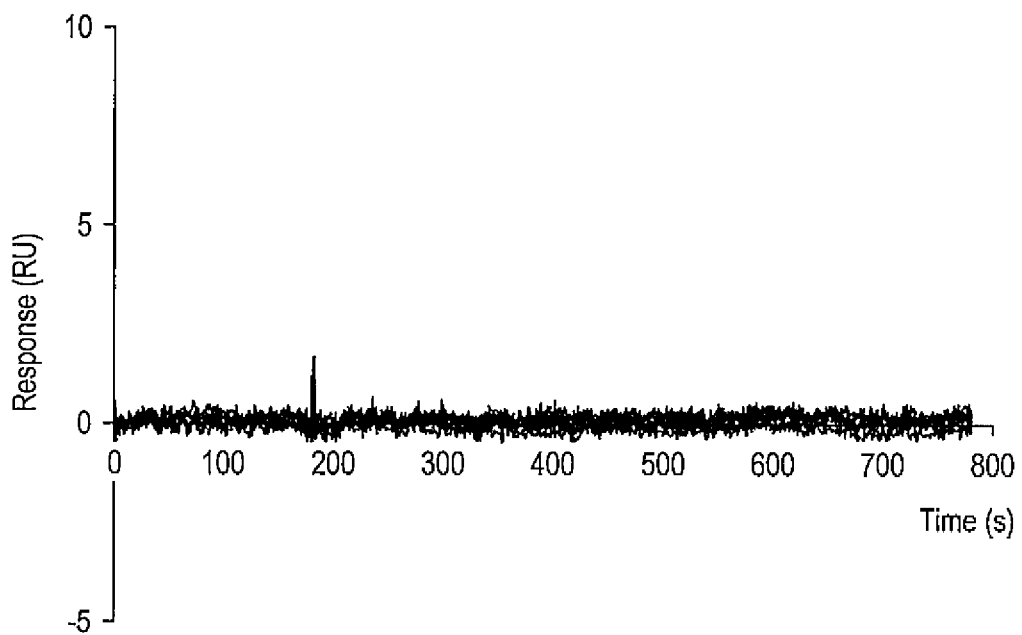
FIG. 6

EXAMPLE 6 (sfGFP + IgA-BINDING PEPTIDE)
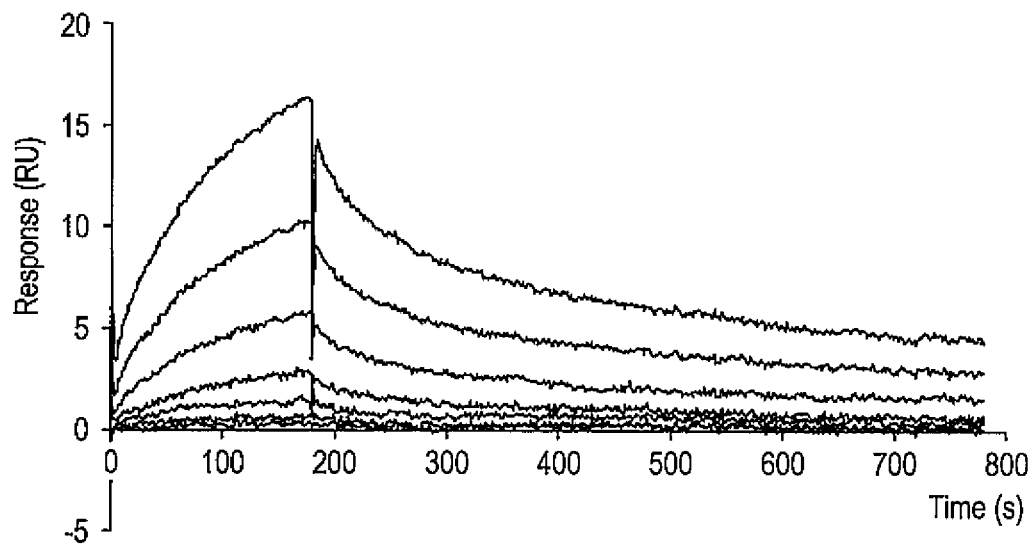
EXAMPLE 6 (sfGFP + IgY-BINDING PEPTIDE)
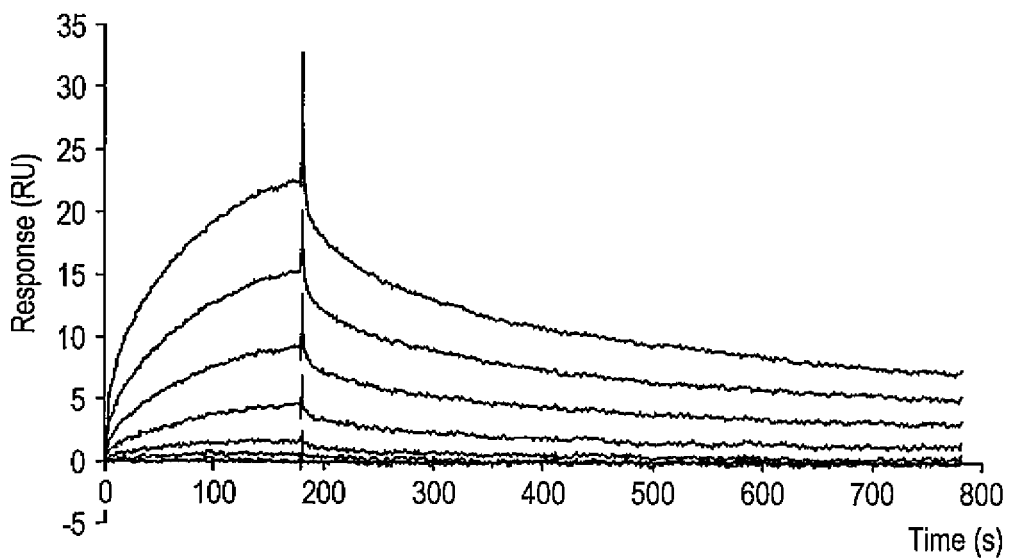
FIG. 7

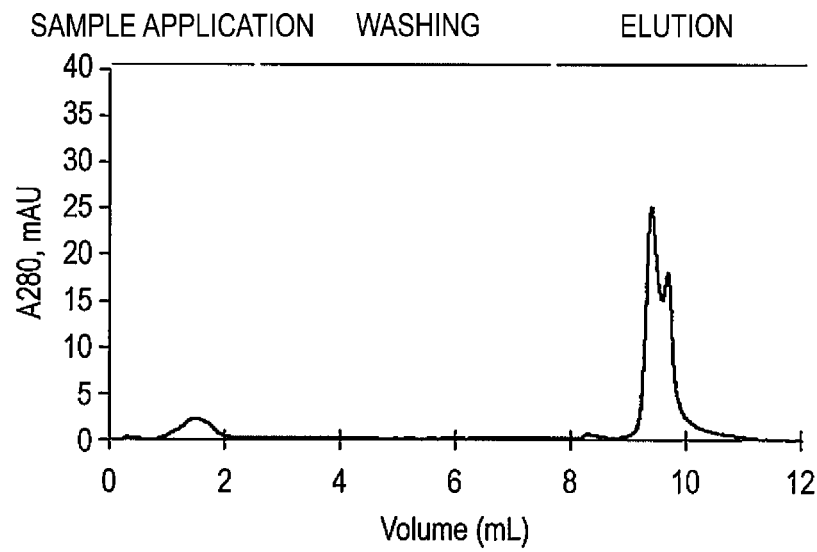
EXAMPLE 7 (sfGFP + IgA-BINDING PEPTIDE)
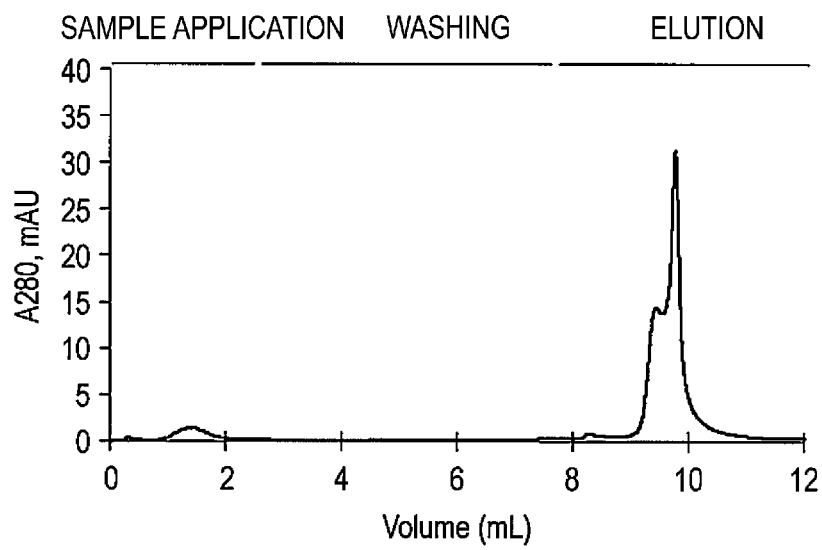
EXAMPLE 7 (sfGFP + IgY-BINDING PEPTIDE)
FIG. 8

PEPTIDE FUSION PROTEIN

REFERENCE TO SEQUENCE LISTING SUBMITTED VIA EFS-WEB

This application includes an electronically submitted sequence listing in .txt format. The .txt file contains a sequence listing entitled "1254_0645PUS1_Sequence Listing.txt" created on Jun. 16, 2022 and is 102,758 bytes in size. The sequence listing contained in this .txt file is part of the specification and is hereby incorporated by reference herein in its entirety.

TECHNICAL FIELD

The present invention relates to, for example, a peptide fusion protein, a solid-phase carrier including the peptide fusion protein, a column for separating a target molecule including the solid-phase carrier, a kit including the solid-phase carrier or column, and a method for purifying the target molecule using the solid-phase carrier or column.

BACKGROUND ART

Proteins including antibodies, such as IgG antibodies, are currently one of the most notable biopharmaceuticals. For example, in recent years, antibody drugs centered on IgG antibodies have come to be used in the pharmaceutical field, and their importance in industrial and pharmaceutical use is increasing. The protein A column plays a central role in the purification of antibodies, and many manufacturers of antibody drugs have introduced purification systems centered on this column. The protein A is produced in large quantities in *Escherichia coli* by a gene recombination method.

On the other hand, the present inventors have previously reported that IgG can be purified by a peptide ligand (Patent Document 1) including a specific sequence cyclized via a disulfide bond, or an IgG-binding peptide in which a sulfide group at a cysteine residue in a peptide is crosslinked via a linker having a specific structure (Patent Document 2).

Although these peptide ligands or IgG-binding peptides can be used as new affinity columns to replace protein A, they are produced by chemical synthesis, so there was a problem that the production cost was higher than that of protein A.

CITATION LIST

Patent Document

Patent Document 1: WO 2013/027796
Patent Document 2: WO 2018/092867

SUMMARY OF INVENTION

Technical Problem

In view of the above circumstances, an object of the present invention is to provide a method by which a peptide having a specific binding capability that can be used for purification of a target molecule including an antibody such as IgG can be produced at a low cost.

Solution to Problem

As a result of diligent research to solve the above problems, it has been found that a peptide having a specific binding capability can be produced as a fusion protein with a protein producible at a high yield in a host cell such as *Escherichia coli* by a low-cost gene recombination method as compared with chemical synthesis. It has been also found that the fusion protein including two or more peptides having a specific binding capability improves binding capability of the fusion protein to the target molecular by the avidity effect, and has a higher affinity because the dissociation rate for target molecular binding is slower than that of a peptide having a specific binding capability alone or a fusion protein including one peptide having a specific binding capability, and thereby the present invention is completed.

That is, the present invention includes the followings.

(1) A peptide fusion protein including one or more peptides having specific binding capability and a scaffold protein, the peptide being inserted into the amino acid sequence of the scaffold protein directly or via a peptide linker, and/or being linked to the N-terminal and/or C-terminal of the scaffold protein.

(2) The peptide fusion protein according to (1), in which the peptide having a specific binding capability is an antibody-binding peptide.

(3) The peptide fusion protein according to (2), in which the antibody-binding peptide is selected from the group consisting of an IgG-binding peptide, an IgA-binding peptide, and an IgY-binding peptide.

(4) The peptide fusion protein according to (3), in which the IgG-binding peptide is a peptide having a cyclic structure.

(5) The peptide fusion protein according to any one of (1) to (4), which includes two or more of the peptides.

(6) The peptide fusion protein according to any one of (1) to (5), in which the scaffold protein is a protein having a β-barrel structure.

(7) The peptide fusion protein according to (6), in which the protein having a β-barrel structure is green fluorescent protein (GFP), red fluorescent protein (DsRed), or a variant thereof.

(8) The peptide fusion protein according to (7), in which the GFP variant is Superfolder GFP or Superfolder yellow fluorescent protein (YFP).

(9) The peptide fusion protein according to any one of (1) to (8), in which the peptide linker includes one or more amino acid sequences: GGGGS (SEQ ID NO: 35).

(10) The peptide fusion protein according to any one of (1) to (9), in which the peptide linker is linked to the N-terminal and/or C-terminal of the peptide.

(11) A solid-phase carrier having the peptide fusion protein described in any one of (1) to (10) immobilized thereon.

(12) The solid-phase carrier according to (11), which has a spacer between the peptide fusion protein and the solid phase.

(13) A column for separating a target molecule including the solid-phase carrier according to (11) or (12).

(14) A method for producing a peptide fusion protein, which includes culturing a cell having a nucleic acid encoding the peptide fusion protein described in any one of (1) to (10).

(15) The method according to (14), wherein the cell is *Escherichia coli*.

This specification includes the disclosure content of JP 2018-145323 A, which is the basis of the priority of the present application.

Advantageous Effects of Invention

According to the present invention, it is possible to reduce the production cost of a peptide having a specific binding capability that can be used for purifying a target molecule.

BRIEF DESCRIPTION OF DRAWINGS

FIG. 1-1 depicts amino acid sequence of the IgG-binding peptide fusion protein prepared in Examples and the DNA sequence encoding the fusion protein.
FIG. 1-2 is a continuation of FIG. 1-1.
FIG. 1-3 is a continuation of FIG. 1-2.
FIG. 1-4 is a continuation of FIG. 1-3.
FIG. 1-5 is a continuation of FIG. 1-4.
FIG. 1-6 is a continuation of FIG. 1-5.
FIG. 1-7 is a continuation of FIG. 1-6.
FIG. 1-8 is a continuation of FIG. 1-7.
FIG. 2 depicts measurement results of the affinity of the IgG-binding peptide fusion protein (sfGFP-C-1Opt1) of Example 1 and the scaffold protein (sfGFP) of Comparative Example 1 to IgG.
FIG. 3 depicts measurement results of the affinity of the IgG-binding peptide divalent fusion protein of Example 2 (SfGFP-N C-2Opt1 GS12, sfGFP-173 C-2Opt1GS12, and sfGFP-173 C-2Opt1GS13) and the peptide of Comparative Example 2 (amino acid sequence: SEQ ID NO: 18) to IgG.
FIG. 4 depicts measurement results of dynamic binding capacity (DBC) of the IgG-binding peptide divalent fusion protein of Example 3 (sfGFP-173 C-2Opt1 GS12) and the peptide of Comparative Example 3 (amino acid sequence: SEQ ID NO: 18).
FIG. 5 depicts a chromatogram relating to the adsorption and desorption of γ-globulin in Example 4 by the column prepared in Example 3.
FIG. 6 depicts measurement results of the affinity of the IgG-binding peptide fusion protein of Example 5 and the scaffold protein (sfYFP) of Comparative Example 4 to IgG.
FIG. 7 depicts measurement results of the affinity of the IgA-binding peptide fusion protein of Example 6 to IgA and measurement results of the affinity of the IgY-binding peptide fusion protein to IgY.
FIG. 8 depicts a chromatogram relating to the adsorption and desorption of IgA by an IgA-binding peptide fusion protein and the adsorption and desorption of IgY by an IgY-binding peptide fusion protein in Example 7.

DESCRIPTION OF EMBODIMENTS

Figure 3:
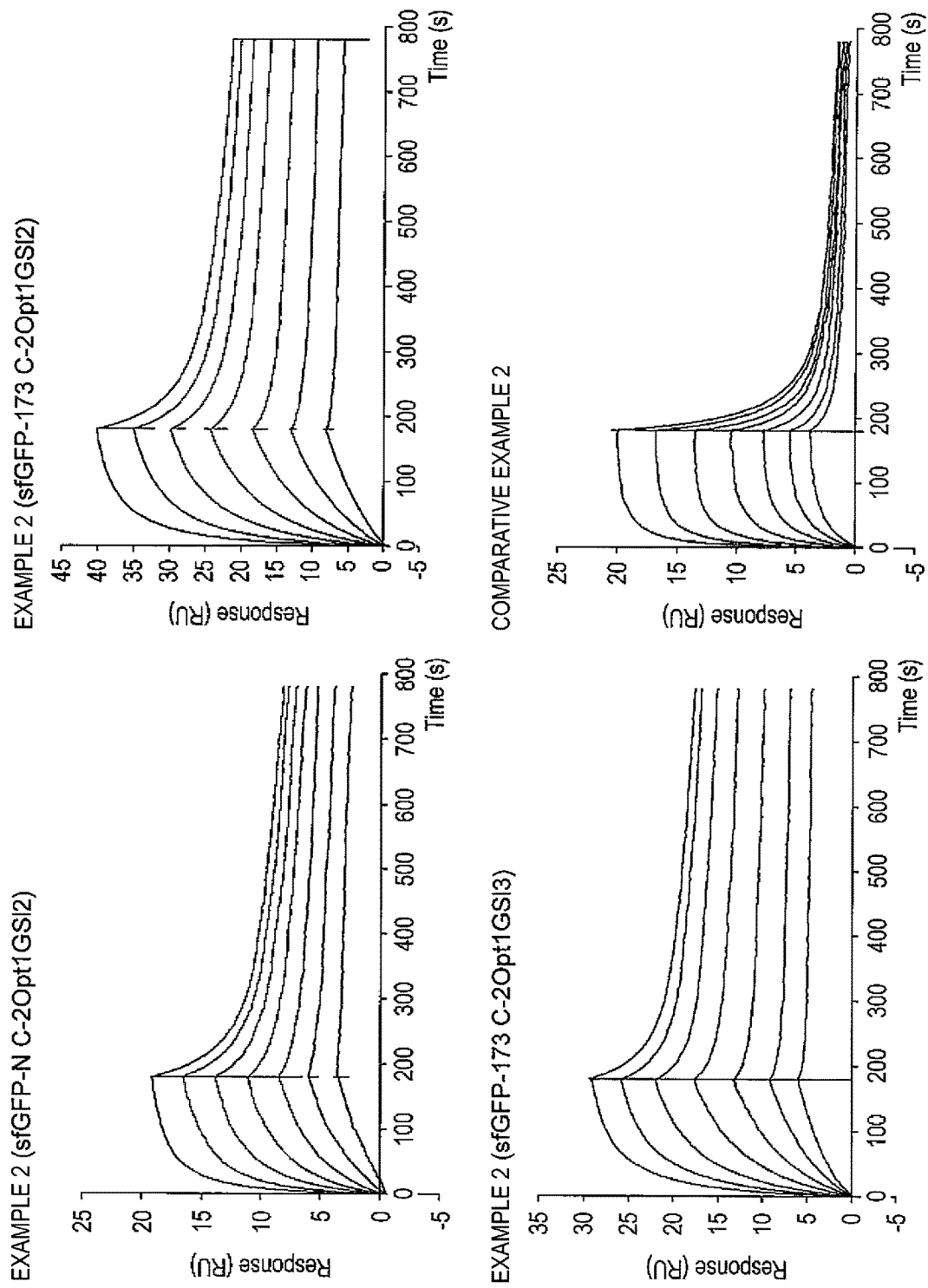

The present invention will be described below in detail.

The peptide fusion protein according to an embodiment of the present invention includes one or more peptides having a specific binding capability and a scaffold protein. The peptide fusion protein according to an embodiment of the present invention can be produced by a gene recombination method instead of chemical synthesis, and can achieve cost reduction.

The peptide having a specific binding capability included in the peptide fusion protein according to an embodiment of the present invention will be described in detail below.

The peptide having a specific binding capability in the present invention refers to a peptide having an amino acid sequence capable of specifically binding to a target molecule. Examples of the specific target molecule include antibody-binding peptides that specifically bind to antibodies (for example, IgG-binding peptides, IgA-binding peptides, and IgY-binding peptides).

The "IgG" or "IgA" used herein refers to IgG or IgA of mammals such as primates such as humans and orangutans, laboratory animals such as rats, mice and rabbits, domestic animals such as pigs, cows, horses, sheep, and goats, and pet animals such as dogs and cats, and preferably refers to human IgG (IgG1, IgG2, IgG3, or IgG4) or IgA. The IgG herein is more preferably human IgG1, IgG2, or IgG4, or rabbit IgG, and particularly preferably human IgG1, IgG2, or IgG4. The "IgY" used herein is a chicken-derived antibody.

The IgG-binding peptide included in the peptide fusion protein according to an embodiment of the present invention binds to the Fc domain of IgG.

In one embodiment, examples of the IgG-binding peptide included in the peptide fusion protein according to an embodiment of the present invention include a peptide having a cyclic structure (cyclic peptide), for example, a peptide including an amino acid sequence consisting of 13 to 17 amino acid residues represented by Formula I:

$$(X_{1-3})\text{-C-}(X_2)\text{-H-}(\text{Xaa1})\text{-G-}(\text{Xaa2})\text{-L-V-W-C-}(X_{1-3}) \quad (I)$$
(SEQ ID NO: 82)

(where,
each X is independently an amino acid residue other than cysteine,
C is a cysteine residue,
H is a histidine residue,
Xaa1 is an arginine residue, a lysine residue, a leucine residue, or an asparagine residue,
G is a glycine residue,
Xaa2 is a glutamic acid residue or an asparagine residue,
L is a leucine residue,
V is a valine residue, and
W is a tryptophan residue),
two cysteine residues outside the peptide being linked thereto via a disulfide bond.

In the above formula, the notation $X_{1-3}$ at the N-terminal or C-terminal means that 1 to 3 independently arbitrary amino acid residues X other than cysteine (C or Cys) are consecutive, and the amino acid residues constituting them are the same or different residues, and $X_{1-3}$ is preferably a sequence of three residues that are not the same. Similarly, $X_2$ also means that two independently arbitrary amino acid residues X other than cysteine (C or Cys) are consecutive, and the amino acid residues constituting them are the same or different residues, and $X_2$ is preferably a sequence of the two consecutive amino acid residues that are not the same.

Peptides represented by Formula I' and Formula I″ in which the amino acid residue X in the amino acid sequence of the peptide of Formula I is further specified are given below.

That is, the peptide represented by Formula I' includes an amino acid sequence consisting of 13 to 17 amino acid residues represented by:

$$(X_{1-3})\text{-C-}(X_1)\text{-Y-H-}(\text{Xaa1})\text{-G-N-L-V-W-C-}(X_{1-3}) \quad (I')$$
(SEQ ID NO: 83)

(where,
each X is independently an amino acid residue other than cysteine,
C is a cysteine residue,
Y is a tyrosine residue,
H is a histidine residue, Xaa1 is an arginine residue, a lysine residue, a leucine residue, or an asparagine residue,
G is a glycine residue,
N is an asparagine residue,
L is a leucine residue,
V is a valine residue, and
W is a tryptophan residue).

The peptide of represented by Formula I″ includes an amino acid sequence consisting of 13 to 17 amino acid residues represented by:

$$(X_{1-3})\text{-C-A-}(X_1)\text{-H-}(Xaa1)\text{-G-E-L-V-W-C-}(X_{1-3}) \quad (I″)$$
(SEQ ID NO: 84)

(where,
each X is independently an amino acid residue other than cysteine,
C is a cysteine residue,
A is an alanine residue,
H is a histidine residue,
Xaa1 is an arginine residue, a lysine residue, a leucine residue, or an asparagine residue,
G is a glycine residue,
E is a glutamic acid residue,
L is a leucine residue,
V is a valine residue, and
W is a tryptophan residue).

Further, a peptide represented by Formula II in which the amino acid residue X in the amino acid sequence of the peptide of Formula I is further specified is given below.

That is, the peptide represented by Formula II includes an amino acid sequence consisting of 13 to 17 amino acid residues represented by:

$$(X_{1-3})\text{-C-}(Xaa3)\text{-}(Xaa4)\text{-H-}(Xaa1)\text{-G-}(Xaa2)\text{-L-V-W-C-}(X_{1-3}) \quad (II)$$
(SEQ ID NO: 85)

(where,
each X is independently an amino acid residue other than cysteine,
C is a cysteine residue,
H is a histidine residue,
Xaa1 is an arginine residue, a lysine residue, a leucine residue, or an asparagine residue,
G is a glycine residue,
Xaa2 is a glutamic acid residue or an asparagine residue,
L is a leucine residue,
V is a valine residue,
W is a tryptophan residue,
Xaa3 is an alanine residue, a serine residue, or a threonine residue, and
Xaa4 is a tyrosine residue or tryptophan residue).

In the amino acid sequences of the peptides of Formula I′, Formula I″, and Formula II above, the 1st and 2nd amino acid residues and the 16th and 17th amino acid residues X from the N-terminal in the case of 17 amino acid residues may be deleted, and such a peptide has a length of 13 amino acids.

The "in the case of 17 amino acid residues" herein is a term for expediently expressing the numbering of 17 residues, which is the longest amino acid length, in the peptide of Formula I as 1st to 17th residues in order from the N-terminal, when amino acid residues of a peptide are represented by amino acid number.

Further, a peptide represented by Formula III in which the amino acid residue X in the amino acid sequence of the peptide of Formula I is further specified is given below.

That is, the peptide represented by Formula III includes an amino acid sequence consisting of 13 to 17 amino acid residues represented by:

$$(X_{1-3})\text{-C-A-Y-H-}(Xaa1)\text{-G-E-L-V-W-C-}(X_{1-3}) \quad (III)$$
(SEQ ID NO: 86)

(where,
each X is independently an amino acid residue other than cysteine,
C is a cysteine residue,
A is an alanine residue,
Y is a tyrosine residue,
H is a histidine residue,
Xaa1 is an arginine residue, a lysine residue, a leucine residue, or an asparagine residue,
G is a glycine residue,
E is a glutamic acid residue,
L is a leucine residue,
V is a valine residue, and
W is a tryptophan residue).

In the amino acid sequence of the peptide of the above Formula III, the 1st and 2nd amino acid residues and the 16th and 17th amino acid residues X from the N-terminal in the case of the 17 amino acid residues may be deleted, and the peptide may consist of 13 amino acids in length.

Further, amino acid residues other than cysteine (C) in the amino acid sequences of the peptides of the above Formulas, that is, each of 1st to 3rd, 5th, 6th, 15th to 17th amino acid residues from the N-terminal in the case of 17 amino acid residues is preferably selected from the followings: 1st amino acid residue=S, G, F, or absent,
2nd amino acid residue=D, G, A, S, P, or absent,
3rd amino acid residue=S, D, T, N, E, or R,
15th amino acid residue=S, T, or D,
16th amino acid residue=H, G, Y, T, N, D, F, or absent,
17th amino acid residue=Y, F, H, M, or absent,
5th amino acid residue=A or T, and
6th amino acid residue=Y or W,
where each uppercase alphabet is a one-letter notation for amino acids.

In addition, a peptide represented by Formula IV in which the amino acid residue X in the amino acid sequence of the peptide of Formula I is further specified is given below.

That is, the peptide represented by Formula IV includes an amino acid sequence consisting of 13 amino acid residues represented by:

$$\text{D-C-}(Xaa3)\text{-}(Xaa4)\text{-H-}(Xaa1)\text{-G-}(Xaa2)\text{-L-V-W-C-T} \quad (IV)$$
(SEQ ID NO: 87)

(where,
D is an aspartic acid residue,
C is a cysteine residue,
H is a histidine residue,
Xaa1 is an arginine residue, a lysine residue, a leucine residue, or an asparagine residue,
G is a glycine residue,
Xaa2 is a glutamic acid residue or an asparagine residue,
L is a leucine residue,
V is a valine residue,
W is a tryptophan residue,
T is a threonine residue,
Xaa3 is an alanine residue or a threonine residue, and
Xaa4 is a tyrosine residue or tryptophan residue).

Some specific examples of peptides of Formula I are listed in 1)-17) below, but it goes without saying that they are not limited to these:

1) DCAYH(Xaa1)GELVWCT, (SEQ ID NO: 1)

2) GPDCAYH(Xaa1)GELVWCTFH, (SEQ ID NO: 2)

3) RCAYH(Xaa1)GELVWCS, (SEQ ID NO: 3)

4) GPRCAYH(Xaa1)GELVWCSFH, (SEQ ID NO: 4)

5) SPDCAYH(Xaa1)GELVWCTFH, (SEQ ID NO: 5)

6) GDDCAYH(Xaa1)GELVWCTFH, (SEQ ID NO: 6)

7) GPSCAYH(Xaa1)GELVWCTFH, (SEQ ID NO: 7)

8) GPDCAYH(Xaa1)GELVWCSFH, (SEQ ID NO: 8)

9) GPDCAYH(Xaa1)GELVWCTHH, (SEQ ID NO: 9)

10) GPDCAYH(Xaa1)GELVWCTFY, (SEQ ID NO: 10)

11) SPDCAYH(Xaa1)GELVWCTFY, (SEQ ID NO: 11)

12) SDDCAYH(Xaa1)GELVWCTFY, (SEQ ID NO: 12)

13) RGNCAYH(Xaa1)GQLVWCTYH, (SEQ ID NO: 13)

14) DCTYH(Xaa1)GNLVWCT, (SEQ ID NO: 14)

15) DCAYH(Xaa1)GNLVWCT, (SEQ ID NO: 15)

16) DCTYH(Xaa1)GELVWCT, and (SEQ ID NO: 16)

17) DCAWH(Xaa1)GELVWCT (SEQ ID NO: 17)

(where Xaa1 is an arginine residue, a lysine residue, a leucine residue, or an asparagine residue).

Preferred specific examples of the peptide of Formula I include:

1) DCAYH(Xaa1)GELVWCT, (SEQ ID NO: 1, where Xaa1 is R)

2) GPDCAYH(Xaa1)GELVWCTFH, and (SEQ ID NO: 2, where Xaa1 is R, L, or K)

4) GPRCAYH(Xaa1)GELVWCSFH, (SEQ ID NO: 4, where Xaa1 is R)

and particularly preferred examples include:

GPDCAYHRGELVWCTFH. (SEQ ID NO: 18)

In one embodiment, the IgG-binding peptide included in the peptide fusion protein according to an embodiment of the present invention includes, as a primary structure in a broad sense, an amino acid sequence consisting of 13 amino acid residues represented by the following Formula V:

D-C-(Xaa2)-(Xaa3)-(Xaa4)-(Xaa1)-G-(Xaa5)-L-(Xaa6)-W-C-T (V) (SEQ ID NO: 88)

(where
D is an aspartic acid residue,
C is a cysteine residue,
G is a glycine residue,
L is a leucine residue,
W is a tryptophan residue,
T is a threonine residue,
Xaa1 is an arginine residue, a lysine residue, a leucine residue, or an asparagine residue,
Xaa2 is an alanine residue, a serine residue, or a threonine residue,
Xaa3 is a tryptophan residue or a tyrosine residue,
Xaa4 is a histidine residue, an arginine residue, a serine residue, or a threonine residue,
Xaa5 is a glutamic acid residue, an asparagine residue, an arginine residue, or an aspartic acid residue, and
Xaa6 is an isoleucine residue or a valine residue), the two cysteine residues outside the peptide being linked thereto via a disulfide bond.

Some specific examples of peptides of Formula V are listed in 18)-29) below, but it goes without saying that they are not limited to these:

18) DCTYT(Xaa1)GNLVWCT, (SEQ ID NO: 19)

19) DCAYT(Xaa1)GNLVWCT, (SEQ ID NO: 20)

20) DCSYT(Xaa1)GNLVWCT, (SEQ ID NO: 21)

21) DCTWT(Xaa1)GNLVWCT, (SEQ ID NO: 22)

22) DCTYH(Xaa1)GNLVWCT, (SEQ ID NO: 23)

23) DCTYR(Xaa1)GNLVWCT, (SEQ ID NO: 24)

24) DCTYS(Xaa1)GNLVWCT, (SEQ ID NO: 25)

25) DCTYT(Xaa1)GNLVWCT, (SEQ ID NO: 26)

26) DCTYT(Xaa1)GELVWCT, (SEQ ID NO: 27)

27) DCTYT(Xaa1)GRLVWCT, (SEQ ID NO: 28)

28) DCTYT(Xaa1)GDLVWCT, and (SEQ ID NO: 29)

29) DCTYT(Xaa1)GNLIWCT (SEQ ID NO: 30)

(where Xaa1 is an arginine residue, a lysine residue, a leucine residue, or an asparagine residue).

As described above, in the IgG-binding peptide of an embodiment of the present invention, Xaa1 is an arginine residue, a lysine residue, a leucine residue, or an asparagine residue, preferably an arginine residue, a lysine residue, or a leucine residue.

The IgG-binding peptide in an embodiment of the present invention may have a binding affinity to human IgG of about 10 times or more, preferably about 50 times or more, and more preferably about 200 times or more as compared with other human immunoglobulins (IgA, IgE, and IgM). The dissociation constant (Kd) for the binding of IgG-binding peptides to human IgG can be determined by surface plasmon resonance spectrometry (for example, using the BIACORE system), and is, for example, less than $1\times10^{-1}$ M, less than $1\times10^{-3}$ M, preferably less than $1\times10^{-4}$ M, and more preferably less than $1\times10^{-5}$ M. The IgG-binding peptide in an embodiment of the present invention can bind to the Fc domain of IgG.

Examples of the IgA-binding peptide in an embodiment of the present invention include IgA-binding peptides described in WO 11/148952 and WO 13/081037, such as the peptide consisting of the amino acid sequence set forth in SEQ ID NO: 50.

Examples of the IgY-binding peptide in an embodiment of the present invention include the IgY-binding peptide described in JP 6245688, such as the peptide consisting of the amino acid sequence set forth in SEQ ID NO: 51.

Further, examples of the peptide having a specific binding capability in an embodiment of the present invention include the peptide described in Table 1 in Yu-Ming Fang et al., Journal of Chromatography A, 1571 (2018) 1-15 (for example, the peptides consisting of the amino acid sequences set forth in SEQ ID NOs: 62-81). The target molecules of the peptides consisting of the amino acid sequences set forth in SEQ ID NOs: 62 to 81 are as follows (SEQ ID NO: of the amino acid sequence of the peptide: target molecule):

SEQ ID NO: 62: Human Serum Albumin (HSA);
SEQ ID NO: 63: IgG;
SEQ ID NO: 64: Tissue plasminogen activator (t-PA);
SEQ ID NO: 65: Anti-GM-CSF Mab;
SEQ ID NO: 66: Human Prostate Specific Antibody (PSA);
SEQ ID NO: 67: Heat shock organizing protein;
SEQ ID NO: 68: Fibrinogen;
SEQ ID NO: 69: IgG;
SEQ ID NO: 70: IgG;
SEQ ID NO: 71: IgG;
SEQ ID NO: 72: α-amylase;
SEQ ID NO: 73: α-lactalbumin;
SEQ ID NO: 74: Staphylococcal enterotoxin B (SEB);
SEQ ID NO: 75: Von Willebrand Factor (vWF);
SEQ ID NO: 76: IgG;
SEQ ID NO: 77: IgG;
SEQ ID NO: 78: IgG;
SEQ ID NO: 79: IgG;
SEQ ID NO: 80: Mouse IgG; and
SEQ ID NO: 81: IgG-Fc (human IgG-Fc).

On the other hand, the scaffold protein included in the peptide fusion protein according to an embodiment of the present invention is not particularly limited as long as it is a protein that fuses to a peptide having a specific binding capability and is suitable for production by a gene recombination method, and examples thereof include a protein producible at a high yield in *Escherichia coli*. Examples of the protein producible at a high yield in *Escherichia coli* include proteins having a β-barrel structure. Proteins having a β-barrel structure form a hydrogen bond network and have high structural stability, and are therefore generally known to be produced at a high yield in *Escherichia coli*.

Examples of the protein having a β-barrel structure include a fluorescent protein having a β-barrel structure, and examples of the fluorescent protein having a β-barrel structure include green fluorescent protein (GFP), red fluorescent protein (DsRed), or a variant thereof.

The cDNA encoding GFP consists of, for example, the nucleotide sequence set forth in SEQ ID NO: 31, and GFP consists of, for example, the amino acid sequence set forth in SEQ ID NO: 32. Examples of the GFP variant include a protein consisting of an amino acid sequence having at least 90%, preferably at least 95%, at least 96%, at least 97%, at least 98%, and at least 99% sequence identity with the amino acid sequence set forth in SEQ ID NO: 32 and having the same fluorescent activity as that of GFP. Specific examples of GFP variant include Superfolder GFP (sfGFP; for example, cDNA: base sequence set forth in SEQ ID NO: 33, amino acid sequence: amino acid sequence set forth in SEQ ID NO: 34), blue fluorescent protein (BFP), cyan fluorescent protein (CFP), yellow fluorescent protein (YFP), sfBFP, sfCFP, and sfYFP (cDNA: base sequence set forth in SEQ ID NO: 52, amino acid sequence: amino acid sequence set forth in SEQ ID NO: 53) (Pedelacq J. D. et al., Nature Biotechnology, 2006, vol. 24, No. 1, pp. 79-88). sfGFP is a GFP variant consisting of an amino acid sequence having the following amino acid substitution (indicated by "amino acid before substitution/amino acid position/amino acid after substitution") in the amino acid sequence set forth in SEQ ID NO: 32: S30R, Y39N, F64L, S65T, F99S, N105T, Y145F, M153T, V163A, I171V, A206V, or S2R and/or S72A in addition to these amino acid substitutions. BFP is a GFP variant consisting of an amino acid sequence having the following amino acid substitutions (indicated by "amino acid before substitution/amino acid position/amino acid after substitution") in the amino acid sequence set forth in SEQ ID NO: 32: Y66H. CFP is a GFP variant consisting of an amino acid sequence having the following amino acid substitutions (indicated by "amino acid before substitution/amino acid position/amino acid after substitution") in the amino acid sequence set forth in SEQ ID NO: 32: Y66W. YFP is a GFP variant consisting of an amino acid sequence having the following amino acid substitutions (indicated by "amino acid before substitution/amino acid position/amino acid after substitution") in the amino acid sequence set forth in SEQ ID NO: 32: T203Y. sfBFP is a GFP variant consisting of the amino acid sequences having the amino acid substitutions of sfGFP and BFP described above in the amino acid sequence set forth in SEQ ID NO: 32. sfCFP is a GFP variant consisting of the amino acid sequences having the amino acid substitutions of sfGFP and CFP described above in the amino acid sequence set forth in SEQ ID NO: 32. sfYFP is a GFP variant consisting of the amino acid sequences having the amino acid substitutions of sfGFP and YFP described above in the amino acid sequence set forth in SEQ ID NO: 32.

Examples of the fluorescent protein having a β-barrel structure include the above-described variant of yellow fluorescent protein (YFP), and examples of the YFP variant include a protein having an amino acid sequence having at least 90%, preferably at least 95%, at least 96%, at least 97%, at least 98%, and at least 99% sequence identity with the amino acid sequence of YFP described above, and having the same fluorescent activity as that of YFP.

Further, examples of the fluorescent protein having a β-barrel structure include a red fluorescent protein (DsRed) or a variant thereof. The cDNA encoding DsRed includes, for example, the nucleotide sequence set forth in SEQ ID NO: 60, and DsRed includes, for example, the amino acid sequence set forth in SEQ ID NO: 61. Examples of the DsRed variant include a protein consisting of an amino acid sequence having at least 90%, preferably at least 95%, at least 96%, at least 97%, at least 98%, and at least 99% sequence identity with the amino acid sequence set forth in SEQ ID NO: 61, and having the same fluorescent activity as that of DsRed.

The peptide fusion protein according to an embodiment of the present invention includes the above-described peptide having a specific binding capability and scaffold protein as the fusion protein. In particular, the peptide fusion protein according to an embodiment of the present invention includes two or more (for example, from 2 to 5, preferably from 2 to 3) peptides having the same or different specific binding capabilities, and thus improves binding capability of the fusion protein to the target molecular due to the avidity effect, and has a slower dissociation rate for target molecular binding and a higher affinity than those of a peptide having a specific binding capability alone or a fusion protein including one peptide having a specific binding capability. Further, as described above, the peptide fusion protein according to an embodiment of the present invention has a high affinity to the target molecule because it includes two or more peptides having a specific binding capability, whereby its immobilization amount on the solid-phase carrier or the column for separating a target molecule described below can be reduced, and the cost can be reduced.

In the peptide fusion protein according to an embodiment of the present invention, the peptide having a specific binding capability is inserted into the amino acid sequence of the scaffold protein directly or via a peptide linker, and/or linked to the N-terminal and/or C-terminal of the scaffold protein.

In particular, when the scaffold protein is a GFP or a variant thereof, the peptide having a specific binding capability is preferably inserted, directly or via a peptide linker, between the first and second amino acids, in the 155th to 160th amino acid sequences (particularly between the 156th and 157th amino acids) and/or in the 170th to 176th amino acid sequences (particularly between the 172nd and 173rd amino acid ands) in the amino acid sequence set forth in SEQ ID NO: 32 of GFP or the corresponding amino acid sequence of the GFP variant, and/or linked to the C-terminal of GFP or a variant thereof. The position number (residue number) of the amino acid is the position number of the amino acid in the amino acid sequence set forth in SEQ ID NO: 32 of GFP. Each amino acid position in the amino acid sequence of the GFP variant corresponding to each amino acid position in the amino acid sequence set forth in SEQ ID NO: 32 of GFP can be determined, for example, by an alignment comparison between the amino acid sequence set forth in SEQ ID NO: 32 of GFP and the amino acid sequence of the GFP variant by a known method. This also applies to the following YFP or its variant and DsRed or its variant.

When the scaffold protein is YFP or a variant thereof, similarly to GFP or its variants, the peptide having a specific binding capability is preferably inserted, directly or via a peptide linker, between the first and second amino acids, in the 155th to 160th amino acid sequences (particularly between the 156th and 157th amino acids) and/or in the 170th to 176th amino acid sequences (particularly between the 172nd and 173rd amino acids) in the amino acid sequence of YFP having the amino acid substitution T203Y in the amino acid sequence set forth in SEQ ID NO: 32 or the corresponding amino acid sequence of the YFP variant, and/or linked to the C-terminal of YFP or a variant thereof.

Further, when the scaffold protein is DsRed or a variant thereof, from the structural comparison between GFP and DsRed, the peptide having a specific binding capability is preferably inserted, directly or via a peptide linker, between the first amino acid and the second amino acid, in the 153rd to 158th amino acid sequences (particularly between the 154th and 155th amino acids) and/or in the 166th to 172nd amino acid sequences (particularly between the 168th and 169th amino acids) in the amino acid sequence set forth in SEQ ID NO: 61 of DsRed or the corresponding amino acid sequence of the DsRed variant, and/or linked to the C-terminal of DsRed or a variant thereof.

Examples of the peptide linker include a linker including one or more (for example, two or three) amino acid sequences: GGGGS (SEQ ID NO: 35). The peptide linker can be linked to the N-terminal and/or C-terminal of the peptide having a specific binding capability in the peptide fusion protein according to an embodiment of the present invention.

The peptide fusion protein according to an embodiment of the present invention may further include a tag. Examples of the tag include a peptide tag for protein isolation/purification such as a histidine tag (amino acid sequence: HHHHHH (SEQ ID NO: 37)), FLAG-tag (amino acid sequence: DYKDDDDK (SEQ ID NO: 38)), and Strep-tag (amino acid sequence: WSHPQFEK (SEQ ID NO: 39)). The tag can be linked, for example, to the N-terminal and/or C-terminal of the peptide fusion protein according to an embodiment of the present invention, directly or via a peptide linker (e.g., amino acid sequence: GGG (SEQ ID NO: 36)).

The peptide fusion protein according to an embodiment of the present invention can be produced by a gene recombination method. Specifically, the peptide fusion protein can be produced by culturing a cell having a nucleic acid (DNA (for example, cDNA) or RNA (for example, mRNA)) encoding the peptide fusion protein according to an embodiment of the present invention.

Production by the gene recombination method can be carried out, for example, by a method including inserting a DNA (gene) encoding the peptide fusion protein according to an embodiment of the present invention into an appropriate expression vector, introducing the vector into an appropriate host cell, culturing the obtained cell (transformant), and collecting the target peptide fusion protein in the cell or from extracellular fluid.

The DNA encoding the peptide fusion protein according to an embodiment of the present invention can be obtained by, for example, linking DNAs encoding the components (the peptide having a specific binding capability, scaffold protein, peptide linker, and peptide tag) synthesized by the PCR method using appropriate primers with a ligase by an ordinary method. When the peptide having a specific binding capability is inserted into the amino acid sequence of the scaffold protein, a DNA encoding the peptide fusion protein according to an embodiment of the present invention can be obtained by, for example, synthesizing two DNA fragments encoding the N-terminal fragment and the C-terminal fragment of the scaffold protein before and after the insertion position by the PCR method using an appropriate primer, and binding them with the DNA encoding the components (for example, the peptide having a specific binding capability, peptide linker, and peptide tag) with ligase by an ordinary method.

Alternatively, the DNA encoding the peptide fusion protein according to an embodiment of the present invention may be chemically synthesized by an ordinary method.

Examples of the vector include, but are not limited to, vectors such as plasmids, phages, cosmids, phagemids, and viruses. Examples of the plasmid vector include, but are not limited to, *Escherichia coli*-derived plasmids (for example, pET17b, pET22b (+), pBR322, pBR325, pUC118, pUC119, pUC18, pUC19, and pBluescript), *Bacillus subtilis*-derived plasmids (for example, pUB110 and pTP5), and yeast-derived plasmids (for example, YEp13 and YCp50). Examples of the phage vector include, but are not limited to, T7 phage display vectors (for example, T7Select10-3b, T7Select1-1b, T7Select1-2a, T7Select1-2b, and T7Select1-2c (Novagen)), and λ, phage vectors (Charon4A, Charon21A, EMBL3, EMBL4, λgt10, λgt11, λZAP, and λZAPII). Examples of the virus vector include, but are not limited to, animal viruses such as retrovirus, adenovirus, adeno-associated virus, vaccinia virus, and Sendai virus, and insect viruses such as baculovirus. Examples of the cosmid vector include, but are not limited to, Lorist6, Charomid 9-20, and Charomid 9-42. Examples of known phagemid vector include, but are not limited to, pSKAN, pBluescript, pBK, and pComb3H.

The vector may include a regulatory sequence such that the target DNA can be expressed, a selectable marker for selecting a vector including the target DNA, a multicloning site for inserting the target DNA, and the like. Such regulatory sequences include promoters, enhancers, terminators, S-D sequences or ribosome binding sites, replication origins, poly A sites, and the like. Further, as the selectable marker, for example, an ampicillin resistance gene, a neomycin resistance gene, a kanamycin resistance gene, and a dihydrofolate reductase gene may be used.

Examples of the host cell for introducing a vector include bacteria such as *Escherichia coli* and *Bacillus subtilis*, yeast cells, insect cells, animal cells (for example, mammalian cells), and plant cells. In the present invention, it is preferable to use a protein producible at a high level in *Escherichia coli* (for example, GFP, YFP, DsRed, or a variant thereof) as the scaffold protein included in the peptide fusion protein according to an embodiment of the present invention, and thus it is preferable to use *Escherichia coli* as a host cell. Examples of the transformation or transfection into these host cells include a calcium phosphate method, a electroporation method, a lipofection method, a particle cancer method, and a PEG method.

Culturing transformed cells is carried out according to an ordinary method used for culturing host cells. For example, a culture solution for a microorganism such as *Escherichia coli* or yeast cells includes a carbon source, a nitrogen source, inorganic salts and the like that can be assimilated by the host microorganism. To facilitate the collection of the peptide fusion protein according to an embodiment of the present invention, it is preferable to secrete the peptide fusion protein produced by expression extracellularly. This can be done by binding a DNA encoding a peptide sequence that allows the secretion of the peptide fusion protein from the cell to the 5' terminal of the DNA encoding the fusion protein. The fusion peptide transferred to the cell membrane is cleaved by a signal peptidase, and the target peptide fusion protein is secreted and released into the medium. Alternatively, the peptide fusion protein accumulated in the cell can be collected. In this case, the cells are physically or chemically destroyed and protein purification techniques are used to collect the target peptide fusion protein.

The produced peptide fusion protein can be collected or purified by an ordinary method such as chromatography such as gel filtration chromatography, ion exchange column chromatography, affinity chromatography, reverse phase column chromatography, or HPLC, ammonium sulfate fraction, ultrafiltration, or immunoadsorption. As described above, when the peptide fusion protein according to an embodiment of the present invention has a purification tag such as a histidine tag, the peptide fusion protein can be purified from cells or a medium using the purification tag. For example, when the peptide fusion protein has a histidine tag, the peptide fusion protein can be purified by immobilized metal affinity chromatography (IMAC).

The present invention also relates to a solid-phase carrier having the peptide fusion protein according to an embodiment of the present invention immobilized. Examples of the "solid-phase carrier" include, but are not limited to, inorganic carriers such as glass beads and silica gels; organic carriers consisting of synthetic polymers such as a crosslinked polyvinyl alcohol, a crosslinked polyacrylate, a crosslinked polyacrylamide, and a crosslinked polystyrene, and polysaccharides such as crystalline cellulose, crosslinked cellulose, crosslinked agarose, and crosslinked dextran; and composite carriers such as organic-organic and organic-inorganic ones obtained by combining them. Among these, hydrophilic carriers are preferable because they have relatively little non-specific adsorption and good selectivity for the peptide fusion protein. The hydrophilic carrier as used herein refers to a carrier having a contact angle with water of 60 degrees or less as measured when a compound constituting the carrier is formed into a flat plate shape. Typical examples of the carrier include carriers made of polysaccharides such as cellulose, chitosan, and dextran; polyvinyl alcohol; a saponified product of an ethylene-vinyl acetate copolymer; polyacrylamide; polyacrylic acid; polymethacrylic acid; methyl polymethacrylate; polyacrylic acid-grafted polyethylene; polyacrylamide-grafted polyethylene; and glass.

The form of the solid-phase carrier may be selected from any form such as a bead-like, fibrous, particle strip, film-like (including hollow fiber), or gel-like from. A carrier in the form of beads is particularly preferably used because of ease of preparing a carrier having a specific exclusion limit molecular weight. A carrier in the form of beads with an average particle size of 10 to 2500 μm is easy to use, and the range of 25 μm to 800 μm is particularly preferable from the viewpoint of ease of peptide fusion protein immobilization reaction. Specific examples of the solid-phase carrier include magnetic beads, glass beads, polystyrene beads, silica gel beads, and polysaccharide beads.

Further, the presence of a functional group that can be used for the immobilization reaction of the peptide fusion protein on the surface of the solid-phase carrier is convenient for immobilization of the peptide fusion protein. Representative examples of the functional group include a hydroxyl group, an amino group, an aldehyde group, a carboxyl group, a thiol group, a silanol group, an epoxy group, a succinylimide group, an N-hydroxysuccinimide group, an acid anhydride group, and an iodoacetyl group.

The solid-phase carrier may be a commercially available product. Examples of the commercially available carriers include GCL2000 and GC700, which are porous cellulose gels, Sephacryl S-1000 in which allyl dextran and methylene bisacrylamide are covalently crosslinked, Toyopearl, which is an acrylate-based carrier, Sepharose CL4B, which is an agarose-based cross-linked carrier, Eupergit C250L, which is an epoxy group-activated polymethacrylamide, and NHS-activated prepack column including a Sepharose carrier activated with an NHS group. However, the present embodiment is not limited to these carriers and activated carriers.

The solid-phase carriers described above may be used alone, or any two or more may be mixed. In addition, the solid-phase carrier preferably has a large surface area and has a large number of pores having an appropriate size, that is, is preferably porous, in view of the purpose and method of use thereof.

Immobilization of the peptide fusion protein according to an embodiment of the present invention on a solid-phase carrier can be carried out by a method well known to those skilled in the art, for example, physical adsorption, covalent bonding, or ionic bonding. Immobilization is preferably carried out, for example, by covalently bonding the N-terminal amino group of the peptide fusion protein to the solid-phase carrier directly or via a spacer. It is more preferable to immobilize the peptide fusion protein via a hydrophilic spacer to improve the separation efficiency by reducing the steric hindrance of the peptide fusion protein and further suppress the non-specific binding. The hydrophilic spacer is not particularly limited, but for example, is preferably a derivative of polyalkylene oxide in which both ends are substituted with a carboxyl group, an amino group, an aldehyde group, or an epoxy group.

The method and conditions for immobilization of the peptide fusion protein introduced onto the solid-phase carrier and the organic compound used as the spacer are not particularly limited, and examples thereof include usual methods for immobilizing a protein or peptide onto a carrier is used. Examples of the method include: a method of activating a carrier by reacting it with, for example, a compound including an amino group, a compound including a N-hydroxysuccinimidyl group, cyanide bromide, epichlorohydrin, diglycidyl ether, tosyl chloride, tresyl chloride, or hydrazine (to change functional groups originally possessed by the carrier to functional groups that are more reactive with the peptide fusion protein), and reacting the peptide fusion protein with the carrier for immobilization; and a method of adding a condensation reagent such as carbodiimide or a reagent having multiple functional groups in the molecule such as glutaraldehyde to a system in which the carrier and the peptide fusion protein are present, and condensing and cross-linking the carrier and peptide fusion protein for immobilization. It is more preferable to apply an immobilization method in which the peptide fusion protein is not more easily desorbed from the solid-phase carrier during sterilization or utilization of the solid-phase carrier.

The solid-phase carrier including the peptide fusion protein according to an embodiment of the present invention may be filled in a chromatography column or the like and used for purifying or separating the target molecule.

The present invention also relates to a column for separating a target molecule comprising the above solid-phase carrier having the peptide fusion protein immobilized thereon.

The column for separating a target molecule includes a column such as a chromatography column and a high performance liquid chromatography (HPLC) column for purifying or separating the target molecule. The size of the column is not particularly limited, and may be changed according to applications such as analysis, purification, and preparative use, the amount to be applied (loaded) or injected, the length or inner diameter of the column, and the like. The material of the column may be one that is usually used for a metal, plastic, glass column.

The above-described column can be produced by densely filling the column with the above-mentioned solid-phase carrier (which may be in a dry state or a wet state) according to an embodiment of the present invention.

The present invention also relates to a kit for purifying a target molecule, which includes the above solid-phase carrier having the peptide fusion protein immobilized thereon, or the column for separating a target molecule including the solid-phase carrier.

In addition to the solid-phase carrier or the column for separating a target molecule, the kit may include at least one of an instruction manual describing the analysis procedure and purification procedure of the target molecule, a reagent and a buffer necessary for purification, or a column for filling the solid-phase carrier.

The present invention also relates to a method for purifying a target molecule, which includes binding the target molecule to the solid-phase carrier or the column for separating the target molecule, and eluting the bound target molecule to collect the target molecule.

The binding may be performed by a method known to those skilled in the art. For example, the solid-phase carrier or the column for separating a target molecule is equilibrated with an appropriate buffer, a solution including the target molecule is applied at 0° C. to room temperature (preferably at a low temperature of 0° C. to about 10° C., more preferably about 4° C.), and the target molecule is bound to the peptide fusion protein on the solid-phase carrier. For example, when separating a target molecule in serum, the binding may be carried out by applying a buffer having a neutral pH (for example, pH 6.0 to 7.5) to the column.

The elution may also be performed by a method known to those skilled in the art. For example, a buffer (for example, 0.2 M glycine-HCl buffer or 20 mM citrate buffer with pH 3.5 to pH 2.5 including 0.3 M NaCl) having an acidic pH (for example, pH 2 to 4) may be flowed through the column, or the peptide fusion protein may be used to elute by competitive elution. In particular, elution is preferably performed with an acid from the viewpoint of cost. In this case, the solid-phase carrier or column is washed with an alkaline solution such as a sodium hydroxide solution, a potassium hydroxide solution, or a potassium hydroxide solution (for example, 0.1 M sodium hydroxide solution) to regenerate the solid-phase carrier or column, and used again in the binding. The degree of alkalinity of the solution can be easily determined by those skilled in the art. Accordingly, the method for purifying a target molecule according to an embodiment of the present invention may optionally include regenerating the solid-phase carrier or the column by washing it with an alkaline solution.

Whether the target molecule has been collected can be determined by, for example, confirmation of the molecular weight by electrophoresis and optionally subsequent Western blotting using an anti-target molecule antibody. For example, electrophoresis may be performed by SDS-PAGE with a 5-20% acrylamide gel, and in Western blotting, the migrated protein is transferred to a PVDF membrane, blocked with skim milk, and then detected with an anti-target molecule goat antibody and an HRP-labeled anti-goat IgG mouse antibody.

The method for purifying a target molecule according to an embodiment of the present invention is useful for obtaining a target molecule-rich fraction in purifying a target molecule from the target molecule-containing products produced by various methods. Therefore, it is preferable to use the method for purifying a target molecule according to an embodiment of the present invention in column chromatography such as affinity chromatography and HPLC. For purifying the target molecule, in addition to such a chromatography method, related-art purification techniques for proteins such as gel filtration chromatography, ion exchange column chromatography, and reverse phase column chromatography, ammonium sulfate fractionation, ultrafiltration, and others may be combined as appropriate.

EXAMPLES

Hereinafter, the present invention will be described in more detail based on examples, but the technical scope of the present invention is not limited to these Examples.

FIG. 1 depicts the amino acid sequences of the IgG-binding peptide fusion protein, IgA-binding peptide fusion protein, and IgY-binding peptide fusion protein prepared in this example, and the DNA sequence encoding the fusion protein.

Example 1: Affinity Measurement of IgG-Binding Peptide Fusion Protein

A DNA (SEQ ID NO: 42) encoding a protein (sfGFP-C-1Opt1) consisting of the amino acid sequence represented by SEQ ID NO: 43 was inserted into the NdeI/HindIII site of the pET17b vector to construct an expression plasmid.

Using the constructed expression plasmid, *Escherichia coli* strain SHuffle T7 Express (New England Biolabs) or OverExpress C43 (DE3) (Lucigen) was transformed and cultured on an LB agar plate (50 µg/mL ampicillin). The obtained single colony was precultured overnight in 10 mL of LB medium (50 µg/mL ampicillin, 0.5% glucose) at 37° C. and 200 rpm. The obtained culture solution was inoculated in 500 mL of a new LB medium (50 µg/mL ampicillin) such that $OD_{600=0.1}$, and main culture was started under the conditions of 37° C. and 200 rpm. 1 mM IPTG (Isopropanol β-D-thiogalactopylanoside) was added at $OD_{600}$=0.5 to 1.5, and expression induction was performed overnight at 25° C. and 200 rpm. The obtained culture broth was centrifuged (20 kxg, 4° C., 5 minutes), and protein-expressing *Escherichia coli* was collected.

The collected cells were lysed by treatment with Bug Buster (Merck Millipore). After obtaining a soluble fraction by centrifugation, the target protein including a histidine tag was purified using HiTrap TALON crude (GE Healthcare). The solvent of the purified protein solution was replaced with a storage solution (25 mM HEPES, 150 mM NaCl, pH 7.4) and used in the analytical experiment described later.

The affinity analysis was performed by the following method. First, a solution containing equal amounts of 0.4 M EDC (1-ethyl-3-(3-dimethylaminopropyl)-carbodiimide) and 0.1 M sulfo-NHS (sulfo-N-hydroxysuccinimide)) was injected at a flow rate of 10 µl/ml onto a CMS sensor chip set in BIAcore T200 (GE healthcare), thereby activating the sensor chip. Then, under the condition of pH 5.5 (10 mM Na acetate), the purified protein (sfGFP-C-1Opt1) described above was immobilized onto the sensor chip. For the measurement, HBS-EP buffer (10 mM HEPES, 150 mM NaCl, 0.005% Tween 20, 3 mM EDTA, pH 7.4) was used, and the binding reaction was monitored by injecting 6.25, 12.5, 25, 50, 100, 200, and 400 nM human IgG for 180 seconds at a flow rate of 50 µl/ml. For measuring the dissociation reaction, only the buffer was injected for 600 seconds. The analysis of interaction parameters was performed using BIA evalution T100 software.

Comparative Example 1

As Comparative Example 1, a scaffold protein (sfGFP having a His tag; DNA sequence: SEQ ID NO: 40, amino acid sequence: SEQ ID NO: 41) to which an IgG-binding peptide was not fused was expressed and purified in the same manner as in Example 1, and affinity was measured.

FIG. 2 depicts the results of Example 1 and Comparative Example 1. As shown in FIG. 2, it was found that the peptide fused to the scaffold protein has an IgG binding function and can be used for IgG purification.

Example 2: Affinity Measurement of IgG-Binding Peptide Divalent Fusion Protein Proteins including two IgG-binding peptides, each consisting of the amino acid sequences represented by SEQ ID NO: 45, SEQ ID NO: 47, and SEQ ID NO: 49 (sfGFP-N C-2Opt1GS12 (DNA sequence: SEQ ID NO: 44), sfGFP-173 C-2Opt1 GS12 (DNA sequence: SEQ ID NO: 46), and sfGFP-173 C-2Opt1GS13 (DNA sequence: SEQ ID NO: 48)) were expressed and purified by the same method as in Example 1, and the affinity was measured.

Comparative Example 2

As Comparative Example 2, the affinity measurement of the peptide (amino acid sequence: SEQ ID NO: 18) prepared by chemical synthesis was carried out in the same manner as in Example 1.

FIG. 3 depicts the results of Example 2 and Comparative Example 2, and the interaction parameters are listed in Table 1.

TABLE 1

| | IgG-binding peptide fusion protein | $k_{on}$ (M$^{-1}$s$^{-1}$) | $k_{off}$ (s$^{-1}$) | $K_D$ (M) |
|---|---|---|---|---|
| Comparative Example 2 | | $3.3 \times 10^5$ | $4.8 \times 10^{-3}$ | $1.4 \times 10^{-8}$ |
| Example 1 | sfGFP-C-1Opt1 | $7.2 \times 10^5$ | $2.1 \times 10^{-3}$ | $2.8 \times 10^{-8}$ |
| Example 2 | sfGFP-N C-2Opt1GS12 | $3.6 \times 10^5$ | $8.0 \times 10^{-4}$ | $2.2 \times 10^{-9}$ |
| Example 2 | sfGFP-173 C2Opt1GSl2 | $3.1 \times 10^5$ | $5.4 \times 10^{-4}$ | $1.8 \times 10^{-9}$ |
| Example 2 | sfGFP-173 C-2Opt1GSl3 | $1.9 \times 10^5$ | $4.8 \times 10^{-4}$ | $5.4 \times 10^{-9}$ |

As shown in FIG. 3 and Table 1, it was revealed that the peptide divalent fusion protein has a slower dissociation rate and higher affinity than those of the peptide alone or the peptide monovalent fusion protein.

Example 3: Dynamic Binding Capacity (DBC) Measurement

To examine whether the IgG-binding peptide divalent fusion protein can be used as an affinity ligand for human antibody purification, the protein prepared in Example 2 (sfGFP-173 C-2Opt1 GS12) was immobilized on an NHS-activated prepack column (GE Healthcare), and the adsorption performance was evaluated. The protein-immobilized column was prepared by the following method. A syringe was used to feed the solution.

5 mL of 1 mM hydrochloric acid was fed to a NHS-activated prepack column with a volume of 1 mL to remove the isopropanol solution in the column. Then, 1 mL of a coupling solution (200 mM carbonate buffer, 500 mM sodium chloride, pH 8.3) containing 7.3 mg of an IgG-binding peptide fusion protein was fed and immobilized at room temperature for 1 hour. The unreacted NHS ester was blocked by adding tris-hydroxymethylaminomethane.

Finally, 5 mL of an adsorption solution (20 mM phosphate buffer, 150 mM sodium chloride, pH 7.4) was fed and used for DBC measurement.

The DBC measurement was performed using a liquid chromatography instrument AKTAexplore (GE Healthcare). After equilibrating the prepared column with an adsorption solution, 1 mg/mL human serum-derived γ-globulin (Sigma-Aldrich) dissolved in the adsorption solution was fed at a flow rate of 1 mL/min. The DBC was determined from the amount of the sample fed until the value of an absorbance at 280 nm excluding the non-adsorbed component reached 10% of the absorbance of the entire sample.

Comparative Example 3

As Comparative Example 3, a column in which a peptide (amino acid sequence: SEQ ID NO: 18) prepared by chemical synthesis was immobilized in an equimolar amount (0.5 mg) with that of the protein of Example 3 was prepared, and DBC measurement was carried out.

Figure 4:
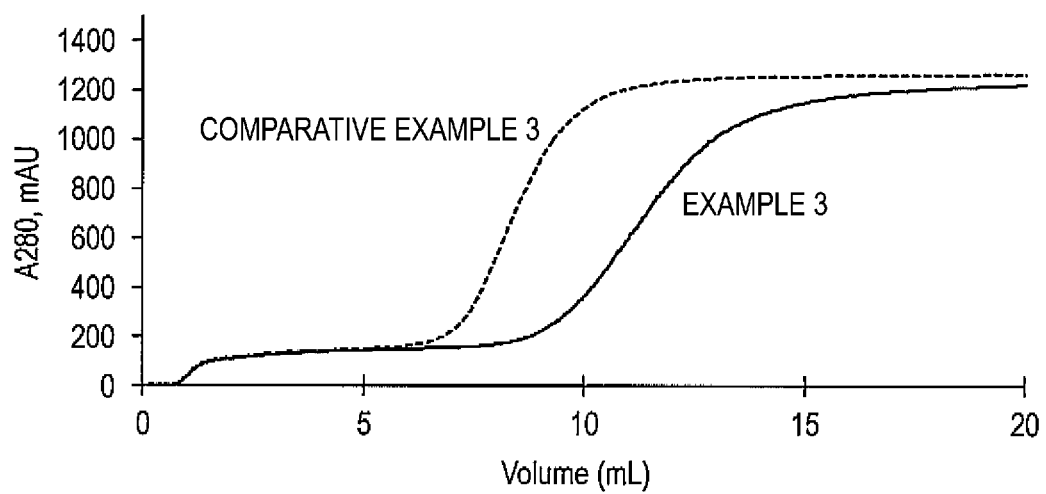

FIG. 4 depicts the chromatogram. The DBC calculated from the chromatogram of FIG. 4 was 8.9 mg/mL-column in Example 3 (IgG-binding peptide divalent fusion protein) and 6.9 mg/mL-column in Comparative Example 3 (synthetic peptide), and it was revealed that the column on which the peptide divalent fusion protein was immobilized had improved adsorption performance as compared with the synthetic peptide-immobilized column.

Example 4: Adsorption and Desorption of γ-Globulin

Figure 5:
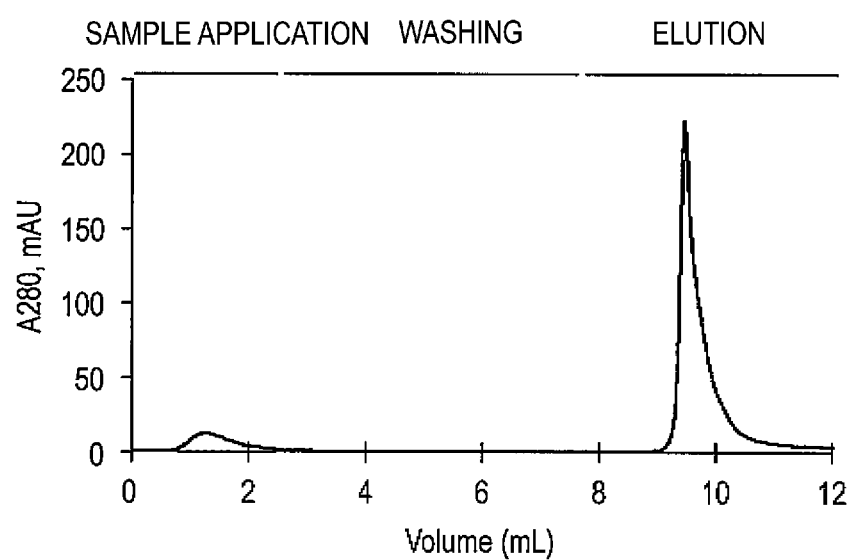

Using the column prepared in Example 3, it was examined whether IgG could be adsorbed or desorbed. The column was set on a liquid chromatography instrument AKTA pure 25 (GE Healthcare) and equilibrated with an adsorption solution, and then 500 µl of 1 mg/mL human serum-derived γ-globulin was fed at a flow rate of 1 mL/min. After washing the column with 5 mL of the adsorption solution, the adsorbed component was eluted by passing the elution solution (20 mM citric acid, pH 2.5). FIG. 5 depicts the chromatogram.

Elution of adsorbed human serum-derived γ-globulin was confirmed by lowering the pH, and it was revealed that the peptide could be used as a ligand for an affinity column.

Example 5: Affinity Measurement of IgG-Binding Peptide-Fused Yellow Fluorescent Protein To verify whether the IgG-binding peptide also functions for other scaffold proteins, a molecule (DNA sequence: SEQ ID NO: 54, amino acid sequence: SEQ ID NO: 55) in which an IgG-binding peptide was fused to a yellow fluorescent protein (sfYFP) was designed, and protein expression/purification and affinity analysis were performed in the same manner as in Example 1. Biacore X100 and Biacore X100 Evaluation Software were used as the affinity measuring device and the analysis software, respectively.

Comparative Example 4

As Comparative Example 4, a yellow fluorescent protein (sfYFP, DNA sequence: SEQ ID NO: 52, amino acid sequence: SEQ ID NO: 53) to which an IgG-binding peptide was not fused was expressed and purified in the same manner as in Example 5, and the affinity was measured. FIG. 6 depicts the results of Example 5 and Comparative Example 4.

As shown in FIG. 6, it was revealed that the peptide fused to the yellow fluorescent protein has an IgG binding function.

Example 6: Affinity Measurement of IgA- and IgY-Binding Peptide Fusion Protein

To verify whether other peptides having a specific binding capability also function in the same manner as IgG-binding peptides, molecules in which IgA and IgY-binding peptides were fused to a green fluorescent protein (sfGFP) were designed (DNA sequence: SEQ ID NO: 56 and amino acid sequence: SEQ ID NO: 57, DNA sequence: SEQ ID NO: 58 and amino acid sequence: SEQ ID NO: 59, respectively), and protein expression/purification and affinity analysis were performed in the same manner as in Example 5.

As shown in FIG. 7, it was revealed that the IgA and IgY-binding peptides fused to the green fluorescent protein have a binding function, and it was shown that a peptide having a specific binding capability can retain its binding function even when fused to a scaffold protein.

Example 7: Absorption/Desorption of IgA and IgY

Using a column in which 10 mg of a molecule in which IgA and IgY-binding peptides were fused to the green fluorescent protein (sfGFP) prepared in Example 6 was immobilized, it was examined whether IgA and IgY could be adsorbed and desorbed. The column was set on a liquid chromatography instrument AKTA pure 25 (GE Healthcare) and equilibrated with an adsorption solution, and then 0.2 mg/mL human serum-derived IgA or chicken IgY was fed in an amount of 500 µL at a flow rate of 1 mL/min. After washing the column with 5 mL of the adsorption solution, the adsorbed component was eluted by passing the elution solution (20 mM citric acid, pH 2.5). FIG. 8 depicts the chromatogram.

Elution of adsorbed IgA or IgY was confirmed by lowering the pH, and it was revealed that the peptide can be used as a ligand for an affinity column.

All publications, patents and patent applications cited herein are incorporated herein by reference in their entirety.

The invention claimed is:

1. A peptide fusion protein comprising two or more peptides having a specific binding capability and a scaffold protein selected from the group consisting of green fluorescent protein (GFP), red fluorescent protein (DsRed), or a variant thereof, each of said two or more peptides having a specific binding capability being positioned in said fusion protein as defined below, wherein a peptide having a specific binding capability is inserted directly or via a peptide linker between the first amino acid and the second amino acid in the amino acid sequence set forth in SEQ ID NO:32 of the GFP or the corresponding amino acid sequence of the GFP variant, and/or between two adjacent amino acids at positions 155-160 and/or between two adjacent amino acids at positions 170-176 in the amino acid sequence set forth in SEQ ID NO:32 of the GFP or the corresponding amino acid sequence of the GFP variant, and/or is linked directly or via a peptide linker to a C-terminal amino acid of the GFP or GFP variant; or wherein a peptide having a specific binding capability is inserted directly or via a peptide linker between the first amino acid and the second amino acid in the amino acid sequence set forth in SEQ ID NO:61 of the DsRed or the corresponding amino acid sequence of the DsRed variant, and/or between two adjacent amino acids at positions 153-158 and/or between two adjacent amino acids at positions 166-172 in the amino acid sequence set forth in SEQ ID NO:61 of the DsRed or the corresponding amino acid sequence of the DsRed variant, and/or is linked directly or via a peptide linker to a C-terminal amino acid of the DsRed or DsRed variant.

2. The peptide fusion protein according to claim 1, wherein the peptide having a specific binding capability is an antibody-binding peptide.

3. The peptide fusion protein according to claim 2, wherein the antibody-binding peptide is selected from the group consisting of an IgG-binding peptide, an IgA-binding peptide, and an IgY-binding peptide.

4. The peptide fusion protein according to claim 3, wherein the IgG-binding peptide is a peptide having a cyclic structure.

5. The peptide fusion protein according to claim 1, wherein the GFP variant is Superfolder GFP or Superfolder yellow fluorescent protein (YFP).

6. The peptide fusion protein according to claim 1, wherein the peptide linker comprises one or more amino acid sequences: GGGGS (SEQ ID NO: 35).

7. The peptide fusion protein according to claim 1, wherein the peptide linker is linked to the N-terminal and/or C-terminal of the peptide having a specific binding capability.

8. A solid-phase carrier having the peptide fusion protein described in claim 1 immobilized thereon.

9. The solid-phase carrier according to claim 8, which has a spacer between the peptide fusion protein and a solid phase.

10. A column for separating a target molecule, comprising the solid-phase carrier described in claim 8.

11. A method for producing a peptide fusion protein, comprising culturing a cell having a nucleic acid encoding the peptide fusion protein described in claim 1.

12. The method according to claim 11, wherein the cell is *Escherichia coli*.

* * * * *

SEQUENCE LISTING

<160> NUMBER OF SEQ ID NOS: 88

<210> SEQ ID NO 1
<211> LENGTH: 13
<212> TYPE: PRT
<213> ORGANISM: Artificial
<220> FEATURE:
<223> OTHER INFORMATION: IgG binding peptide
<220> FEATURE:

```
<221> NAME/KEY: misc_feature
<222> LOCATION: (6)..(6)
<223> OTHER INFORMATION: Xaa is arginine, lysine, leucine or asparagine

<400> SEQUENCE: 1

Asp Cys Ala Tyr His Xaa Gly Glu Leu Val Trp Cys Thr
1               5                   10

<210> SEQ ID NO 2
<211> LENGTH: 17
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (8)..(8)
<223> OTHER INFORMATION: Xaa is arginine, lysine, leucine or asparagine

<400> SEQUENCE: 2

Gly Pro Asp Cys Ala Tyr His Xaa Gly Glu Leu Val Trp Cys Thr Phe
1               5                   10                  15

His

<210> SEQ ID NO 3
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 3

Arg Cys Ala Tyr His Xaa Gly Glu Leu Val Trp Cys Ser
1               5                   10

<210> SEQ ID NO 4
<211> LENGTH: 17
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (8)..(8)
<223> OTHER INFORMATION: Xaa is arginine, lysine, leucine or asparagine

<400> SEQUENCE: 4

Gly Pro Arg Cys Ala Tyr His Xaa Gly Glu Leu Val Trp Cys Ser Phe
1               5                   10                  15

His

<210> SEQ ID NO 5
<211> LENGTH: 17
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (8)..(8)
<223> OTHER INFORMATION: Xaa is arginine, lysine, leucine or asparagine

<400> SEQUENCE: 5

Ser Pro Asp Cys Ala Tyr His Xaa Gly Glu Leu Val Trp Cys Thr Phe
```

```
1               5                   10                  15
His

<210> SEQ ID NO 6
<211> LENGTH: 17
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (8)..(8)
<223> OTHER INFORMATION: Xaa is arginine, lysine, leucine or asparagine

<400> SEQUENCE: 6

Gly Asp Asp Cys Ala Tyr His Xaa Gly Glu Leu Val Trp Cys Thr Phe
1               5                   10                  15
His

<210> SEQ ID NO 7
<211> LENGTH: 17
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (8)..(8)
<223> OTHER INFORMATION: Xaa is arginine, lysine, leucine or asparagine

<400> SEQUENCE: 7

Gly Pro Ser Cys Ala Tyr His Xaa Gly Glu Leu Val Trp Cys Thr Phe
1               5                   10                  15
His

<210> SEQ ID NO 8
<211> LENGTH: 17
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (8)..(8)
<223> OTHER INFORMATION: Xaa is arginine, lysine, leucine or asparagine

<400> SEQUENCE: 8

Gly Pro Asp Cys Ala Tyr His Xaa Gly Glu Leu Val Trp Cys Ser Phe
1               5                   10                  15
His

<210> SEQ ID NO 9
<211> LENGTH: 17
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (8)..(8)
<223> OTHER INFORMATION: Xaa is arginine, lysine, leucine or asparagine

<400> SEQUENCE: 9

Gly Pro Asp Cys Ala Tyr His Xaa Gly Glu Leu Val Trp Cys Thr His
1               5                   10                  15
His
```

```
<210> SEQ ID NO 10
<211> LENGTH: 17
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (8)..(8)
<223> OTHER INFORMATION: Xaa is arginine, lysine, leucine or asparagine

<400> SEQUENCE: 10

Gly Pro Asp Cys Ala Tyr His Xaa Gly Glu Leu Val Trp Cys Thr Phe
1               5                   10                  15

Tyr

<210> SEQ ID NO 11
<211> LENGTH: 17
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (8)..(8)
<223> OTHER INFORMATION: Xaa is arginine, lysine, leucine or asparagine

<400> SEQUENCE: 11

Ser Pro Asp Cys Ala Tyr His Xaa Gly Glu Leu Val Trp Cys Thr Phe
1               5                   10                  15

Tyr

<210> SEQ ID NO 12
<211> LENGTH: 17
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (8)..(8)
<223> OTHER INFORMATION: Xaa is arginine, lysine, leucine or asparagine

<400> SEQUENCE: 12

Ser Asp Asp Cys Ala Tyr His Xaa Gly Glu Leu Val Trp Cys Thr Phe
1               5                   10                  15

Tyr

<210> SEQ ID NO 13
<211> LENGTH: 17
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (8)..(8)
<223> OTHER INFORMATION: Xaa is arginine, lysine, leucine or asparagine

<400> SEQUENCE: 13

Arg Gly Asn Cys Ala Tyr His Xaa Gly Gln Leu Val Trp Cys Thr Tyr
1               5                   10                  15

His

<210> SEQ ID NO 14
```

```
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 14

Asp Cys Thr Tyr His Xaa Gly Asn Leu Val Trp Cys Thr
1               5                   10

<210> SEQ ID NO 15
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 15

Asp Cys Ala Tyr His Xaa Gly Asn Leu Val Trp Cys Thr
1               5                   10

<210> SEQ ID NO 16
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 16

Asp Cys Thr Tyr His Xaa Gly Glu Leu Val Trp Cys Thr
1               5                   10

<210> SEQ ID NO 17
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 17

Asp Cys Ala Trp His Xaa Gly Glu Leu Val Trp Cys Thr
1               5                   10

<210> SEQ ID NO 18
<211> LENGTH: 17
<212> TYPE: PRT
<213> ORGANISM: Artificial
<220> FEATURE:
<223> OTHER INFORMATION: IgG binding peptide

<400> SEQUENCE: 18

Gly Pro Asp Cys Ala Tyr His Arg Gly Glu Leu Val Trp Cys Thr Phe
1               5                   10                  15
```

His

<210> SEQ ID NO 19
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 19

Asp Cys Thr Tyr Thr Xaa Gly Asn Leu Val Trp Cys Thr
1               5                   10

<210> SEQ ID NO 20
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 20

Asp Cys Ala Tyr Thr Xaa Gly Asn Leu Val Trp Cys Thr
1               5                   10

<210> SEQ ID NO 21
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 21

Asp Cys Ser Tyr Thr Xaa Gly Asn Leu Val Trp Cys Thr
1               5                   10

<210> SEQ ID NO 22
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 22

Asp Cys Thr Trp Thr Xaa Gly Asn Leu Val Trp Cys Thr
1               5                   10

<210> SEQ ID NO 23
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 23

Asp Cys Thr Tyr His Xaa Gly Asn Leu Val Trp Cys Thr
1               5                   10

<210> SEQ ID NO 24
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 24

Asp Cys Thr Tyr Arg Xaa Gly Asn Leu Val Trp Cys Thr
1               5                   10

<210> SEQ ID NO 25
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 25

Asp Cys Thr Tyr Ser Xaa Gly Asn Leu Val Trp Cys Thr
1               5                   10

<210> SEQ ID NO 26
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 26

Asp Cys Thr Tyr Thr Xaa Gly Asn Leu Val Trp Cys Thr
1               5                   10

<210> SEQ ID NO 27
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 27

Asp Cys Thr Tyr Thr Xaa Gly Glu Leu Val Trp Cys Thr
1               5                   10

<210> SEQ ID NO 28
<211> LENGTH: 13

```
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 28

Asp Cys Thr Tyr Thr Xaa Gly Arg Leu Val Trp Cys Thr
1               5                   10

<210> SEQ ID NO 29
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 29

Asp Cys Thr Tyr Thr Xaa Gly Asp Leu Val Trp Cys Thr
1               5                   10

<210> SEQ ID NO 30
<211> LENGTH: 13
<212> TYPE: PRT
<213> ORGANISM: Artificial
<220> FEATURE:
<223> OTHER INFORMATION: IgG binding peptide
<220> FEATURE:
<221> NAME/KEY: misc_feature
<222> LOCATION: (6)..(6)
<223> OTHER INFORMATION: Xaa is arginine, lysine, leucine or asparagine

<400> SEQUENCE: 30

Asp Cys Thr Tyr Thr Xaa Gly Asn Leu Ile Trp Cys Thr
1               5                   10

<210> SEQ ID NO 31
<211> LENGTH: 714
<212> TYPE: DNA
<213> ORGANISM: Aequorea victoria
<220> FEATURE:
<221> NAME/KEY: CDS
<222> LOCATION: (1)..(714)

<400> SEQUENCE: 31 atg agc aaa ggc gaa gaa ctg ttt acc ggt gtg gtt ccg att ctg gtg      48
Met Ser Lys Gly Glu Glu Leu Phe Thr Gly Val Val Pro Ile Leu Val
1               5                   10                  15 gaa ctg gat ggc gat gtt aat ggt cat aaa ttt agc gtt agc ggt gaa      96
Glu Leu Asp Gly Asp Val Asn Gly His Lys Phe Ser Val Ser Gly Glu
            20                  25                  30 ggc gaa ggt gat gcg acc tat ggc aaa ctg acc ctg aaa ttt atc tgc     144
Gly Glu Gly Asp Ala Thr Tyr Gly Lys Leu Thr Leu Lys Phe Ile Cys
        35                  40                  45 acc acc ggt aaa ctg ccg gtg ccg tgg ccg acc ctg gtt acc acg ttt     192
Thr Thr Gly Lys Leu Pro Val Pro Trp Pro Thr Leu Val Thr Thr Phe
    50                  55                  60 agc tat ggc gtt cag tgt ttt agc cgc tat ccg gat cac atg aaa cag     240
Ser Tyr Gly Val Gln Cys Phe Ser Arg Tyr Pro Asp His Met Lys Gln
65                  70                  75                  80
```

| | | |
|---|---|---|
| cat gat ttc ttt aaa agc gcg atg ccg gaa ggc tat gtg cag gaa cgt<br>His Asp Phe Phe Lys Ser Ala Met Pro Glu Gly Tyr Val Gln Glu Arg<br>            85                  90                  95 | | 288 |
| acc att ttc ttt aaa gat gat ggt aac tac aaa acc cgc gcc gaa gtg<br>Thr Ile Phe Phe Lys Asp Asp Gly Asn Tyr Lys Thr Arg Ala Glu Val<br>        100                 105                 110 | | 336 |
| aaa ttt gaa ggc gat acc ctg gtt aac cgt atc gaa ctg aaa ggt atc<br>Lys Phe Glu Gly Asp Thr Leu Val Asn Arg Ile Glu Leu Lys Gly Ile<br>    115                 120                 125 | | 384 |
| gat ttc aaa gaa gat ggc aat atc ctg ggt cat aaa ctg gaa tac aac<br>Asp Phe Lys Glu Asp Gly Asn Ile Leu Gly His Lys Leu Glu Tyr Asn<br>130                 135                 140 | | 432 |
| tac aac agc cat aac gtg tac att atg gcg gat aaa cag aaa aac ggc<br>Tyr Asn Ser His Asn Val Tyr Ile Met Ala Asp Lys Gln Lys Asn Gly<br>145                 150                 155                 160 | | 480 |
| atc aaa gtt aac ttc aaa atc cgc cat aac atc gaa gat ggt agc gtg<br>Ile Lys Val Asn Phe Lys Ile Arg His Asn Ile Glu Asp Gly Ser Val<br>                165                 170                 175 | | 528 |
| cag ctg gcc gat cat tat cag cag aac acc ccg att ggc gat ggt ccg<br>Gln Leu Ala Asp His Tyr Gln Gln Asn Thr Pro Ile Gly Asp Gly Pro<br>            180                 185                 190 | | 576 |
| gtg ctg ctg ccg gat aat cat tat ctg agc acc cag agc gcc ctg agc<br>Val Leu Leu Pro Asp Asn His Tyr Leu Ser Thr Gln Ser Ala Leu Ser<br>        195                 200                 205 | | 624 |
| aaa gat ccg aac gaa aaa cgt gat cac atg gtg ctg ctg gaa ttt gtt<br>Lys Asp Pro Asn Glu Lys Arg Asp His Met Val Leu Leu Glu Phe Val<br>    210                 215                 220 | | 672 |
| acc gcg gcc ggc atc acc cat ggt atg gat gaa ctg tat aaa<br>Thr Ala Ala Gly Ile Thr His Gly Met Asp Glu Leu Tyr Lys<br>225                 230                 235 | | 714 |

<210> SEQ ID NO 32
<211> LENGTH: 238
<212> TYPE: PRT
<213> ORGANISM: Aequorea victoria

<400> SEQUENCE: 32

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val

|     |     |     |     |     |     |     |     |     |     |     |     |
| --- | --- | --- | --- | --- | --- | --- | --- | --- | --- | --- | --- |
|     |     | 165 |     |     |     | 170 |     |     |     | 175 |     |

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 33
<211> LENGTH: 717
<212> TYPE: DNA
<213> ORGANISM: Artificial
<220> FEATURE:
<223> OTHER INFORMATION: Superfolder green fluorescent protein
<220> FEATURE:
<221> NAME/KEY: CDS
<222> LOCATION: (1)..(717)

<400> SEQUENCE: 33

| atg cgt aag ggc gag gaa ctg ttc acc ggc gtg gtt ccg atc ctg gtg | 48 |
|---|---|
| Met Arg Lys Gly Glu Glu Leu Phe Thr Gly Val Val Pro Ile Leu Val | |
| 1               5                   10                  15 | |

| gag ctg gac ggt gat gtt aac ggc cac aaa ttt agc gtg cgt ggc gag | 96 |
|---|---|
| Glu Leu Asp Gly Asp Val Asn Gly His Lys Phe Ser Val Arg Gly Glu | |
|             20                  25                  30 | |

| ggt gaa ggt gat gcg acc aac ggc aag ctg acc ctg aaa ttc att tgc | 144 |
|---|---|
| Gly Glu Gly Asp Ala Thr Asn Gly Lys Leu Thr Leu Lys Phe Ile Cys | |
|         35                  40                  45 | |

| acc acc ggc aag ctg ccg gtg ccg tgg ccg acc ctg gtt acc acc ctg | 192 |
|---|---|
| Thr Thr Gly Lys Leu Pro Val Pro Trp Pro Thr Leu Val Thr Thr Leu | |
| 50                  55                  60 | |

| acc tac ggt gtg cag tgc ttt gcg cgt tat ccg gac cac atg aag caa | 240 |
|---|---|
| Thr Tyr Gly Val Gln Cys Phe Ala Arg Tyr Pro Asp His Met Lys Gln | |
| 65                  70                  75                  80 | |

| cac gat ttc ttt aaa agc gcg atg ccg gag ggt tac gtt caa gaa cgt | 288 |
|---|---|
| His Asp Phe Phe Lys Ser Ala Met Pro Glu Gly Tyr Val Gln Glu Arg | |
|             85                  90                  95 | |

| acc atc agc ttc aag gac gat ggc acc tat aaa acc cgt gcg gaa gtg | 336 |
|---|---|
| Thr Ile Ser Phe Lys Asp Asp Gly Thr Tyr Lys Thr Arg Ala Glu Val | |
|         100                 105                 110 | |

| aag ttt gaa ggt gac acc ctg gtt aac cgt atc gag ctg aag ggc att | 384 |
|---|---|
| Lys Phe Glu Gly Asp Thr Leu Val Asn Arg Ile Glu Leu Lys Gly Ile | |
|     115                 120                 125 | |

| gac ttc aaa gaa gat ggt aac atc ctg ggc cac aaa ctg gag tac aac | 432 |
|---|---|
| Asp Phe Lys Glu Asp Gly Asn Ile Leu Gly His Lys Leu Glu Tyr Asn | |
| 130                 135                 140 | |

| ttt aac agc cac aac gtt tat att acc gcg gat aag cag aaa aac ggt | 480 |
|---|---|
| Phe Asn Ser His Asn Val Tyr Ile Thr Ala Asp Lys Gln Lys Asn Gly | |
| 145                 150                 155                 160 | |

| atc aag gcg aac ttt aaa att cgt cac aac gtg gaa gac ggc agc gtt | 528 |
|---|---|
| Ile Lys Ala Asn Phe Lys Ile Arg His Asn Val Glu Asp Gly Ser Val | |
|             165                 170                 175 | |

| caa ctg gcg gat cac tac cag caa aac acc ccg att ggt gat ggt ccg | 576 |
|---|---|
| Gln Leu Ala Asp His Tyr Gln Gln Asn Thr Pro Ile Gly Asp Gly Pro | |
|         180                 185                 190 | |

| gtg ctg ctg ccg gat aac cac tat ctg agc acc cag agc gtt ctg agc | 624 |
|---|---|
| Val Leu Leu Pro Asp Asn His Tyr Leu Ser Thr Gln Ser Val Leu Ser | |
|     195                 200                 205 | |

```
aag gac ccg aac gag aaa cgt gat cac atg gtg ctg ctg gaa ttc gtt      672
Lys Asp Pro Asn Glu Lys Arg Asp His Met Val Leu Leu Glu Phe Val
    210             215                 220 acc gcg gcg ggt att acc cac ggc atg gat gaa ctg tat aag taa          717
Thr Ala Ala Gly Ile Thr His Gly Met Asp Glu Leu Tyr Lys
225                 230                 235
```

<210> SEQ ID NO 34
<211> LENGTH: 238
<212> TYPE: PRT
<213> ORGANISM: Artificial
<220> FEATURE:
<223> OTHER INFORMATION: Synthetic Construct

<400> SEQUENCE: 34

```
Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 35
<211> LENGTH: 5
<212> TYPE: PRT
<213> ORGANISM: Artificial
<220> FEATURE:
<223> OTHER INFORMATION: Peptide linker

<400> SEQUENCE: 35

```
Gly Gly Gly Gly Ser
1               5
```

<210> SEQ ID NO 36
<211> LENGTH: 3

-continued

```
<212> TYPE: PRT
<213> ORGANISM: Artificial
<220> FEATURE:
<223> OTHER INFORMATION: Peptide linker

<400> SEQUENCE: 36

Gly Gly Gly
1

<210> SEQ ID NO 37
<211> LENGTH: 6
<212> TYPE: PRT
<213> ORGANISM: Artificial
<220> FEATURE:
<223> OTHER INFORMATION: Histidine-tag

<400> SEQUENCE: 37

His His His His His His
1               5

<210> SEQ ID NO 38
<211> LENGTH: 8
<212> TYPE: PRT
<213> ORGANISM: Artificial
<220> FEATURE:
<223> OTHER INFORMATION: FLAG-tag

<400> SEQUENCE: 38

Asp Tyr Lys Asp Asp Asp Asp Lys
1               5

<210> SEQ ID NO 39
<211> LENGTH: 8
<212> TYPE: PRT
<213> ORGANISM: Artificial
<220> FEATURE:
<223> OTHER INFORMATION: Strep-tag

<400> SEQUENCE: 39

Trp Ser His Pro Gln Phe Glu Lys
1               5

<210> SEQ ID NO 40
<211> LENGTH: 744
<212> TYPE: DNA
<213> ORGANISM: Artificial
<220> FEATURE:
<223> OTHER INFORMATION: sfGFP with His tag
<220> FEATURE:
<221> NAME/KEY: CDS
<222> LOCATION: (1)..(744)

<400> SEQUENCE: 40 atg cgt aag ggc gag gaa ctg ttc acc ggc gtg gtt ccg atc ctg gtg      48
Met Arg Lys Gly Glu Glu Leu Phe Thr Gly Val Val Pro Ile Leu Val
1               5                   10                  15 gag ctg gac ggt gat gtt aac ggc cac aaa ttt agc gtg cgt ggc gag      96
Glu Leu Asp Gly Asp Val Asn Gly His Lys Phe Ser Val Arg Gly Glu
                20                  25                  30 ggt gaa ggt gat gcg acc aac ggc aag ctg acc ctg aaa ttc att tgc     144
Gly Glu Gly Asp Ala Thr Asn Gly Lys Leu Thr Leu Lys Phe Ile Cys
            35                  40                  45 acc acc ggc aag ctg ccg gtg ccg tgg ccg acc ctg gtt acc acc ctg     192
Thr Thr Gly Lys Leu Pro Val Pro Trp Pro Thr Leu Val Thr Thr Leu
        50                  55                  60 acc tac ggt gtg cag tgc ttt gcg cgt tat ccg gac cac atg aag caa     240
```

```
Thr Tyr Gly Val Gln Cys Phe Ala Arg Tyr Pro Asp His Met Lys Gln
 65                  70                  75                  80 cac gat ttc ttt aaa agc gcg atg ccg gag ggt tac gtt caa gaa cgt    288
His Asp Phe Phe Lys Ser Ala Met Pro Glu Gly Tyr Val Gln Glu Arg
                 85                  90                  95 acc atc agc ttc aag gac gat ggc acc tat aaa acc cgt gcg gaa gtg    336
Thr Ile Ser Phe Lys Asp Asp Gly Thr Tyr Lys Thr Arg Ala Glu Val
            100                 105                 110 aag ttt gaa ggt gac acc ctg gtt aac cgt atc gag ctg aag ggc att    384
Lys Phe Glu Gly Asp Thr Leu Val Asn Arg Ile Glu Leu Lys Gly Ile
        115                 120                 125 gac ttc aaa gaa gat ggt aac atc ctg ggc cac aaa ctg gag tac aac    432
Asp Phe Lys Glu Asp Gly Asn Ile Leu Gly His Lys Leu Glu Tyr Asn
    130                 135                 140 ttt aac agc cac aac gtt tat att acc gcg gat aag cag aaa aac ggt    480
Phe Asn Ser His Asn Val Tyr Ile Thr Ala Asp Lys Gln Lys Asn Gly
145                 150                 155                 160 atc aag gcg aac ttt aaa att cgt cac aac gtg gaa gac ggc agc gtt    528
Ile Lys Ala Asn Phe Lys Ile Arg His Asn Val Glu Asp Gly Ser Val
                165                 170                 175 caa ctg gcg gat cac tac cag caa aac acc ccg att ggt gat ggt ccg    576
Gln Leu Ala Asp His Tyr Gln Gln Asn Thr Pro Ile Gly Asp Gly Pro
            180                 185                 190 gtg ctg ctg ccg gat aac cac tat ctg agc acc cag agc gtt ctg agc    624
Val Leu Leu Pro Asp Asn His Tyr Leu Ser Thr Gln Ser Val Leu Ser
        195                 200                 205 aag gac ccg aac gag aaa cgt gat cac atg gtg ctg ctg gaa ttc gtt    672
Lys Asp Pro Asn Glu Lys Arg Asp His Met Val Leu Leu Glu Phe Val
    210                 215                 220 acc gcg gcg ggt att acc cac ggc atg gat gaa ctg tat aag ggt ggc    720
Thr Ala Ala Gly Ile Thr His Gly Met Asp Glu Leu Tyr Lys Gly Gly
225                 230                 235                 240 ggt cat cac cac cac cac cac taa                                    744
Gly His His His His His His
                245
```

<210> SEQ ID NO 41
<211> LENGTH: 247
<212> TYPE: PRT
<213> ORGANISM: Artificial
<220> FEATURE:
<223> OTHER INFORMATION: Synthetic Construct

<400> SEQUENCE: 41

```
Met Arg Lys Gly Glu Glu Leu Phe Thr Gly Val Val Pro Ile Leu Val
  1               5                  10                  15

Glu Leu Asp Gly Asp Val Asn Gly His Lys Phe Ser Val Arg Gly Glu
                 20                  25                  30

Gly Glu Gly Asp Ala Thr Asn Gly Lys Leu Thr Leu Lys Phe Ile Cys
             35                  40                  45

Thr Thr Gly Lys Leu Pro Val Pro Trp Pro Thr Leu Val Thr Thr Leu
         50                  55                  60

Thr Tyr Gly Val Gln Cys Phe Ala Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
```

```
                115                 120                 125
Asp Phe Lys Glu Asp Gly Asn Ile Leu Gly His Lys Leu Glu Tyr Asn
            130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Gly Gly
225                 230                 235                 240

Gly His His His His His His
                245

<210> SEQ ID NO 42
<211> LENGTH: 825
<212> TYPE: DNA
<213> ORGANISM: Artificial
<220> FEATURE:
<223> OTHER INFORMATION: IgG binding peptide-fusion protein
<220> FEATURE:
<221> NAME/KEY: CDS
<222> LOCATION: (1)..(825)

<400> SEQUENCE: 42
```

| | | | | | | | | | | | | | | | | |
|---|---|---|---|---|---|---|---|---|---|---|---|---|---|---|---|---|
| atg | cgt | aaa | ggc | gag | gaa | ctg | ttt | acc | ggt | gtg | gtt | ccg | atc | ctg | gtg | 48 |
| Met | Arg | Lys | Gly | Glu | Glu | Leu | Phe | Thr | Gly | Val | Val | Pro | Ile | Leu | Val | |
| 1 | | | | 5 | | | | | 10 | | | | | 15 | | |
| gaa | ctg | gac | ggc | gat | gtt | aac | ggt | cac | aag | ttc | agc | gtt | cgt | ggt | gag | 96 |
| Glu | Leu | Asp | Gly | Asp | Val | Asn | Gly | His | Lys | Phe | Ser | Val | Arg | Gly | Glu | |
| | | | 20 | | | | | 25 | | | | | 30 | | | |
| ggc | gaa | ggt | gac | gcg | acc | aac | ggc | aag | ctg | acc | ctg | aaa | ttt | att | tgc | 144 |
| Gly | Glu | Gly | Asp | Ala | Thr | Asn | Gly | Lys | Leu | Thr | Leu | Lys | Phe | Ile | Cys | |
| | | 35 | | | | | 40 | | | | | 45 | | | | |
| acc | acc | ggt | aaa | ctg | ccg | gtg | ccg | tgg | ccg | acc | ctg | gtt | acc | acc | ctg | 192 |
| Thr | Thr | Gly | Lys | Leu | Pro | Val | Pro | Trp | Pro | Thr | Leu | Val | Thr | Thr | Leu | |
| | 50 | | | | | 55 | | | | | 60 | | | | | |
| acc | tac | ggt | gtg | cag | tgc | ttc | gcg | cgt | tat | ccg | gac | cac | atg | aag | caa | 240 |
| Thr | Tyr | Gly | Val | Gln | Cys | Phe | Ala | Arg | Tyr | Pro | Asp | His | Met | Lys | Gln | |
| 65 | | | | | 70 | | | | | 75 | | | | | 80 | |
| cac | gat | ttc | ttt | aaa | agc | gcg | atg | ccg | gag | ggc | tac | gtt | cag | gaa | cgt | 288 |
| His | Asp | Phe | Phe | Lys | Ser | Ala | Met | Pro | Glu | Gly | Tyr | Val | Gln | Glu | Arg | |
| | | | | 85 | | | | | 90 | | | | | 95 | | |
| acc | atc | agc | ttc | aag | gac | gat | ggt | acc | tat | aaa | acc | cgt | gcg | gaa | gtg | 336 |
| Thr | Ile | Ser | Phe | Lys | Asp | Asp | Gly | Thr | Tyr | Lys | Thr | Arg | Ala | Glu | Val | |
| | | | 100 | | | | | 105 | | | | | 110 | | | |
| aag | ttt | gaa | ggc | gac | acc | ctg | gtt | aac | cgt | atc | gag | ctg | aag | ggt | att | 384 |
| Lys | Phe | Glu | Gly | Asp | Thr | Leu | Val | Asn | Arg | Ile | Glu | Leu | Lys | Gly | Ile | |
| | | 115 | | | | | 120 | | | | | 125 | | | | |
| gac | ttc | aaa | gaa | gat | ggc | aac | atc | ctg | ggt | cac | aag | ctg | gag | tac | aac | 432 |
| Asp | Phe | Lys | Glu | Asp | Gly | Asn | Ile | Leu | Gly | His | Lys | Leu | Glu | Tyr | Asn | |
| | 130 | | | | | 135 | | | | | 140 | | | | | |
| ttt | aac | agc | cac | aac | gtg | tat | att | acc | gcg | gat | aag | cag | aaa | aac | ggc | 480 |
| Phe | Asn | Ser | His | Asn | Val | Tyr | Ile | Thr | Ala | Asp | Lys | Gln | Lys | Asn | Gly | |
| 145 | | | | | 150 | | | | | 155 | | | | | 160 | |

```
atc aag gcg aac ttc aaa att cgt cac aac gtg gaa gac ggt agc gtt    528
Ile Lys Ala Asn Phe Lys Ile Arg His Asn Val Glu Asp Gly Ser Val
            165                 170                 175 caa ctg gcg gat cac tac cag caa aac acc ccg att ggt gat ggt ccg    576
Gln Leu Ala Asp His Tyr Gln Gln Asn Thr Pro Ile Gly Asp Gly Pro
        180                 185                 190 gtg ctg ctg ccg gat aac cac tat ctg agc acc caa agc gtt ctg agc    624
Val Leu Leu Pro Asp Asn His Tyr Leu Ser Thr Gln Ser Val Leu Ser
    195                 200                 205 aag gac ccg aac gag aaa cgt gat cac atg gtg ctg ctg gaa ttt gtt    672
Lys Asp Pro Asn Glu Lys Arg Asp His Met Val Leu Leu Glu Phe Val
210                 215                 220 acc gcg gcg ggc att acc cac ggt atg gac gag ctg tac aaa ggt ggc    720
Thr Ala Ala Gly Ile Thr His Gly Met Asp Glu Leu Tyr Lys Gly Gly
225                 230                 235                 240 ggt ggc agc ggt ggc ggt ggc agc ggc ccg gat tgc gcg tat cac cgc    768
Gly Gly Ser Gly Gly Gly Gly Ser Gly Pro Asp Cys Ala Tyr His Arg
                245                 250                 255 ggc gaa ctg gtt tgg tgc acc ttc cac ggc ggc ggt cat cat cat cat    816
Gly Glu Leu Val Trp Cys Thr Phe His Gly Gly Gly His His His His
            260                 265                 270 cat cac taa                                                         825
His His

<210> SEQ ID NO 43
<211> LENGTH: 274
<212> TYPE: PRT
<213> ORGANISM: Artificial
<220> FEATURE:
<223> OTHER INFORMATION: Synthetic Construct

<400> SEQUENCE: 43

Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205
```

```
Lys Asp Pro Asn Glu Lys Arg Asp His Met Val Leu Leu Glu Phe Val
        210                 215                 220

Thr Ala Ala Gly Ile Thr His Gly Met Asp Glu Leu Tyr Lys Gly Gly
225                 230                 235                 240

Gly Gly Ser Gly Gly Gly Ser Gly Pro Asp Cys Ala Tyr His Arg
            245                 250                 255

Gly Glu Leu Val Trp Cys Thr Phe His Gly Gly His His His His
            260                 265                 270

His His

<210> SEQ ID NO 44
<211> LENGTH: 906
<212> TYPE: DNA
<213> ORGANISM: Artificial
<220> FEATURE:
<223> OTHER INFORMATION: IgG binding peptide-fusion protein
<220> FEATURE:
<221> NAME/KEY: CDS
<222> LOCATION: (1)..(906)

<400> SEQUENCE: 44
```

| | | | | | | | | | | | | | | | | |
|---|---|---|---|---|---|---|---|---|---|---|---|---|---|---|---|---|
| atg | ggt | ccg | gac | tgc | gcg | tat | cac | cgt | ggc | gag | ctg | gtg | tgg | tgc | acc | 48 |
| Met | Gly | Pro | Asp | Cys | Ala | Tyr | His | Arg | Gly | Glu | Leu | Val | Trp | Cys | Thr | |
| 1 | | | | 5 | | | | | 10 | | | | | 15 | | |
| ttt | cat | ggt | ggc | ggt | ggc | agc | ggt | ggc | ggt | ggc | agc | cgt | aaa | ggc | gag | 96 |
| Phe | His | Gly | Gly | Gly | Gly | Ser | Gly | Gly | Gly | Gly | Ser | Arg | Lys | Gly | Glu | |
| | | | 20 | | | | | 25 | | | | | 30 | | | |
| gaa | ctg | ttt | acc | ggt | gtg | gtt | ccg | atc | ctg | gtg | gaa | ctg | gac | ggc | gat | 144 |
| Glu | Leu | Phe | Thr | Gly | Val | Val | Pro | Ile | Leu | Val | Glu | Leu | Asp | Gly | Asp | |
| | | | 35 | | | | | 40 | | | | | 45 | | | |
| gtt | aac | ggt | cac | aag | ttc | agc | gtt | cgt | ggt | gag | ggc | gaa | ggt | gac | gcg | 192 |
| Val | Asn | Gly | His | Lys | Phe | Ser | Val | Arg | Gly | Glu | Gly | Glu | Gly | Asp | Ala | |
| | | | 50 | | | | | 55 | | | | | 60 | | | |
| acc | aac | ggc | aag | ctg | acc | ctg | aaa | ttt | att | tgc | acc | acc | ggt | aaa | ctg | 240 |
| Thr | Asn | Gly | Lys | Leu | Thr | Leu | Lys | Phe | Ile | Cys | Thr | Thr | Gly | Lys | Leu | |
| 65 | | | | 70 | | | | | 75 | | | | | 80 | | |
| ccg | gtg | ccg | tgg | ccg | acc | ctg | gtt | acc | acc | ctg | acc | tac | ggt | gtg | cag | 288 |
| Pro | Val | Pro | Trp | Pro | Thr | Leu | Val | Thr | Thr | Leu | Thr | Tyr | Gly | Val | Gln | |
| | | | | 85 | | | | | 90 | | | | | 95 | | |
| tgc | ttc | gcg | cgt | tat | ccg | gac | cac | atg | aag | caa | cac | gat | ttc | ttt | aaa | 336 |
| Cys | Phe | Ala | Arg | Tyr | Pro | Asp | His | Met | Lys | Gln | His | Asp | Phe | Phe | Lys | |
| | | | 100 | | | | | 105 | | | | | 110 | | | |
| agc | gcg | atg | ccg | gag | ggc | tac | gtt | cag | gaa | cgt | acc | atc | agc | ttc | aag | 384 |
| Ser | Ala | Met | Pro | Glu | Gly | Tyr | Val | Gln | Glu | Arg | Thr | Ile | Ser | Phe | Lys | |
| | | | 115 | | | | | 120 | | | | | 125 | | | |
| gac | gat | ggt | acc | tat | aaa | acc | cgt | gcg | gaa | gtg | aag | ttt | gaa | ggc | gac | 432 |
| Asp | Asp | Gly | Thr | Tyr | Lys | Thr | Arg | Ala | Glu | Val | Lys | Phe | Glu | Gly | Asp | |
| | | 130 | | | | | 135 | | | | | 140 | | | | |
| acc | ctg | gtt | aac | cgt | atc | gag | ctg | aag | ggt | att | gac | ttc | aaa | gaa | gat | 480 |
| Thr | Leu | Val | Asn | Arg | Ile | Glu | Leu | Lys | Gly | Ile | Asp | Phe | Lys | Glu | Asp | |
| 145 | | | | 150 | | | | | 155 | | | | | 160 | | |
| ggc | aac | atc | ctg | ggt | cac | aag | ctg | gag | tac | aac | ttt | aac | agc | cac | aac | 528 |
| Gly | Asn | Ile | Leu | Gly | His | Lys | Leu | Glu | Tyr | Asn | Phe | Asn | Ser | His | Asn | |
| | | | | 165 | | | | | 170 | | | | | 175 | | |
| gtg | tat | att | acc | gcg | gat | aag | cag | aaa | aac | ggc | atc | aag | gcg | aac | ttc | 576 |
| Val | Tyr | Ile | Thr | Ala | Asp | Lys | Gln | Lys | Asn | Gly | Ile | Lys | Ala | Asn | Phe | |
| | | | 180 | | | | | 185 | | | | | 190 | | | |
| aaa | att | cgt | cac | aac | gtg | gaa | gac | ggt | agc | gtt | caa | ctg | gcg | gat | cac | 624 |
| Lys | Ile | Arg | His | Asn | Val | Glu | Asp | Gly | Ser | Val | Gln | Leu | Ala | Asp | His | |
| | | | | 195 | | | | | 200 | | | | | 205 | | |

```
tac cag caa aac acc ccg att ggt gat ggt ccg gtg ctg ctg ccg gat      672
Tyr Gln Gln Asn Thr Pro Ile Gly Asp Gly Pro Val Leu Leu Pro Asp
    210                 215                 220 aac cac tat ctg agc acc caa agc gtt ctg agc aag gac ccg aac gag      720
Asn His Tyr Leu Ser Thr Gln Ser Val Leu Ser Lys Asp Pro Asn Glu
225                 230                 235                 240 aaa cgt gat cac atg gtg ctg ctg gaa ttt gtt acc gcg gcg ggc att      768
Lys Arg Asp His Met Val Leu Leu Glu Phe Val Thr Ala Ala Gly Ile
                245                 250                 255 acc cac ggt atg gac gag ctg tac aaa ggt ggc ggt ggc agc ggt ggc      816
Thr His Gly Met Asp Glu Leu Tyr Lys Gly Gly Gly Gly Ser Gly Gly
            260                 265                 270 ggt ggc agc ggc ccg gat tgc gcg tat cac cgc ggc gaa ctg gtt tgg      864
Gly Gly Ser Gly Pro Asp Cys Ala Tyr His Arg Gly Glu Leu Val Trp
        275                 280                 285 tgc acc ttc cac ggc ggc ggt cat cat cat cat cat cac taa              906
Cys Thr Phe His Gly Gly Gly His His His His His His
    290                 295                 300

<210> SEQ ID NO 45
<211> LENGTH: 301
<212> TYPE: PRT
<213> ORGANISM: Artificial
<220> FEATURE:
<223> OTHER INFORMATION: Synthetic Construct

<400> SEQUENCE: 45

Met Gly Pro Asp Cys Ala Tyr His Arg Gly Glu Leu Val Trp Cys Thr
1               5                   10                  15

Phe His Gly Gly Gly Ser Gly Gly Gly Ser Arg Lys Gly Glu
            20                  25                  30

Glu Leu Phe Thr Gly Val Val Pro Ile Leu Val Glu Leu Asp Gly Asp
            35                  40                  45

Val Asn Gly His Lys Phe Ser Val Arg Gly Glu Gly Glu Gly Asp Ala
        50                  55                  60

Thr Asn Gly Lys Leu Thr Leu Lys Phe Ile Cys Thr Thr Gly Lys Leu
65                  70                  75                  80

Pro Val Pro Trp Pro Thr Leu Val Thr Thr Leu Thr Tyr Gly Val Gln
                85                  90                  95

Cys Phe Ala Arg Tyr Pro Asp His Met Lys Gln His Asp Phe Phe Lys
            100                 105                 110

Ser Ala Met Pro Glu Gly Tyr Val Gln Glu Arg Thr Ile Ser Phe Lys
        115                 120                 125

Asp Asp Gly Thr Tyr Lys Thr Arg Ala Glu Val Lys Phe Glu Gly Asp
    130                 135                 140

Thr Leu Val Asn Arg Ile Glu Leu Lys Gly Ile Asp Phe Lys Glu Asp
145                 150                 155                 160

Gly Asn Ile Leu Gly His Lys Leu Glu Tyr Asn Phe Asn Ser His Asn
                165                 170                 175

Val Tyr Ile Thr Ala Asp Lys Gln Lys Asn Gly Ile Lys Ala Asn Phe
            180                 185                 190

Lys Ile Arg His Asn Val Glu Asp Gly Ser Val Gln Leu Ala Asp His
        195                 200                 205

Tyr Gln Gln Asn Thr Pro Ile Gly Asp Gly Pro Val Leu Leu Pro Asp
    210                 215                 220

Asn His Tyr Leu Ser Thr Gln Ser Val Leu Ser Lys Asp Pro Asn Glu
225                 230                 235                 240
```

```
Lys Arg Asp His Met Val Leu Leu Glu Phe Val Thr Ala Ala Gly Ile
             245                 250                 255

Thr His Gly Met Asp Glu Leu Tyr Lys Gly Gly Gly Ser Gly Gly
         260                 265                 270

Gly Gly Ser Gly Pro Asp Cys Ala Tyr His Arg Gly Glu Leu Val Trp
         275                 280                 285

Cys Thr Phe His Gly Gly His His His His His His
    290                 295                 300

<210> SEQ ID NO 46
<211> LENGTH: 936
<212> TYPE: DNA
<213> ORGANISM: Artificial
<220> FEATURE:
<223> OTHER INFORMATION: IgG binding peptide-fusion protein
<220> FEATURE:
<221> NAME/KEY: CDS
<222> LOCATION: (1)..(936)

<400> SEQUENCE: 46
```

| | | | | | | | | | | | | | | | | |
|---|---|---|---|---|---|---|---|---|---|---|---|---|---|---|---|---|
| atg | cgt | aaa | ggc | gag | gaa | ctg | ttc | acc | ggt | gtg | gtt | ccg | atc | ctg | gtg | 48 |
| Met | Arg | Lys | Gly | Glu | Glu | Leu | Phe | Thr | Gly | Val | Val | Pro | Ile | Leu | Val | |
| 1 | | | | 5 | | | | | 10 | | | | | 15 | | |
| gag | ctg | gac | ggc | gat | gtt | aac | ggt | cac | aag | ttt | agc | gtg | cgt | ggt | gag | 96 |
| Glu | Leu | Asp | Gly | Asp | Val | Asn | Gly | His | Lys | Phe | Ser | Val | Arg | Gly | Glu | |
| | | | 20 | | | | | 25 | | | | | 30 | | | |
| ggc | gaa | ggt | gac | gcg | acc | aac | ggc | aag | ctg | acc | ctg | aaa | ttc | att | tgc | 144 |
| Gly | Glu | Gly | Asp | Ala | Thr | Asn | Gly | Lys | Leu | Thr | Leu | Lys | Phe | Ile | Cys | |
| | | | 35 | | | | | 40 | | | | | 45 | | | |
| acc | acc | ggt | aaa | ctg | ccg | gtg | ccg | tgg | ccg | acc | ctg | gtt | acc | acc | ctg | 192 |
| Thr | Thr | Gly | Lys | Leu | Pro | Val | Pro | Trp | Pro | Thr | Leu | Val | Thr | Thr | Leu | |
| | 50 | | | | | 55 | | | | | 60 | | | | | |
| acc | tac | ggt | gtg | cag | tgc | ttt | gcg | cgt | tat | ccg | gac | cac | atg | aag | caa | 240 |
| Thr | Tyr | Gly | Val | Gln | Cys | Phe | Ala | Arg | Tyr | Pro | Asp | His | Met | Lys | Gln | |
| 65 | | | | | 70 | | | | | 75 | | | | | 80 | |
| cac | gat | ttc | ttt | aaa | agc | gcg | atg | ccg | gag | ggc | tac | gtt | cag | gaa | cgt | 288 |
| His | Asp | Phe | Phe | Lys | Ser | Ala | Met | Pro | Glu | Gly | Tyr | Val | Gln | Glu | Arg | |
| | | | | 85 | | | | | 90 | | | | | 95 | | |
| acc | atc | agc | ttc | aag | gac | gat | ggt | acc | tat | aaa | acc | cgt | gcg | gaa | gtg | 336 |
| Thr | Ile | Ser | Phe | Lys | Asp | Asp | Gly | Thr | Tyr | Lys | Thr | Arg | Ala | Glu | Val | |
| | | | | 100 | | | | | 105 | | | | | 110 | | |
| aag | ttt | gaa | ggc | gat | acc | ctg | gtt | aac | cgt | atc | gag | ctg | aag | ggt | att | 384 |
| Lys | Phe | Glu | Gly | Asp | Thr | Leu | Val | Asn | Arg | Ile | Glu | Leu | Lys | Gly | Ile | |
| | | | 115 | | | | | 120 | | | | | 125 | | | |
| gac | ttc | aaa | gaa | gat | ggc | aac | atc | ctg | ggt | cac | aag | ctg | gaa | tac | aac | 432 |
| Asp | Phe | Lys | Glu | Asp | Gly | Asn | Ile | Leu | Gly | His | Lys | Leu | Glu | Tyr | Asn | |
| | | | 130 | | | | | 135 | | | | | 140 | | | |
| ttt | aac | agc | cac | aac | gtg | tat | att | acc | gcg | gac | aag | cag | aag | aac | ggt | 480 |
| Phe | Asn | Ser | His | Asn | Val | Tyr | Ile | Thr | Ala | Asp | Lys | Gln | Lys | Asn | Gly | |
| 145 | | | | | 150 | | | | | 155 | | | | | 160 | |
| atc | aag | gcg | aac | ttt | aaa | att | cgt | cac | aac | gtt | gag | ggt | ggt | ggt | ggc | 528 |
| Ile | Lys | Ala | Asn | Phe | Lys | Ile | Arg | His | Asn | Val | Glu | Gly | Gly | Gly | Gly | |
| | | | | 165 | | | | | 170 | | | | | 175 | | |
| agc | ggc | ggt | ggc | ggt | agc | ggt | ccg | gat | tgc | gcg | tac | cac | cgt | ggt | gaa | 576 |
| Ser | Gly | Gly | Gly | Gly | Ser | Gly | Pro | Asp | Cys | Ala | Tyr | His | Arg | Gly | Glu | |
| | | | 180 | | | | | 185 | | | | | 190 | | | |
| ctg | gtg | tgg | tgc | acc | ttt | cat | ggc | ggt | ggc | ggt | agc | ggc | ggt | ggc | ggt | 624 |
| Leu | Val | Trp | Cys | Thr | Phe | His | Gly | Gly | Gly | Gly | Ser | Gly | Gly | Gly | Gly | |
| | | | 195 | | | | | 200 | | | | | 205 | | | |
| agc | gat | ggt | agc | gtt | cag | ctg | gcg | gat | cac | tac | cag | caa | aac | acc | ccg | 672 |

```
Ser Asp Gly Ser Val Gln Leu Ala Asp His Tyr Gln Gln Asn Thr Pro
    210                 215                 220 att ggt gat ggt ccg gtg ctg ctg ccg gat aac cac tat ctg agc acc      720
Ile Gly Asp Gly Pro Val Leu Leu Pro Asp Asn His Tyr Leu Ser Thr
225                 230                 235                 240 caa agc gtt ctg agc aag gac ccg aac gag aaa cgt gat cac atg gtg      768
Gln Ser Val Leu Ser Lys Asp Pro Asn Glu Lys Arg Asp His Met Val
                245                 250                 255 ctg ctg gaa ttt gtt acc gcg gcg ggc att acc cac ggt atg gac gag      816
Leu Leu Glu Phe Val Thr Ala Ala Gly Ile Thr His Gly Met Asp Glu
            260                 265                 270 ctg tac aaa ggc ggt ggc ggt agc ggt ggt ggc ggt agc ggg ccg gat      864
Leu Tyr Lys Gly Gly Gly Gly Ser Gly Gly Gly Gly Ser Gly Pro Asp
        275                 280                 285 tgc gcg tat cac cgt ggt gaa ctg gtt tgg tgt act ttt cat ggc ggt      912
Cys Ala Tyr His Arg Gly Glu Leu Val Trp Cys Thr Phe His Gly Gly
    290                 295                 300 ggc cac cac cac cac cac cac taa                                       936
Gly His His His His His His
305                 310
```

<210> SEQ ID NO 47
<211> LENGTH: 311
<212> TYPE: PRT
<213> ORGANISM: Artificial
<220> FEATURE:
<223> OTHER INFORMATION: Synthetic Construct

<400> SEQUENCE: 47

```
Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Gly Gly Gly Gly
                165                 170                 175

Ser Gly Gly Gly Gly Ser Gly Pro Asp Cys Ala Tyr His Arg Gly Glu
            180                 185                 190

Leu Val Trp Cys Thr Phe His Gly Gly Gly Ser Gly Gly Gly Gly
        195                 200                 205

Ser Asp Gly Ser Val Gln Leu Ala Asp His Tyr Gln Gln Asn Thr Pro
    210                 215                 220
```

```
Ile Gly Asp Gly Pro Val Leu Leu Pro Asp Asn His Tyr Leu Ser Thr
225                 230                 235                 240

Gln Ser Val Leu Ser Lys Asp Pro Asn Glu Lys Arg Asp His Met Val
            245                 250                 255

Leu Leu Glu Phe Val Thr Ala Ala Gly Ile Thr His Gly Met Asp Glu
        260                 265                 270

Leu Tyr Lys Gly Gly Gly Ser Gly Gly Gly Ser Gly Pro Asp
    275                 280                 285

Cys Ala Tyr His Arg Gly Leu Val Trp Cys Thr Phe His Gly Gly
        290                 295                 300

Gly His His His His His His
305                 310

<210> SEQ ID NO 48
<211> LENGTH: 981
<212> TYPE: DNA
<213> ORGANISM: Artificial
<220> FEATURE:
<223> OTHER INFORMATION: IgG binding peptide-fusion protein
<220> FEATURE:
<221> NAME/KEY: CDS
<222> LOCATION: (1)..(981)

<400> SEQUENCE: 48 atg cgt aaa ggc gag gaa ctg ttc acc ggc gtg gtt ccg atc ctg gtg       48
Met Arg Lys Gly Glu Glu Leu Phe Thr Gly Val Val Pro Ile Leu Val
1               5                   10                  15 gag ctg gac ggt gat gtt aac ggc cac aag ttt agc gtg cgt ggc gag       96
Glu Leu Asp Gly Asp Val Asn Gly His Lys Phe Ser Val Arg Gly Glu
            20                  25                  30 ggt gaa ggt gat gcg acc aac ggc aag ctg acc ctg aaa ttc att tgc      144
Gly Glu Gly Asp Ala Thr Asn Gly Lys Leu Thr Leu Lys Phe Ile Cys
        35                  40                  45 acc acc ggt aaa ctg ccg gtg ccg tgg ccg acc ctg gtt acc acc ctg      192
Thr Thr Gly Lys Leu Pro Val Pro Trp Pro Thr Leu Val Thr Thr Leu
    50                  55                  60 acc tac ggt gtg cag tgc ttt gcg cgt tat ccg gac cac atg aag caa      240
Thr Tyr Gly Val Gln Cys Phe Ala Arg Tyr Pro Asp His Met Lys Gln
65                  70                  75                  80 cac gat ttc ttt aaa agc gcg atg ccg gag ggt tac gtt cag gaa cgt      288
His Asp Phe Phe Lys Ser Ala Met Pro Glu Gly Tyr Val Gln Glu Arg
                85                  90                  95 acc atc agc ttc aag gac gat ggt acc tat aaa acc cgt gcg gaa gtg      336
Thr Ile Ser Phe Lys Asp Asp Gly Thr Tyr Lys Thr Arg Ala Glu Val
            100                 105                 110 aag ttt gaa ggt gat acc ctg gtt aac cgt atc gag ctg aag ggc att      384
Lys Phe Glu Gly Asp Thr Leu Val Asn Arg Ile Glu Leu Lys Gly Ile
        115                 120                 125 gac ttc aaa gaa gat ggt aac atc ctg ggc cac aag ctg gaa tac aac      432
Asp Phe Lys Glu Asp Gly Asn Ile Leu Gly His Lys Leu Glu Tyr Asn
    130                 135                 140 ttt aac agc cac aac gtg tat att acc gcg gac aag cag aag aac ggt      480
Phe Asn Ser His Asn Val Tyr Ile Thr Ala Asp Lys Gln Lys Asn Gly
145                 150                 155                 160 atc aag gcg aac ttt aaa att cgt cac aac gtt gag ggt ggt ggt ggc      528
Ile Lys Ala Asn Phe Lys Ile Arg His Asn Val Glu Gly Gly Gly Gly
                165                 170                 175 agc ggt ggc ggt ggc agc ggt ggc ggt ggc agc ggg ccg gat tgc gcg      576
Ser Gly Gly Gly Gly Ser Gly Gly Gly Gly Ser Gly Pro Asp Cys Ala
            180                 185                 190
```

```
tac cac cgt ggc gaa ctg gtg tgg tgc acc ttt cat ggt ggc ggt ggc    624
Tyr His Arg Gly Glu Leu Val Trp Cys Thr Phe His Gly Gly Gly Gly
        195                 200                 205 agc ggt ggc ggt ggc agc ggt ggc ggt ggc agc gat ggt agc gtt cag    672
Ser Gly Gly Gly Gly Ser Gly Gly Gly Gly Ser Asp Gly Ser Val Gln
    210                 215                 220 ctg gcg gat cac tac cag caa aac acc ccg att ggt gat ggt ccg gtg    720
Leu Ala Asp His Tyr Gln Gln Asn Thr Pro Ile Gly Asp Gly Pro Val
225                 230                 235                 240 ctg ctg ccg gat aac cac tat ctg agc acc caa agc gtt ctg agc aag    768
Leu Leu Pro Asp Asn His Tyr Leu Ser Thr Gln Ser Val Leu Ser Lys
            245                 250                 255 gac ccg aac gag aaa cgt gat cac atg gtg ctg ctg gaa ttt gtt acc    816
Asp Pro Asn Glu Lys Arg Asp His Met Val Leu Leu Glu Phe Val Thr
        260                 265                 270 gcg gcg ggt att acc cac ggc atg gac gag ctg tac aaa ggt ggc ggt    864
Ala Ala Gly Ile Thr His Gly Met Asp Glu Leu Tyr Lys Gly Gly Gly
    275                 280                 285 ggc agc ggt ggc ggt ggc agc ggt ggc ggt ggc agc ggc ccg gat tgc    912
Gly Ser Gly Gly Gly Gly Ser Gly Gly Gly Gly Ser Gly Pro Asp Cys
290                 295                 300 gcg tat cac cgt ggc gaa ctg gtt tgg tgc acc ttc cac ggt ggc ggt    960
Ala Tyr His Arg Gly Glu Leu Val Trp Cys Thr Phe His Gly Gly Gly
305                 310                 315                 320 cat cac cac cac cac cac taa                                        981
His His His His His His
            325

<210> SEQ ID NO 49
<211> LENGTH: 326
<212> TYPE: PRT
<213> ORGANISM: Artificial
<220> FEATURE:
<223> OTHER INFORMATION: Synthetic Construct

<400> SEQUENCE: 49

Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Gly Gly Gly Gly
                165                 170                 175
```

```
Ser Gly Gly Gly Gly Ser Gly Gly Gly Ser Gly Pro Asp Cys Ala
            180                 185                 190

Tyr His Arg Gly Glu Leu Val Trp Cys Thr Phe His Gly Gly Gly
            195                 200                 205

Ser Gly Gly Gly Gly Ser Gly Gly Gly Ser Asp Gly Ser Val Gln
            210                 215                 220

Leu Ala Asp His Tyr Gln Gln Asn Thr Pro Ile Gly Asp Gly Pro Val
225                 230                 235                 240

Leu Leu Pro Asp Asn His Tyr Leu Ser Thr Gln Ser Val Leu Ser Lys
                245                 250                 255

Asp Pro Asn Glu Lys Arg Asp His Met Val Leu Leu Glu Phe Val Thr
                260                 265                 270

Ala Ala Gly Ile Thr His Gly Met Asp Glu Leu Tyr Lys Gly Gly Gly
            275                 280                 285

Gly Ser Gly Gly Gly Gly Ser Gly Gly Gly Ser Gly Pro Asp Cys
            290                 295                 300

Ala Tyr His Arg Gly Glu Leu Val Trp Cys Thr Phe His Gly Gly Gly
305                 310                 315                 320

His His His His His His
            325
```

<210> SEQ ID NO 50
<211> LENGTH: 16
<212> TYPE: PRT
<213> ORGANISM: Artificial
<220> FEATURE:
<223> OTHER INFORMATION: IgA binding peptide

<400> SEQUENCE: 50

```
His Gln Val Cys Leu Ser Tyr Arg Gly Arg Pro Val Cys Phe Ser Thr
1               5                   10                  15
```

<210> SEQ ID NO 51
<211> LENGTH: 17
<212> TYPE: PRT
<213> ORGANISM: Artificial
<220> FEATURE:
<223> OTHER INFORMATION: IgY binding peptide

<400> SEQUENCE: 51

```
Arg Ser Val Cys Val Trp Thr Ala Val Thr Gly Trp Asp Cys Arg Asn
1               5                   10                  15

Asp
```

<210> SEQ ID NO 52
<211> LENGTH: 714
<212> TYPE: DNA
<213> ORGANISM: Artificial
<220> FEATURE:
<223> OTHER INFORMATION: Superfolder yellow fluorescent protein
<220> FEATURE:
<221> NAME/KEY: CDS
<222> LOCATION: (1)..(714)

<400> SEQUENCE: 52

```
atg cgt aaa ggc gag gaa ctg ttc acc ggt gtg gtt ccg atc ctg gtg      48
Met Arg Lys Gly Glu Glu Leu Phe Thr Gly Val Val Pro Ile Leu Val
1               5                   10                  15 gag ctg gac ggc gat gtt aac ggt cac aag ttt agc gtg cgt ggt gag      96
Glu Leu Asp Gly Asp Val Asn Gly His Lys Phe Ser Val Arg Gly Glu
            20                  25                  30
```

```
ggc gaa ggt gac gcg acc aac ggc aag ctg acc ctg aaa ttc att tgc      144
Gly Glu Gly Asp Ala Thr Asn Gly Lys Leu Thr Leu Lys Phe Ile Cys
         35                  40                  45 acc acc ggt aaa ctg ccg gtg ccg tgg ccg acc ctg gtt acc acc ctg      192
Thr Thr Gly Lys Leu Pro Val Pro Trp Pro Thr Leu Val Thr Thr Leu
 50                  55                  60 acc tac ggt gtg cag tgc ttt gcg cgt tat ccg gac cac atg aag caa      240
Thr Tyr Gly Val Gln Cys Phe Ala Arg Tyr Pro Asp His Met Lys Gln
 65                  70                  75                  80 cac gat ttc ttt aaa agc gcg atg ccg gag ggc tac gtt cag gaa cgt      288
His Asp Phe Phe Lys Ser Ala Met Pro Glu Gly Tyr Val Gln Glu Arg
             85                  90                  95 acc atc agc ttc aag gac gat ggt acc tat aaa acc cgt gcg gaa gtg      336
Thr Ile Ser Phe Lys Asp Asp Gly Thr Tyr Lys Thr Arg Ala Glu Val
         100                 105                 110 aag ttt gaa ggc gat acc ctg gtt aac cgt atc gag ctg aag ggt att      384
Lys Phe Glu Gly Asp Thr Leu Val Asn Arg Ile Glu Leu Lys Gly Ile
     115                 120                 125 gac ttc aaa gaa gat ggc aac atc ctg ggt cac aag ctg gaa tac aac      432
Asp Phe Lys Glu Asp Gly Asn Ile Leu Gly His Lys Leu Glu Tyr Asn
130                 135                 140 ttt aac agc cac aac gtg tat att acc gcg gac aag cag aag aac ggt      480
Phe Asn Ser His Asn Val Tyr Ile Thr Ala Asp Lys Gln Lys Asn Gly
145                 150                 155                 160 atc aag gcg aac ttt aaa att cgt cac aac gtt gag gat ggt agc gtt      528
Ile Lys Ala Asn Phe Lys Ile Arg His Asn Val Glu Asp Gly Ser Val
                165                 170                 175 cag ctg gcg gat cac tac cag caa aac acc ccg att ggt gat ggt ccg      576
Gln Leu Ala Asp His Tyr Gln Gln Asn Thr Pro Ile Gly Asp Gly Pro
            180                 185                 190 gtg ctg ctg ccg gat aac cac tat ctg agc tat caa agc gtt ctg agc      624
Val Leu Leu Pro Asp Asn His Tyr Leu Ser Tyr Gln Ser Val Leu Ser
        195                 200                 205 aag gac ccg aac gag aaa cgt gat cac atg gtg ctg ctg gaa ttt gtt      672
Lys Asp Pro Asn Glu Lys Arg Asp His Met Val Leu Leu Glu Phe Val
210                 215                 220 acc gcg gcg ggc att acc cac ggt atg gac gag ctg tac aaa             714
Thr Ala Ala Gly Ile Thr His Gly Met Asp Glu Leu Tyr Lys
225                 230                 235

<210> SEQ ID NO 53
<211> LENGTH: 238
<212> TYPE: PRT
<213> ORGANISM: Artificial
<220> FEATURE:
<223> OTHER INFORMATION: Synthetic Construct

<400> SEQUENCE: 53

Met Arg Lys Gly Glu Glu Leu Phe Thr Gly Val Val Pro Ile Leu Val
 1               5                  10                  15

Glu Leu Asp Gly Asp Val Asn Gly His Lys Phe Ser Val Arg Gly Glu
             20                  25                  30

Gly Glu Gly Asp Ala Thr Asn Gly Lys Leu Thr Leu Lys Phe Ile Cys
         35                  40                  45

Thr Thr Gly Lys Leu Pro Val Pro Trp Pro Thr Leu Val Thr Thr Leu
 50                  55                  60

Thr Tyr Gly Val Gln Cys Phe Ala Arg Tyr Pro Asp His Met Lys Gln
 65                  70                  75                  80

His Asp Phe Phe Lys Ser Ala Met Pro Glu Gly Tyr Val Gln Glu Arg
             85                  90                  95
```

```
Thr Ile Ser Phe Lys Asp Asp Gly Thr Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Val Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 54
<211> LENGTH: 936
<212> TYPE: DNA
<213> ORGANISM: Artificial
<220> FEATURE:
<223> OTHER INFORMATION: IgG binding peptide-fusion protein
<220> FEATURE:
<221> NAME/KEY: CDS
<222> LOCATION: (1)..(936)

<400> SEQUENCE: 54 atg cgt aaa ggc gag gaa ctg ttc acc ggt gtg gtt ccg atc ctg gtg      48
Met Arg Lys Gly Glu Glu Leu Phe Thr Gly Val Val Pro Ile Leu Val
1               5                   10                  15 gag ctg gac ggc gat gtt aac ggt cac aag ttt agc gtg cgt ggt gag      96
Glu Leu Asp Gly Asp Val Asn Gly His Lys Phe Ser Val Arg Gly Glu
            20                  25                  30 ggc gaa ggt gac gcg acc aac ggc aag ctg acc ctg aaa ttc att tgc     144
Gly Glu Gly Asp Ala Thr Asn Gly Lys Leu Thr Leu Lys Phe Ile Cys
        35                  40                  45 acc acc ggt aaa ctg ccg gtg ccg tgg ccg acc ctg gtt acc acc ctg     192
Thr Thr Gly Lys Leu Pro Val Pro Trp Pro Thr Leu Val Thr Thr Leu
50                  55                  60 acc tac ggt gtg cag tgc ttt gcg cgt tat ccg gac cac atg aag caa     240
Thr Tyr Gly Val Gln Cys Phe Ala Arg Tyr Pro Asp His Met Lys Gln
65                  70                  75                  80 cac gat ttc ttt aaa agc gcg atg ccg gag ggc tac gtt cag gaa cgt     288
His Asp Phe Phe Lys Ser Ala Met Pro Glu Gly Tyr Val Gln Glu Arg
                85                  90                  95 acc atc agc ttc aag gac gat ggt acc tat aaa acc cgt gcg gaa gtg     336
Thr Ile Ser Phe Lys Asp Asp Gly Thr Tyr Lys Thr Arg Ala Glu Val
            100                 105                 110 aag ttt gaa ggc gat acc ctg gtt aac cgt atc gag ctg aag ggt att     384
Lys Phe Glu Gly Asp Thr Leu Val Asn Arg Ile Glu Leu Lys Gly Ile
        115                 120                 125 gac ttc aaa gaa gat ggc aac atc ctg ggt cac aag ctg gaa tac aac     432
Asp Phe Lys Glu Asp Gly Asn Ile Leu Gly His Lys Leu Glu Tyr Asn
130                 135                 140 ttt aac agc cac aac gtg tat att acc gcg gac aag cag aag aac ggt     480
Phe Asn Ser His Asn Val Tyr Ile Thr Ala Asp Lys Gln Lys Asn Gly
```

|  |  |  |  |  |  |  |  |  |  | 145 |  |  |  | 150 |  |  |  | 155 |  |  |  | 160 |  |  |
|---|---|---|---|---|---|---|---|---|---|---|---|---|---|---|---|---|---|---|---|---|---|---|---|---|

```
atc aag gcg aac ttt aaa att cgt cac aac gtt gag ggt ggc ggt ggc         528
Ile Lys Ala Asn Phe Lys Ile Arg His Asn Val Glu Gly Gly Gly Gly
                165                 170                 175 agc ggt ggt ggc ggt agc ggt ccg gat tgc gcg tac cac cgt ggt gaa         576
Ser Gly Gly Gly Gly Ser Gly Pro Asp Cys Ala Tyr His Arg Gly Glu
            180                 185                 190 ctg gtg tgg tgc acc ttt cat ggc ggc ggt agc ggc ggt ggc ggt             624
Leu Val Trp Cys Thr Phe His Gly Gly Gly Ser Gly Gly Gly Gly
        195                 200                 205 agc gat ggt agc gtt cag ctg gcg gat cac tac cag caa aac acc ccg         672
Ser Asp Gly Ser Val Gln Leu Ala Asp His Tyr Gln Gln Asn Thr Pro
    210                 215                 220 att ggt gat ggt ccg gtg ctg ctg ccg gat aac cac tat ctg agc tat         720
Ile Gly Asp Gly Pro Val Leu Leu Pro Asp Asn His Tyr Leu Ser Tyr
225                 230                 235                 240 caa agc gtt ctg agc aag gac ccg aac gag aaa cgt gat cac atg gtg         768
Gln Ser Val Leu Ser Lys Asp Pro Asn Glu Lys Arg Asp His Met Val
                245                 250                 255 ctg ctg gaa ttt gtt acc gcg gcg ggc att acc cac ggt atg gac gag         816
Leu Leu Glu Phe Val Thr Ala Ala Gly Ile Thr His Gly Met Asp Glu
            260                 265                 270 ctg tac aaa ggc ggt ggc ggt agc ggc ggt ggc ggt agc ggg ccg gat         864
Leu Tyr Lys Gly Gly Gly Gly Ser Gly Gly Gly Gly Ser Gly Pro Asp
        275                 280                 285 tgc gcg tat cac cgt ggt gaa ctg gtt tgg tgt act ttt cat ggc ggt         912
Cys Ala Tyr His Arg Gly Glu Leu Val Trp Cys Thr Phe His Gly Gly
    290                 295                 300 ggc cac cac cac cac cac cac taa                                         936
Gly His His His His His His
305                 310
```

<210> SEQ ID NO 55
<211> LENGTH: 311
<212> TYPE: PRT
<213> ORGANISM: Artificial
<220> FEATURE:
<223> OTHER INFORMATION: Synthetic Construct

<400> SEQUENCE: 55

```
Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140
```

```
Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Gly Gly Gly Gly
                165                 170                 175

Ser Gly Gly Gly Gly Ser Gly Pro Asp Cys Ala Tyr His Arg Gly Glu
            180                 185                 190

Leu Val Trp Cys Thr Phe His Gly Gly Gly Ser Gly Gly Gly Gly
        195                 200                 205

Ser Asp Gly Ser Val Gln Leu Ala Asp His Tyr Gln Gln Asn Thr Pro
    210                 215                 220

Ile Gly Asp Gly Pro Val Leu Leu Pro Asp Asn His Tyr Leu Ser Tyr
225                 230                 235                 240

Gln Ser Val Leu Ser Lys Asp Pro Asn Glu Lys Arg Asp His Met Val
                245                 250                 255

Leu Leu Glu Phe Val Thr Ala Ala Gly Ile Thr His Gly Met Asp Glu
                260                 265                 270

Leu Tyr Lys Gly Gly Gly Gly Ser Gly Gly Gly Gly Ser Gly Pro Asp
        275                 280                 285

Cys Ala Tyr His Arg Gly Glu Leu Val Trp Cys Thr Phe His Gly Gly
    290                 295                 300

Gly His His His His His His
305                 310

<210> SEQ ID NO 56
<211> LENGTH: 930
<212> TYPE: DNA
<213> ORGANISM: Artificial
<220> FEATURE:
<223> OTHER INFORMATION: IgA binding peptide-fusion protein
<220> FEATURE:
<221> NAME/KEY: CDS
<222> LOCATION: (1)..(930)

<400> SEQUENCE: 56 atg cgt aaa ggc gag gaa ctg ttc acc ggc gtg gtt ccg atc ctg gtg      48
Met Arg Lys Gly Glu Glu Leu Phe Thr Gly Val Val Pro Ile Leu Val
1               5                   10                  15 gag ctg gac ggt gat gtt aac ggc cac aag ttt agc gtg cgt ggc gag      96
Glu Leu Asp Gly Asp Val Asn Gly His Lys Phe Ser Val Arg Gly Glu
            20                  25                  30 ggt gaa ggt gat gcg acc aac ggc aag ctg acc ctg aaa ttc att tgc     144
Gly Glu Gly Asp Ala Thr Asn Gly Lys Leu Thr Leu Lys Phe Ile Cys
        35                  40                  45 acc acc ggt aaa ctg ccg gtg ccg tgg ccg acc ctg gtt acc acc ctg     192
Thr Thr Gly Lys Leu Pro Val Pro Trp Pro Thr Leu Val Thr Thr Leu
    50                  55                  60 acc tac ggt gtg cag tgc ttt gcg cgt tat ccg gac cac atg aag caa     240
Thr Tyr Gly Val Gln Cys Phe Ala Arg Tyr Pro Asp His Met Lys Gln
65                  70                  75                  80 cac gat ttc ttt aaa agc gcg atg ccg gag ggt tac gtt cag gaa cgt     288
His Asp Phe Phe Lys Ser Ala Met Pro Glu Gly Tyr Val Gln Glu Arg
                85                  90                  95 acc atc agc ttc aag gac gat ggc acc tat aaa acc cgt gcg gaa gtg     336
Thr Ile Ser Phe Lys Asp Asp Gly Thr Tyr Lys Thr Arg Ala Glu Val
            100                 105                 110 aag ttt gaa ggt gac acc ctg gtt aac cgt atc gag ctg aag ggc att     384
Lys Phe Glu Gly Asp Thr Leu Val Asn Arg Ile Glu Leu Lys Gly Ile
        115                 120                 125 gac ttc aaa gaa gat ggt aac atc ctg ggc cac aag ctg gag tac aac     432
Asp Phe Lys Glu Asp Gly Asn Ile Leu Gly His Lys Leu Glu Tyr Asn
```

```
                Asp Phe Lys Glu Asp Gly Asn Ile Leu Gly His Lys Leu Glu Tyr Asn
                    130                 135                 140 ttt aac agc cac aac gtg tat att acc gcg gat aag cag aaa aac ggt        480
Phe Asn Ser His Asn Val Tyr Ile Thr Ala Asp Lys Gln Lys Asn Gly
145                 150                 155                 160 atc aag gcg aac ttt aaa att cgt cac aac gtt gaa ggt ggt ggt ggc        528
Ile Lys Ala Asn Phe Lys Ile Arg His Asn Val Glu Gly Gly Gly Gly
                    165                 170                 175 agc ggt ggc ggt ggc agc cac caa gtg tgc ctg agc tac cgt ggt cgt        576
Ser Gly Gly Gly Gly Ser His Gln Val Cys Leu Ser Tyr Arg Gly Arg
                180                 185                 190 ccg gtt tgc ttt agc acc ggt ggc ggt ggc agc ggt ggc ggt ggc agc        624
Pro Val Cys Phe Ser Thr Gly Gly Gly Gly Ser Gly Gly Gly Gly Ser
                    195                 200                 205 gat ggc agc gtt cag ctg gcg gat cac tac cag caa aac acc ccg att        672
Asp Gly Ser Val Gln Leu Ala Asp His Tyr Gln Gln Asn Thr Pro Ile
210                 215                 220 ggt gat ggt ccg gtg ctg ctg ccg gat aac cac tat ctg agc acc caa        720
Gly Asp Gly Pro Val Leu Leu Pro Asp Asn His Tyr Leu Ser Thr Gln
225                 230                 235                 240 agc gtt ctg agc aag gac ccg aac gag aaa cgt gat cac atg gtg ctg        768
Ser Val Leu Ser Lys Asp Pro Asn Glu Lys Arg Asp His Met Val Leu
                    245                 250                 255 ctg gaa ttt gtt acc gcg gcg ggt att acc cac ggc atg gat gaa ctg        816
Leu Glu Phe Val Thr Ala Ala Gly Ile Thr His Gly Met Asp Glu Leu
                    260                 265                 270 tac aaa ggt ggc ggt ggc agc ggt ggc ggt ggc agc cat caa gtg tgc        864
Tyr Lys Gly Gly Gly Gly Ser Gly Gly Gly Gly Ser His Gln Val Cys
                275                 280                 285 ctg agc tat cgc ggc cgt ccg gtt tgc ttc agc acc ggt ggc ggt cat        912
Leu Ser Tyr Arg Gly Arg Pro Val Cys Phe Ser Thr Gly Gly Gly His
290                 295                 300 cac cac cac cac cac taa                                                930
His His His His His
305
```

<210> SEQ ID NO 57
<211> LENGTH: 309
<212> TYPE: PRT
<213> ORGANISM: Artificial
<220> FEATURE:
<223> OTHER INFORMATION: Synthetic Construct

<400> SEQUENCE: 57

```
Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
                20                  25                  30

Gly Glu Gly Asp Ala Thr Asn Gly Lys Leu Thr Leu Lys Phe Ile Cys
            35                  40                  45

Thr Thr Gly Lys Leu Pro Val Pro Trp Pro Thr Leu Val Thr Thr Leu
        50                  55                  60

Thr Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
                100                 105                 110

Lys Phe Glu Gly Asp Thr Leu Val Asn Arg Ile Glu Leu Lys Gly Ile
```

```
                115                 120                 125
Asp Phe Lys Glu Asp Gly Asn Ile Leu Gly His Lys Leu Glu Tyr Asn
        130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Gly Gly Gly Gly
                165                 170                 175

Ser Gly Gly Gly Gly Ser His Gln Val Cys Leu Ser Tyr Arg Gly Arg
            180                 185                 190

Pro Val Cys Phe Ser Thr Gly Gly Gly Ser Gly Gly Gly Gly Ser
                195                 200                 205

Asp Gly Ser Val Gln Leu Ala Asp His Tyr Gln Gln Asn Thr Pro Ile
        210                 215                 220

Gly Asp Gly Pro Val Leu Leu Pro Asp Asn His Tyr Leu Ser Thr Gln
225                 230                 235                 240

Ser Val Leu Ser Lys Asp Pro Asn Glu Lys Arg Asp His Met Val Leu
                245                 250                 255

Leu Glu Phe Val Thr Ala Ala Gly Ile Thr His Gly Met Asp Glu Leu
            260                 265                 270

Tyr Lys Gly Gly Gly Ser Gly Gly Gly Gly Ser His Gln Val Cys
        275                 280                 285

Leu Ser Tyr Arg Gly Arg Pro Val Cys Phe Ser Thr Gly Gly Gly His
        290                 295                 300

His His His His His
305

<210> SEQ ID NO 58
<211> LENGTH: 936
<212> TYPE: DNA
<213> ORGANISM: Artificial
<220> FEATURE:
<223> OTHER INFORMATION: IgY binding peptide-fusion protein
<220> FEATURE:
<221> NAME/KEY: CDS
<222> LOCATION: (1)..(936)

<400> SEQUENCE: 58 atg cgt aaa ggc gag gaa ctg ttc acc ggc gtg gtt ccg atc ctg gtg      48
Met Arg Lys Gly Glu Glu Leu Phe Thr Gly Val Val Pro Ile Leu Val
1               5                   10                  15 gag ctg gac ggt gat gtt aac ggc cac aag ttt agc gtg cgt ggc gag      96
Glu Leu Asp Gly Asp Val Asn Gly His Lys Phe Ser Val Arg Gly Glu
                20                  25                  30 ggt gaa ggt gat gcg acc aac ggc aag ctg acc ctg aaa ttc att tgc     144
Gly Glu Gly Asp Ala Thr Asn Gly Lys Leu Thr Leu Lys Phe Ile Cys
            35                  40                  45 acc acc ggt aaa ctg ccg gtg ccg tgg ccg acc ctg gtt acc acc ctg     192
Thr Thr Gly Lys Leu Pro Val Pro Trp Pro Thr Leu Val Thr Thr Leu
        50                  55                  60 acc tac ggt gtg cag tgc ttt gcg cgt tat ccg gac cac atg aag caa     240
Thr Tyr Gly Val Gln Cys Phe Ala Arg Tyr Pro Asp His Met Lys Gln
65                  70                  75                  80 cac gat ttc ttt aaa agc gcg atg ccg gag ggt tac gtt cag gaa cgt     288
His Asp Phe Phe Lys Ser Ala Met Pro Glu Gly Tyr Val Gln Glu Arg
                85                  90                  95 acc atc agc ttc aag gac gat ggc acc tat aaa acc cgt gcg gaa gtg     336
Thr Ile Ser Phe Lys Asp Asp Gly Thr Tyr Lys Thr Arg Ala Glu Val
                100                 105                 110
```

| | |
|---|---|
| aag ttt gaa ggt gac acc ctg gtt aac cgt atc gag ctg aag ggc att<br>Lys Phe Glu Gly Asp Thr Leu Val Asn Arg Ile Glu Leu Lys Gly Ile<br>        115                      120                  125 | 384 |
| gac ttc aaa gaa gat ggt aac atc ctg ggc cac aag ctg gag tac aac<br>Asp Phe Lys Glu Asp Gly Asn Ile Leu Gly His Lys Leu Glu Tyr Asn<br>130                      135                      140 | 432 |
| ttt aac agc cac aac gtg tat att acc gcg gat aag cag aag aac ggt<br>Phe Asn Ser His Asn Val Tyr Ile Thr Ala Asp Lys Gln Lys Asn Gly<br>145                      150                      155                  160 | 480 |
| atc aag gcg aac ttc aaa att cgt cac aac gtg gaa ggt ggc ggt ggc<br>Ile Lys Ala Asn Phe Lys Ile Arg His Asn Val Glu Gly Gly Gly Gly<br>                    165                      170                      175 | 528 |
| agc ggt ggc ggt ggc agc cgt agc gtg tgc gtt tgg acc gcg gtt acc<br>Ser Gly Gly Gly Gly Ser Arg Ser Val Cys Val Trp Thr Ala Val Thr<br>                  180                      185                      190 | 576 |
| ggt tgg gac tgc cgt aac gat ggt ggt ggc agc ggt ggc ggt ggc<br>Gly Trp Asp Cys Arg Asn Asp Gly Gly Gly Ser Gly Gly Gly Gly<br>                  195                      200                      205 | 624 |
| agc gat ggc agc gtt cag ctg gcg gat cac tac cag caa aac acc ccg<br>Ser Asp Gly Ser Val Gln Leu Ala Asp His Tyr Gln Gln Asn Thr Pro<br>210                      215                      220 | 672 |
| att ggt gat ggt ccg gtg ctg ctg ccg gat aac cac tat ctg agc acc<br>Ile Gly Asp Gly Pro Val Leu Leu Pro Asp Asn His Tyr Leu Ser Thr<br>225                      230                      235                  240 | 720 |
| caa agc gtt ctg agc aag gac ccg aac gag aaa cgt gat cac atg gtg<br>Gln Ser Val Leu Ser Lys Asp Pro Asn Glu Lys Arg Asp His Met Val<br>                    245                      250                      255 | 768 |
| ctg ctg gaa ttt gtt acc gcg gcg ggt att acc cac ggc atg gat gaa<br>Leu Leu Glu Phe Val Thr Ala Ala Gly Ile Thr His Gly Met Asp Glu<br>                    260                      265                      270 | 816 |
| ctg tac aaa ggt ggc ggt ggc agc ggt ggc ggt ggc agc cgt agc gtg<br>Leu Tyr Lys Gly Gly Gly Gly Ser Gly Gly Gly Gly Ser Arg Ser Val<br>                    275                      280                      285 | 864 |
| tgt gtg tgg acc gcg gtg acc ggc tgg gat tgc cgc aat gat ggt ggc<br>Cys Val Trp Thr Ala Val Thr Gly Trp Asp Cys Arg Asn Asp Gly Gly<br>                    290                      295                      300 | 912 |
| ggt cat cac cac cac cac cac taa<br>Gly His His His His His His<br>305                      310 | 936 |

<210> SEQ ID NO 59
<211> LENGTH: 311
<212> TYPE: PRT
<213> ORGANISM: Artificial
<220> FEATURE:
<223> OTHER INFORMATION: Synthetic Construct

<400> SEQUENCE: 59

Met Arg Lys Gly Glu Glu Leu Phe Thr Gly Val Val Pro Ile Leu Val
1                  5                    10                    15

Glu Leu Asp Gly Asp Val Asn Gly His Lys Phe Ser Val Arg Gly Glu
                  20                      25                      30

Gly Glu Gly Asp Ala Thr Asn Gly Lys Leu Thr Leu Lys Phe Ile Cys
                  35                      40                      45

Thr Thr Gly Lys Leu Pro Val Pro Trp Pro Thr Leu Val Thr Thr Leu
50                      55                      60

Thr Tyr Gly Val Gln Cys Phe Ala Arg Tyr Pro Asp His Met Lys Gln
65                    70                    75                      80

His Asp Phe Phe Lys Ser Ala Met Pro Glu Gly Tyr Val Gln Glu Arg
                  85                      90                      95

```
Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Gly Gly Gly
                165                 170                 175

Ser Gly Gly Gly Ser Arg Ser Val Cys Val Trp Thr Ala Val Thr
            180                 185                 190

Gly Trp Asp Cys Arg Asn Asp Gly Gly Gly Ser Gly Gly Gly Gly
        195                 200                 205

Ser Asp Gly Ser Val Gln Leu Ala Asp His Tyr Gln Gln Asn Thr Pro
210                 215                 220

Ile Gly Asp Gly Pro Val Leu Leu Pro Asp Asn His Tyr Leu Ser Thr
225                 230                 235                 240

Gln Ser Val Leu Ser Lys Asp Pro Asn Glu Lys Arg Asp His Met Val
                245                 250                 255

Leu Leu Glu Phe Val Thr Ala Ala Gly Ile Thr His Gly Met Asp Glu
            260                 265                 270

Leu Tyr Lys Gly Gly Gly Gly Ser Gly Gly Gly Gly Ser Arg Ser Val
        275                 280                 285

Cys Val Trp Thr Ala Val Thr Gly Trp Asp Cys Arg Asn Asp Gly Gly
        290                 295                 300

Gly His His His His His His
305                 310

<210> SEQ ID NO 60
<211> LENGTH: 678
<212> TYPE: DNA
<213> ORGANISM: Discosoma sp.
<220> FEATURE:
<221> NAME/KEY: CDS
<222> LOCATION: (1)..(678)

<400> SEQUENCE: 60 atg agg tct tcc aag aat gtt atc aag gag ttc atg agg ttt aag gtt      48
Met Arg Ser Ser Lys Asn Val Ile Lys Glu Phe Met Arg Phe Lys Val
1               5                   10                  15 cgc atg gaa gga acg gtc aat ggg cac gag ttt gaa ata gaa ggc gaa      96
Arg Met Glu Gly Thr Val Asn Gly His Glu Phe Glu Ile Glu Gly Glu
                20                  25                  30 gga gag ggg agg cca tac gaa ggc cac aat acc gta aag ctt aag gta     144
Gly Glu Gly Arg Pro Tyr Glu Gly His Asn Thr Val Lys Leu Lys Val
            35                  40                  45 acc aag ggg gga cct ttg cca ttt gct tgg gat att ttg tca cca caa     192
Thr Lys Gly Gly Pro Leu Pro Phe Ala Trp Asp Ile Leu Ser Pro Gln
        50                  55                  60 ttt cag tat gga agc aag gta tat gtc aag cac cct gcc gac ata cca     240
Phe Gln Tyr Gly Ser Lys Val Tyr Val Lys His Pro Ala Asp Ile Pro
65                  70                  75                  80 gac tat aaa aag ctg tca ttt cct gaa gga ttt aaa tgg gaa agg gtc     288
Asp Tyr Lys Lys Leu Ser Phe Pro Glu Gly Phe Lys Trp Glu Arg Val
                85                  90                  95 atg aac ttt gaa gac ggt ggc gtc gtt act gta acc cag gat tcc agt     336
```

```
Met Asn Phe Glu Asp Gly Gly Val Val Thr Val Thr Gln Asp Ser Ser
            100                 105                 110 ttg cag gat ggc tgt ttc atc tac aag gtc aag ttc att ggc gtg aac      384
Leu Gln Asp Gly Cys Phe Ile Tyr Lys Val Lys Phe Ile Gly Val Asn
        115                 120                 125 ttt cct tcc gat gga cct gtt atg caa aag aag aca atg ggc tgg gaa      432
Phe Pro Ser Asp Gly Pro Val Met Gln Lys Lys Thr Met Gly Trp Glu
130                 135                 140 gcc agc act gag cgt ttg tat cct cgt gat ggc gtg ttg aaa gga gag      480
Ala Ser Thr Glu Arg Leu Tyr Pro Arg Asp Gly Val Leu Lys Gly Glu
145                 150                 155                 160 att cat aag gct ctg aag ctg aaa gac ggt ggt cat tac cta gtt gaa      528
Ile His Lys Ala Leu Lys Leu Lys Asp Gly Gly His Tyr Leu Val Glu
                165                 170                 175 ttc aaa agt att tac atg gca aag aag cct gtg cag cta cca ggg tac      576
Phe Lys Ser Ile Tyr Met Ala Lys Lys Pro Val Gln Leu Pro Gly Tyr
            180                 185                 190 tac tat gtt gac tcc aaa ctg gat ata aca agc cac aac gaa gac tat      624
Tyr Tyr Val Asp Ser Lys Leu Asp Ile Thr Ser His Asn Glu Asp Tyr
        195                 200                 205 aca atc gtt gag cag tat gaa aga acc gag gga cgc cac cat ctg ttc      672
Thr Ile Val Glu Gln Tyr Glu Arg Thr Glu Gly Arg His His Leu Phe
    210                 215                 220 ctt taa                                                              678
Leu
225

<210> SEQ ID NO 61
<211> LENGTH: 225
<212> TYPE: PRT
<213> ORGANISM: Discosoma sp.

<400> SEQUENCE: 61

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190
```

```
Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 62
<211> LENGTH: 2
<212> TYPE: PRT
<213> ORGANISM: Artificial
<220> FEATURE:
<223> OTHER INFORMATION: Synthetic peptide

<400> SEQUENCE: 62

Trp Trp
1

<210> SEQ ID NO 63
<211> LENGTH: 4
<212> TYPE: PRT
<213> ORGANISM: Artificial
<220> FEATURE:
<223> OTHER INFORMATION: Synthetic peptide

<400> SEQUENCE: 63

Tyr Phe Arg His
1

<210> SEQ ID NO 64
<211> LENGTH: 4
<212> TYPE: PRT
<213> ORGANISM: Artificial
<220> FEATURE:
<223> OTHER INFORMATION: Synthetic peptide

<400> SEQUENCE: 64

Gln Asp Glu Ser
1

<210> SEQ ID NO 65
<211> LENGTH: 4
<212> TYPE: PRT
<213> ORGANISM: Artificial
<220> FEATURE:
<223> OTHER INFORMATION: Synthetic peptide

<400> SEQUENCE: 65

Ala Pro Ala Arg
1

<210> SEQ ID NO 66
<211> LENGTH: 4
<212> TYPE: PRT
<213> ORGANISM: Artificial
<220> FEATURE:
<223> OTHER INFORMATION: Synthetic peptide

<400> SEQUENCE: 66

Arg Arg Gly Trp
1

<210> SEQ ID NO 67
<211> LENGTH: 5
<212> TYPE: PRT
<213> ORGANISM: Artificial
```

```
<220> FEATURE:
<223> OTHER INFORMATION: Synthetic peptide

<400> SEQUENCE: 67

Met Glu Glu Val Asp
1               5

<210> SEQ ID NO 68
<211> LENGTH: 6
<212> TYPE: PRT
<213> ORGANISM: Artificial
<220> FEATURE:
<223> OTHER INFORMATION: Synthetic peptide

<400> SEQUENCE: 68

Phe Leu Leu Val Pro Leu
1               5

<210> SEQ ID NO 69
<211> LENGTH: 6
<212> TYPE: PRT
<213> ORGANISM: Artificial
<220> FEATURE:
<223> OTHER INFORMATION: Synthetic peptide

<400> SEQUENCE: 69

His Trp Arg Gly Trp Val
1               5

<210> SEQ ID NO 70
<211> LENGTH: 6
<212> TYPE: PRT
<213> ORGANISM: Artificial
<220> FEATURE:
<223> OTHER INFORMATION: Synthetic peptide

<400> SEQUENCE: 70

His Tyr Phe Lys Phe Asp
1               5

<210> SEQ ID NO 71
<211> LENGTH: 6
<212> TYPE: PRT
<213> ORGANISM: Artificial
<220> FEATURE:
<223> OTHER INFORMATION: Synthetic peptide

<400> SEQUENCE: 71

His Phe Arg Arg His Leu
1               5

<210> SEQ ID NO 72
<211> LENGTH: 6
<212> TYPE: PRT
<213> ORGANISM: Artificial
<220> FEATURE:
<223> OTHER INFORMATION: Synthetic peptide

<400> SEQUENCE: 72

Phe His Glu Asn Trp Ser
1               5

<210> SEQ ID NO 73
<211> LENGTH: 6
<212> TYPE: PRT
<213> ORGANISM: Artificial
<220> FEATURE:
```

```
<223> OTHER INFORMATION: Synthetic peptide

<400> SEQUENCE: 73

Trp His Trp Arg Lys Arg
1               5

<210> SEQ ID NO 74
<211> LENGTH: 6
<212> TYPE: PRT
<213> ORGANISM: Artificial
<220> FEATURE:
<223> OTHER INFORMATION: Synthetic peptide

<400> SEQUENCE: 74

Tyr Tyr Trp Leu His His
1               5

<210> SEQ ID NO 75
<211> LENGTH: 6
<212> TYPE: PRT
<213> ORGANISM: Artificial
<220> FEATURE:
<223> OTHER INFORMATION: Synthetic peptide

<400> SEQUENCE: 75

Arg Leu Arg Ser Phe Tyr
1               5

<210> SEQ ID NO 76
<211> LENGTH: 7
<212> TYPE: PRT
<213> ORGANISM: Artificial
<220> FEATURE:
<223> OTHER INFORMATION: Synthetic peptide

<400> SEQUENCE: 76

Lys His Arg Phe Asn Lys Asp
1               5

<210> SEQ ID NO 77
<211> LENGTH: 8
<212> TYPE: PRT
<213> ORGANISM: Artificial
<220> FEATURE:
<223> OTHER INFORMATION: Synthetic peptide

<400> SEQUENCE: 77

Phe Tyr Trp His Cys Leu Asp Glu
1               5

<210> SEQ ID NO 78
<211> LENGTH: 8
<212> TYPE: PRT
<213> ORGANISM: Artificial
<220> FEATURE:
<223> OTHER INFORMATION: Synthetic peptide

<400> SEQUENCE: 78

Phe Tyr Cys His Trp Ala Leu Glu
1               5

<210> SEQ ID NO 79
<211> LENGTH: 8
<212> TYPE: PRT
<213> ORGANISM: Artificial
<220> FEATURE:
<223> OTHER INFORMATION: Synthetic peptide
```

<400> SEQUENCE: 79

Phe Tyr Cys His Thr Ile Asp Glu
1               5

<210> SEQ ID NO 80
<211> LENGTH: 8
<212> TYPE: PRT
<213> ORGANISM: Artificial
<220> FEATURE:
<223> OTHER INFORMATION: Synthetic peptide

<400> SEQUENCE: 80

Asn Lys Phe Arg Gly Lys Tyr Lys
1               5

<210> SEQ ID NO 81
<211> LENGTH: 8
<212> TYPE: PRT
<213> ORGANISM: Artificial
<220> FEATURE:
<223> OTHER INFORMATION: Synthetic peptide

<400> SEQUENCE: 81

Asn Ala Arg Lys Phe Tyr Lys Gly
1               5

<210> SEQ ID NO 82
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: misc_feature
<222> LOCATION: (1)..(3)
<223> OTHER INFORMATION: At least one X is present and up to 2 may be
      absent; if present, X is independently an amino acid residue other
      than cysteine
<220> FEATURE:
<221> NAME/KEY: misc_feature
<222> LOCATION: (5)..(5)
<223> OTHER INFORMATION: X is independently an amino acid residue other
      than cysteine
<220> FEATURE:
<221> NAME/KEY: misc_feature
<222> LOCATION: (7)..(7)
<223> OTHER INFORMATION: X is an arginine residue, a lysine residue, a
      leucine residue, or an asparagine residue
<220> FEATURE:
<221> NAME/KEY: misc_feature
<222> LOCATION: (9)..(9)
<223> OTHER INFORMATION: X is a glutamic acid residue or an asparagine
      residue
<220> FEATURE:
<221> NAME/KEY: misc_feature
<222> LOCATION: (14)..(16)
<223> OTHER INFORMATION: At least one X is present and up to 2 may be
      absent; if present, X is independently an amino acid residue other
      than cysteine

<400> SEQUENCE: 82

Xaa Xaa Xaa Cys Xaa His Xaa Gly Xaa Leu Val Trp Cys Xaa Xaa Xaa
1               5                   10                  15

<210> SEQ ID NO 83
<211> LENGTH: 17

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: misc_feature
<222> LOCATION: (1)..(3)
<223> OTHER INFORMATION: At least one X is present and up to 2 may be
      absent; if present, X is independently an amino acid residue other
      than cysteine
<220> FEATURE:
<221> NAME/KEY: misc_feature
<222> LOCATION: (5)..(5)
<223> OTHER INFORMATION: X is independently an amino acid residue other
      than cysteine
<220> FEATURE:
<221> NAME/KEY: misc_feature
<222> LOCATION: (8)..(8)
<223> OTHER INFORMATION: X is an arginine residue, a lysine residue, a
      leucine residue, or an asparagine residue
<220> FEATURE:
<221> NAME/KEY: misc_feature
<222> LOCATION: (15)..(17)
<223> OTHER INFORMATION: At least one X is present and up to 2 may be
      absent; if present, X is independently an amino acid residue other
      than cysteine

<400> SEQUENCE: 83

Xaa Xaa Xaa Cys Xaa Tyr His Xaa Gly Asn Leu Val Trp Cys Xaa Xaa
1               5                   10                  15

Xaa

<210> SEQ ID NO 84
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: misc_feature
<222> LOCATION: (1)..(3)
<223> OTHER INFORMATION: At least one X is present and up to 2 may be
      absent; if present, X is independently an amino acid residue other
      than cysteine
<220> FEATURE:
<221> NAME/KEY: misc_feature
<222> LOCATION: (6)..(6)
<223> OTHER INFORMATION: X is independently an amino acid residue other
      than cysteine
<220> FEATURE:
<221> NAME/KEY: misc_feature
<222> LOCATION: (8)..(8)
<223> OTHER INFORMATION: X is an arginine residue, a lysine residue, a
      leucine residue, or an asparagine residue
<220> FEATURE:
<221> NAME/KEY: misc_feature
<222> LOCATION: (15)..(17)
<223> OTHER INFORMATION: At least one X is present and up to 2 may be
      absent; if present, X is independently an amino acid residue other
      than cysteine

<400> SEQUENCE: 84

Xaa Xaa Xaa Cys Ala Xaa His Xaa Gly Glu Leu Val Trp Cys Xaa Xaa
1               5                   10                  15

Xaa
```

```
<210> SEQ ID NO 85
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: misc_feature
<222> LOCATION: (1)..(3)
<223> OTHER INFORMATION: At least one X is present and up to 2 may be
      absent; if present, X is independently an amino acid residue other
      than cysteine
<220> FEATURE:
<221> NAME/KEY: misc_feature
<222> LOCATION: (5)..(5)
<223> OTHER INFORMATION: X is an alanine residue, a serine residue, or a
      threonine residue
<220> FEATURE:
<221> NAME/KEY: misc_feature
<222> LOCATION: (6)..(6)
<223> OTHER INFORMATION: X is a tyrosine residue or tryptophan residue
<220> FEATURE:
<221> NAME/KEY: misc_feature
<222> LOCATION: (8)..(8)
<223> OTHER INFORMATION: X is an arginine residue, a lysine residue, a
      leucine residue, or an asparagine residue
<220> FEATURE:
<221> NAME/KEY: misc_feature
<222> LOCATION: (10)..(10)
<223> OTHER INFORMATION: X is a glutamic acid residue or an asparagine
      residue
<220> FEATURE:
<221> NAME/KEY: misc_feature
<222> LOCATION: (15)..(17)
<223> OTHER INFORMATION: At least one X is present and up to 2 may be
      absent; if present, X is independently an amino acid residue other
      than cysteine

<400> SEQUENCE: 85

Xaa Xaa Xaa Cys Xaa Xaa His Xaa Gly Xaa Leu Val Trp Cys Xaa Xaa
1               5                   10                  15

Xaa

<210> SEQ ID NO 86
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: misc_feature
<222> LOCATION: (1)..(3)
<223> OTHER INFORMATION: At least one X is present and up to 2 may be
      absent; if present, X is independently an amino acid residue other
      than cysteine
<220> FEATURE:
<221> NAME/KEY: misc_feature
<222> LOCATION: (8)..(8)
<223> OTHER INFORMATION: X is an arginine residue, a lysine residue, a
      leucine residue, or an asparagine residue
<220> FEATURE:
<221> NAME/KEY: misc_feature
<222> LOCATION: (15)..(17)
<223> OTHER INFORMATION: At least one X is present and up to 2 may be
      absent; if present, X is independently an amino acid residue other
      than cysteine
```

```
<400> SEQUENCE: 86

Xaa Xaa Xaa Cys Ala Tyr His Xaa Gly Glu Leu Val Trp Cys Xaa Xaa
1               5                   10                  15

Xaa

<210> SEQ ID NO 87
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: misc_feature
<222> LOCATION: (3)..(3)
<223> OTHER INFORMATION: X is an alanine residue or a threonine residue
<220> FEATURE:
<221> NAME/KEY: misc_feature
<222> LOCATION: (4)..(4)
<223> OTHER INFORMATION: X is a tyrosine residue or tryptophan residue
<220> FEATURE:
<221> NAME/KEY: misc_feature
<222> LOCATION: (6)..(6)
<223> OTHER INFORMATION: X is an arginine residue, a lysine residue, a
      leucine residue, or an asparagine residue
<220> FEATURE:
<221> NAME/KEY: misc_feature
<222> LOCATION: (8)..(8)
<223> OTHER INFORMATION: X is a glutamic acid residue or an asparagine
      residue

<400> SEQUENCE: 87

Asp Cys Xaa Xaa His Xaa Gly Xaa Leu Val Trp Cys Thr
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: misc_feature
<222> LOCATION: (3)..(3)
<223> OTHER INFORMATION: X is an alanine residue, a serine residue, or a
      threonine residue
<220> FEATURE:
<221> NAME/KEY: misc_feature
<222> LOCATION: (4)..(4)
<223> OTHER INFORMATION: X is a tryptophan residue or a tyrosine residue
<220> FEATURE:
<221> NAME/KEY: misc_feature
<222> LOCATION: (5)..(5)
<223> OTHER INFORMATION: X is a histidine residue, an arginine residue,
      a serine residue, or a threonine residue
<220> FEATURE:
<221> NAME/KEY: misc_feature
<222> LOCATION: (6)..(6)
<223> OTHER INFORMATION: X is an arginine residue, a lysine residue, a
      leucine residue, or an asparagine residue
<220> FEATURE:
<221> NAME/KEY: misc_feature
<222> LOCATION: (8)..(8)
<223> OTHER INFORMATION: X is a glutamic acid residue, an asparagine
      residue, an arginine residue, or an aspartic acid residue
<220> FEATURE:
<221> NAME/KEY: misc_feature
```

```
<222> LOCATION: (10)..(10)
<223> OTHER INFORMATION: X is an isoleucine residue or a valine residue

<400> SEQUENCE: 88

Asp Cys Xaa Xaa Xaa Xaa Gly Xaa Leu Xaa Trp Cys Thr
1               5                   10
```